US011713490B2

(12) United States Patent
Tang et al.

(10) Patent No.: US 11,713,490 B2
(45) **Date of Patent: *Aug. 1, 2023**

(54) **MARKER ASSISTED SELECTION OF TRAITS FOR PRODUCING MEAL FROM *BRASSICA NAPUS***

(71) Applicant: Corteva Agriscience LLC, Indianapolis, IN (US)

(72) Inventors: Shunxue Tang, Carmel, IN (US); Van L. Ripley, Grandora (CA); Thomas G. Patterson, Indianapolis, IN (US); Michelle Wiggins, Indianapolis, IN (US); Joshua A. Flook, Indianapolis, IN (US); Cherie Ochsenfeld, Indianapolis, IN (US); Daniel Garcia, Indianapolis, IN (US); Syed Masood Rizvi, Saskatoon (CA); Ryan Preuss, Indianapolis, IN (US); Donna Carolynn Knievel, Saskatoon (CA); Zoe Christina Ehlert, Saskatoon (CA); Steve Rounsley, Indianapolis, IN (US); Muhammad Tahir, Saskatoon (CA)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/064,284

(22) Filed: Oct. 6, 2020

(65) Prior Publication Data

US 2021/0092921 A1 Apr. 1, 2021

Related U.S. Application Data

(63) Continuation of application No. 15/731,561, filed as application No. PCT/US2015/066813 on Dec. 18, 2015, now Pat. No. 10,791,692.

(60) Provisional application No. 62/093,963, filed on Dec. 18, 2014.

(51) Int. Cl.

| | |
|---|---|
| ***A01H 5/10*** | (2018.01) |
| ***C12Q 1/6895*** | (2018.01) |
| ***A01H 1/04*** | (2006.01) |
| ***A01H 6/20*** | (2018.01) |
| *A23L 19/00* | (2016.01) |

(52) U.S. Cl.

CPC ............ *C12Q 1/6895* (2013.01); *A01H 1/04* (2013.01); *A01H 5/10* (2013.01); *A01H 6/202* (2018.05); *A23L 19/00* (2016.08); *C12Q 2600/13* (2013.01); *C12Q 2600/158* (2013.01)

(58) Field of Classification Search

None

See application file for complete search history.

(56) References Cited

U.S. PATENT DOCUMENTS

| | | | | |
|---|---|---|---|---|
| 10,791,692 | B2 * | 10/2020 | Tang | A01H 5/10 |
| 2010/0303999 | A1 | 12/2010 | Chungu et al. | |
| 2014/0220564 | A1 | 8/2014 | Zhang et al. | |

FOREIGN PATENT DOCUMENTS

| | | |
|---|---|---|
| WO | 2016100883 | 6/2016 |

OTHER PUBLICATIONS

Predicted *Brassica rapa* 2-isopropylmalate synthase 1, chloroplastic-like (LOC103842698) sequence, NCBI/GenBank accession No. XM_009119363, published Dec. 7, 2020.*

Predicted *Brassica rapa* post-GPI attachment to proteins factor 3-like (LOC103842843), transcript variant X2, NCBI/GenBank accession No. XM_009119508, published Dec. 7, 2020.*

Batista et al., 2011, Nutritional and nutraceutical potential of rape (*Brassica napus* L. var. napus) and "tronchuda" cabbage (*Brassica oleraceae* L. var. costata) inflorescences, Food and Chemical Toxicology 49: 1208-1214.*

Akhov et al. 2009, Botany + Botanique 87(6):616-625.

Badani et al. 2006, Genome 49:1499-1509.

Chalhoub et al. 2014, Science 345 (6199), 950-953.

Clarke et al. 2013, PLoS ONE 8(12): e81992.

Clarke et al. 2016, Supplemenary Table 1 of Clarke et al. 2016, Theor Appl Genet; 129(10): 1887-1899.

Clarke et al. 2016, Theor Appl Genet; 129(10): 1887-1899.

Edwards et al. 2012, Theor Appl Genet; 126: 1-11.

EP Opposition 3234197B1—Declaration SNOWDON dated Jul. 26, 2021, submitted in Opposition of EP3234197B1 dated Aug. 9, 2021.

EP Opposition EP3234197B1—Cited Doc D7b Alignment of selected sequences in SRX277527 and EP3234197B1.

EP Opposition EP3234197B1—Cited Document S8a, Alignment of selected sequences in *Brassica napus* 60K Illumina InfiniumTM SNP Array and EP3234197B1.

EP Opposition EP3234197B1 Cited Document D15_p. 7 of Amendment filed in U.S. Appl. No. 15/731,561 dated Apr. 29, 2020.

EP Opposition EP3234197B1_Cited Document D18_Alignment of sequence rs# 21212 of Wang et al. Aug. 2016 with SEQ ID Nos. 14-17 of the Patent highlighting relevant SNPs, submitted on Jan. 2, 2022.

(Continued)

*Primary Examiner* — Medina A Ibrahim

(57) ABSTRACT

A method for identifying a quantitative trait locus associated with desirable nutritional traits in canola includes: analyzing a population of canola plants or germplasm for desirable nutritional traits; determining the genotype of the canola plants or germplasm using at least one marker selected from the group consisting of SEQ ID NO:1 through SEQ ID NO:111; mapping the canola plants or germplasm for the presence of a quantitative trait locus (QTL) associated with the markers; and associating the QTL with the desirable nutritional trait. An isolated and/or recombinant nucleic acid includes a sequence associated with a quantitative trait locus (QTL), wherein the QTL is associated with a desirable nutritional trait in a canola plant or germplasm and wherein the QTL is further associated with at least one marker selected from the group consisting of SEQ ID NO:1 through SEQ ID NO:111.

18 Claims, 8 Drawing Sheets

Specification includes a Sequence Listing.

(56) References Cited

OTHER PUBLICATIONS

EP Opposition EP3234197B1_Cited Document D8a_Alignment of selected sequences in Table 4 of Wang et al 2015 and EP3234197B1, submitted on Aug. 9, 2021.
EP Opposition EP3234197B1_Notice of Opposition_submitted in the European Patent Office dated Aug. 9, 2021.
EP Opposition EP3234197B1_Response to Notice of Opposition to EP3234197B1, submitted in the European Patent Office dated Jan. 2, 2022.
Infinium® Assay Workflow, Illumina, <http://www.bea.ki.se/documents/workflow_infinium.pdf>, Oct. 11, 2012, 2 pages.
International Search Report and Written Opinion for PCT/US2015/066813, dated Apr. 11, 2016.
Liu et al. 2013, PLoS One 8(12) e83052: 1-9.
McEntyre et al., The NCBI Handbook [Internet] Bethesda (MD): National Center for Biotechology Information (US), "Chapter 5 The Single Nucleotide Polymorphism Database (dbSNP) of Nucleotide Sequence Variation" (by Adrienne Kitts and Stephen Sherry), retrieved from https://www.ncbi.nlm.nih.gov/books/NBK21088/.
NCBI—DH12075 Submission Sep. 11, 2013.
NCBI—SRX277527, YN429 Sequence Capture—Jul. 17, 2014.
NCBI/GenBank accession No. XM_009119363, dated Oct. 13, 2016, Predicted *Brassica rapa* 2-isopropylmalate synthase 1, chloroplastic-like (LOC103842698) sequence.
NCBI/GenBank accession No. XM_009119508, dated Oct. 13, 2016, Predicted *Brassica rapa* post-GPI attachment to proteins factor 3-like (LOC103842843), transcript variant X1 sequence.
Nelson et al. 2012, Trends in Genetics 28(8): 361-363.
Nesi et al. 2008, Comptes Rendus Biologies 331:763-771.
Oraby et al. 2014, Eur Food Res Technol. 240:931-938.
Relf-Eckstein et al. 2007, Feed and Industrial Raw Material pp. 289-291.
Shoaib et al. 2014, Pak. J. Agri. Sci., vol. 51(2), 443-449.
Slominski et al. 2012, Agric, Food Chem; 60, 12225-12230.
Slominski 2015—slide deck retrieved from https:www.agwest.sk.ca/IRC2015/BSlominskiCanolameal.pdf.
Somers et al. 2001, Genome:44 (6):1077-8.
Wang et al. 2015, PLoS ONE 10(12): e014045 Dec. 16, 2015.
Yan et al. 2009, Euphytica 170:355-364.

* cited by examiner

LOD0
1 : WI_A
2 : WI_D
3 : L
6 : ADF_A
7 : ADF_W
WI_A: White Index from AAFC
WI_D: White Index from DAS
L: Hunter Lab Lightness Index L from DAS
ADF_A: ADF (NIR) data from AAFC
ADF_W: ADF (Wet Chemistry) data from DAS
LOD Threshold: 3.0
cM
ADF_A
WI_A
ADF_W
WI_D
L

MARKER ASSISTED SELECTION OF TRAITS FOR PRODUCING MEAL FROM *BRASSICA NAPUS*

CROSS-REFERENCE TO RELATED APPLICATIONS

This application is a continuation of U.S. patent application Ser. No. 15/731,561, filed on Jun. 27, 2017 and issued on Oct. 6, 2020 as U.S. Pat. No. 10,791,692, which is a national phase entry under 35 U.S.C. § 371 of International Patent Application PCT/US2015/066813, filed on Dec. 18, 2015, published in English as International Patent Publication No. WO20160100883 on Jun. 23, 2016, which claims priority to U.S. Provisional Application No. 62/093,963, filed Dec. 18, 2014, all of which are incorporated in their entirety by reference herein.

INCORPORATION BY REFERENCE OF MATERIAL SUBMITTED ELECTRONICALLY

The official copy of the sequence listing is submitted via EFS-Web as an ASCII formatted sequence listing with a file named "72430-US-PCN ST25", created on Dec. 14, 2020, having a size of 126 kilobytes. The sequence listing contained in this ASCII formatted document is part of the specification, and is incorporated by reference herein in its entirety.

TECHNICAL FIELD

The disclosure relates to fine mapping of quantitative trait loci (QTLs) associated with low fiber content and YSC traits and identification of SNP markers for marker assisted selection of these traits in *Brassica napus.*

BACKGROUND

Canola (*Brassica napus* L., 2n=4x=38, AACC), an allotetraploid formed from diploids *B. rapa* (2n=2x=20, AA) and *B. oleracea* (2n=2x=18, CC), is one of the most important vegetable oilseed crops in the world, especially in China, Canada, the European Union and Australia. Canola meal, the fraction of the seed remaining after crushing and oil extraction, is approximately 55% of the volume of canola seed.

Canola meal consists of several components including protein, fiber, residual oil, carbohydrates, and anti-nutritional factors. Canola meal contains approximately 75% of the protein of 48% protein soybean meal, 80% of the energy value, and 300% of the crude fiber, as well as higher levels of anti-nutritional factors such as glucosinolates, tannins, phytic acid, sinapine and erucic acid, and is sold as livestock feed at 60%-70% of the price of soybean meal. See, e.g., Hickling (2007) Canola meal competitive situation and Canola Council of Canada goals, Canola Meal Research Meeting, Saskatoon, Canada; Newkirk (2009) Canola meal feed industry guide (4th Edition). The relatively high fiber content of canola meal is a significant limiting factor for its use in monogastric animal species (Hickling, 2007; Newkirk, 2009). Since meal comprises half of the seed volume of canola, and demand for biodiesel could drive a 67% increase in rapeseed seed production from 2006 to 2015 (Hickling, 2007), there is a need to modify the compositional properties of canola meal and thereby increasing its nutritional value relative to soybean.

Scientists at Agriculture and Agri-Foods Canada (AAFC) have developed yellow seed coat (YSC) lines (YN86-37, YN90-1016, YN97-262 and YN01-429) of low hull proportion with thinner seed coat, low fiber and high oil compared to the black seed coat (BSC) canola (Rakow et al., 2011). Feeding studies, comparing yellow seeded canola meal from AAFC line YN01-429 to *B. juncea, B. rapa*, and brown-seeded *B. napus*, demonstrated the advantages of YSC *B. napus* line such as higher protein, lower fiber, increased amino acid digestibility and metabolizable energy content, and improved nutrient and energy utilization based on feed to gain ratio in broiler chickens and monogastric animal species (Hickling, 2009; Slominski et al., 2010).

The breeding of low fiber content has been greatly hampered by a poor understanding of the inheritance and stability of the low fiber content traits, as well as a lack of robust, high-throughput markers tightly linked to the trait. Due to allotetraploidy, effect of multiple genes, maternal effects and environmental effects, the inheritance of low fiber content trait is complex, and identification of markers tightly linked to this trait is very challenging. Somers et al, (2001) reported identification of eight random amplified polymorphic DNA (RAPD) markers for a major gene (pigment1) associated with yellow seed coat trait from YSC line YN90-1016, the low fiber content source of YN97-262 and YN01-429 used in the applicant's Low Fiber breeding program (Rakow et al., 2011). The major gene explained 72.3% of the variation in seed color, while two additional genes that appeared to be additive explained 21.5% of the color variation (Somers et al., 2001).

It has been suggested that the low fiber content of AAFC YSC line YN01-429 and its lineage might be controlled by three recessive genes (Kubik and Thompson, 2009). Current selection of lower fiber canola lines has primarily been based on fiber content data obtained using cost and labor intensive analytical methods, or seed coat color, because of its high correlation with low fiber in the AAFC YSC lines YN97-262 and YN01-429.

SUMMARY OF DISCLOSURE

A particular embodiment of the invention includes a method for identifying quantitative trait locus associated with desirable nutritional traits in canola. The method includes analyzing a population of canola plants or germplasm for desirable nutritional traits. The genotype of the canola plants or germplasm is determined using at least one marker selected fro the group consisting of SEQ ID NO:1 through SEQ ID NO:111. The canola plants or germplasm are mapped for the presence of a quantitative trait locus (QTL) associated with the markers. The QTL is associated with the desirable nutritional trait.

Another embodiment relates to an isolated and/or recombinant nucleic acid having a sequence associated with a QTL. The QTL is associated with a desirable nutritional trait in a canola plant or germplasm. The QTL is further associated with at least one marker selected from the group consisting of SEQ ID NO:1 through SEQ ID NO:111.

Yet another embodiment relates to a method for selecting a canola plant or germplasm that comprises desirable nutritional traits. The method includes detecting in the canola plant or germplasm at least one marker linked with a QTL that is selected from the group consisting of SEQ ID NO:1 through SEQ ID NO:111, wherein the QTL is associated with a desirable nutritional trait in the canola plant or germplasm. A canola plant or germplasm is then selected based on the presence of the marker.

The foregoing and other features will become more apparent from the following detailed description of several embodiments, which proceeds with reference to the accompanying figures.

DISCLOSURE

Described herein are high-throughput single nucleotide polymorphism (SNP) markers and high-density genetic maps for fine mapping and validation of quantitative trait loci (QTL) underlying fiber content and seed coat color traits. In some embodiments, SNP markers tightly linked to fiber content and seed coat color traits may be used for marker-assisted selection (MAS) of desirable nutritional traits in yellow-seeded canola (YSC) lines. In particular embodiments, the YSC line may be AAFC YSC line YN01-429 and its lineage.

Also disclosed is a method of leveraging SNP markers and high-density genetic maps based on fiber content and seed coat color traits from AAFC YSC line YN01-429, using an extensive set of phenotypic data of two DH populations. In a particular embodiment, a major QTL, which explains 59.2% to 74.7% of the variance of fiber content and seed coat color traits, is described on N09 in two DH populations, and a minor QTL, which explains 1.4% to 7.2% of the variance of fiber content and seed coat color traits, is described on N11 in two DH populations. High correlation ($R^2$=0.67-0.85) exists between seed coat color traits (WI and L) and ADF content in both populations.

Figure 8:
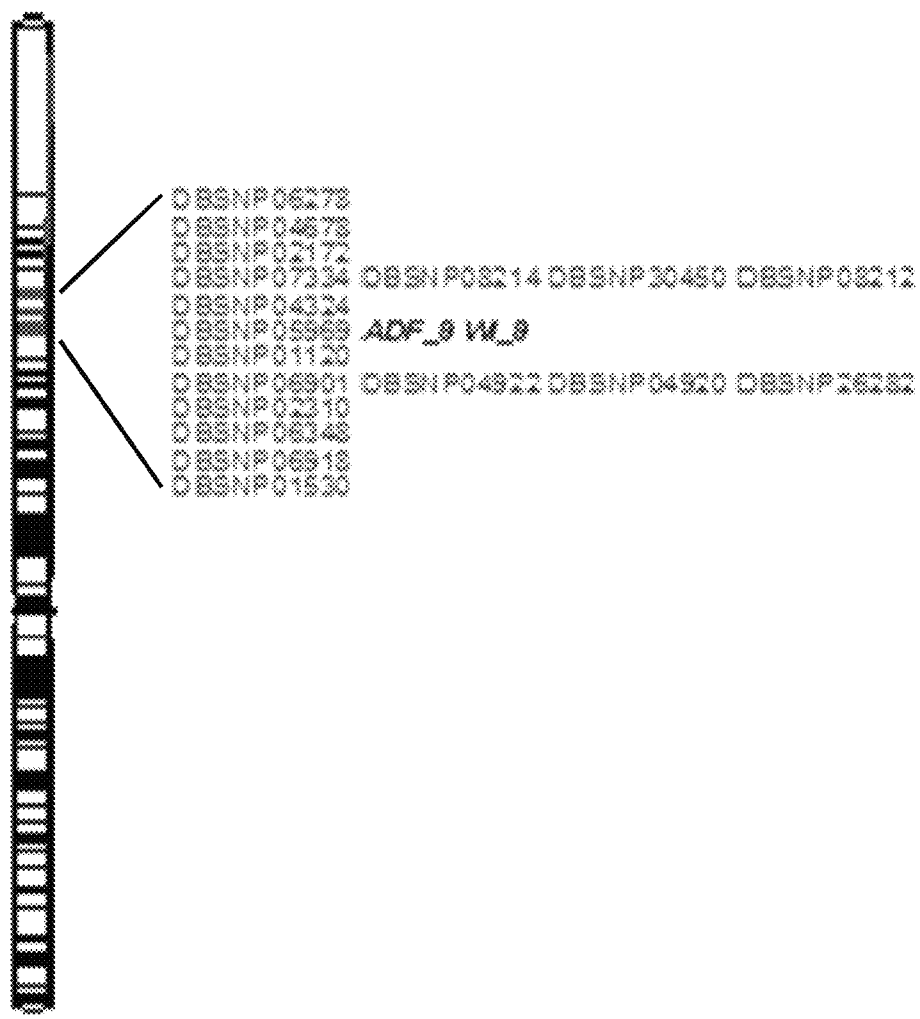
FIG. 8 shows a map of N09 constructed with N09 of YDN, YSC and TN DH populations, showing 18 SNP markers identified within 0.0-4.9 cM to a major QTL underlying fiber content (ADF_9) and seed coat color (WI_9) on N09.

Also disclosed herein are 18 SNP markers within 0.0-4.9 cM of the major fiber content and seed coat color QTL on N09 (see FIG. 8), and 40 SNP markers within 0.0-4.1 cM of the minor fiber content and seed coat color QTL on N11, which may be used in embodiments for marker-assisted selection of complex low fiber content and YSC traits from YSC line YN01-429 and its lineage, and thus may improve the breeding process of canola lines with low ADF content if YN01-429 or it lineage is used as a low fiber content source in breeding programs.

An Low Fiber product which aims to improve the nutritional value of commercial canola meal to 85-90% of the value of 48% protein soybean meal by increasing protein content (from 36% to 44%) and true metabolizable energy (TME) (a 16%-20% increase), and decreasing fiber content (from 15-19% to less than 10%) has been developed. These improvements are anticipated to increase the nutritive value of canola meal, particularly in monogastric species, and should allow increasing dietary inclusion rates.

YSC lines (YN86-37, YN90-1016, YN97-262 and YN01-429) of low hull proportion with a thinner seed coat, low fiber and high oil as compared to black seed coat (BSC) canola (Rakow et al., 2011) also have been developed. Feeding studies comparing yellow-seeded canola meal from AAFC line YN01-429 to *B. juncea, B. rapa*, and brown-seeded *B. napus* have demonstrated the advantages of the YSC *B. napus* line, including higher protein, lower fiber, increased amino acid digestibility and metabolizable energy content, and improved nutrient and energy utilization based on feed to gain ratio in broiler chickens and monogastric animal species (Hickling, 2009; Slominski et al., 2010).

Combinations of the yellow seeded/low fiber traits from YSC lines YN97-262 and YN01-419 with the Omega 9 fatty acid profile, as well as other desirable agronomic and seed quality attributes, have been studied.

I. Mapping and Validation of Low Fiber Content and YSC Traits from YN01-429

In a preferred embodiment, the disclosure describes a method for identifying and mapping quantitative trait loci (QTL) associated with low fiber content and yellow seed coat (YSC) traits in *Brassica napus* using single-nucleotide polymorphism (SNP) markers. In embodiments, the QTLs are defined in YSC line YN01-429. In some embodiments, the markers may be used for marker-assisted selection of low fiber content and YSC traits derived from YSC line YN01-429 and its lineage.

SNP markers and high-density genetic maps were leveraged, and fiber content and seed coat color traits were fine mapped and validated from AAFC YSC line YN01-429 with an extensive set of phenotypic data from two dihaploid (DH) populations. These experiments are outlined in greater detail in Examples 1-5. Two DH populations, YSC and YDN, were developed from spring canola line crosses. The 183 DH lines of the YSC population were developed from a cross between AAFC yellow seeded/low fiber line YN01-429 and DAS Nexera black seeded/high fiber variety Nex828, and grown along with the two parents in paired row plots at the AAFC Saskatoon research farm and the DAS Rosthern research farm in Canada in 2007 for phenotyping. Seed samples from two locations were analyzed by AAFC using near-infrared spectroscopy (NIR) ADF (named ADF_A in FIGS. 3 and 4) and using Hunter lab for seed coat color White Index (named WI_A in FIGS. 3 and 4) measurement in 2007. The population was also analyzed by DAS Analytical Technologies Group in Indianapolis for ADF (named ADF_A in FIGS. 3 and 4) using the AOAC reference method (AOAC Official Method 973.18) and by DAS Bioprocess Group in Indianapolis for seed coat color White Index (named WI_D in FIGS. 3 and 4) and Hunter Lab Lightness Index (named L in FIGS. 3 and 4) measurement in 2011. The 400 DH lines of the YDN population were developed from a cross between YN01-429 and DAS Nexera black seeded/high fiber variety DN051493. The YDN population was grown along with the two parents at Pike Lake and Cudworth, Canada in 2011 for phenotyping. Seed samples were analyzed for ADF (named ADF_M1 and ADF_M2 in FIGS. 5 and 6), seed coat color White Index (named WI in FIGS. 5 and 6) and Hunter lab Lightness Index (name L in the FIGS. 5 and 6). A third DH population of 181 DH lines (named TN population) from a cross between Tapidor (a European winter cultivar) and Ningyou7 (a Chinese semi-winter cultivar) was added for consensus map construction in addition to YSC and YDN populations for QTL mapping of fiber content and seed coat color traits; TN population did not segregate for fiber content and seed coat color traits. The three DH populations were genotyped with 12,000 SNP markers and a consensus map was constructed with individual map of the YSC, YDN and TN populations. Composite Interval Mapping (CIM) was used for a whole genome QTL scan. After QTL mapping, the SNP markers within 0.0-5.0 cM of the QTL underlying fiber content and seed coat color traits were converted to KASPar assays for MAS of these traits derived from YN01-429 and its lineage.

Figure 1:
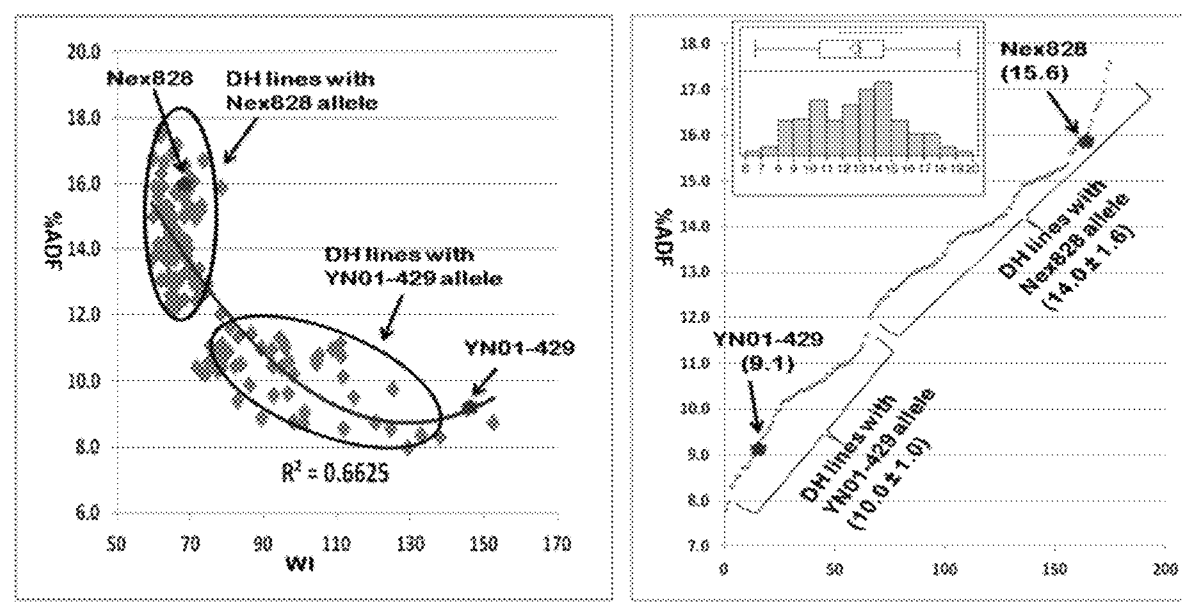
FIG. 1 shows the distribution of White Index (WI) and % ADF in Nex828×YN01-429 (YSC) DH lines. The left figure shows the White Index (WI) of seed coat color plotted against % of ADF in canola seed. The right figure shows the distribution of % ADF among DH lines. The number in bracket indicated % of ADF in canola seed.
Figure 2:
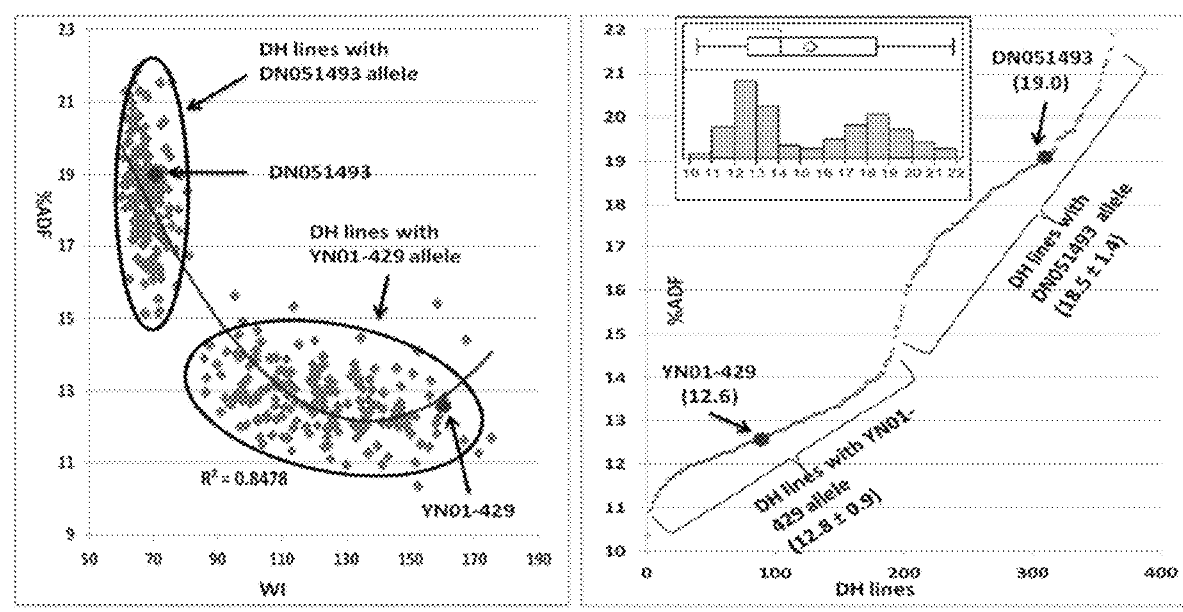
FIG. 2 shows the distribution of White Index (WI) and % ADF in DN051493×YN01-429 (YDN) DH lines. The left figure shows White Index (WI) of seed coat color plotted against % of ADF canola seed. The right figure shows the distribution of % ADF among DH lines. The number in bracket indicated % of ADF in canola seed.
Figure 7:
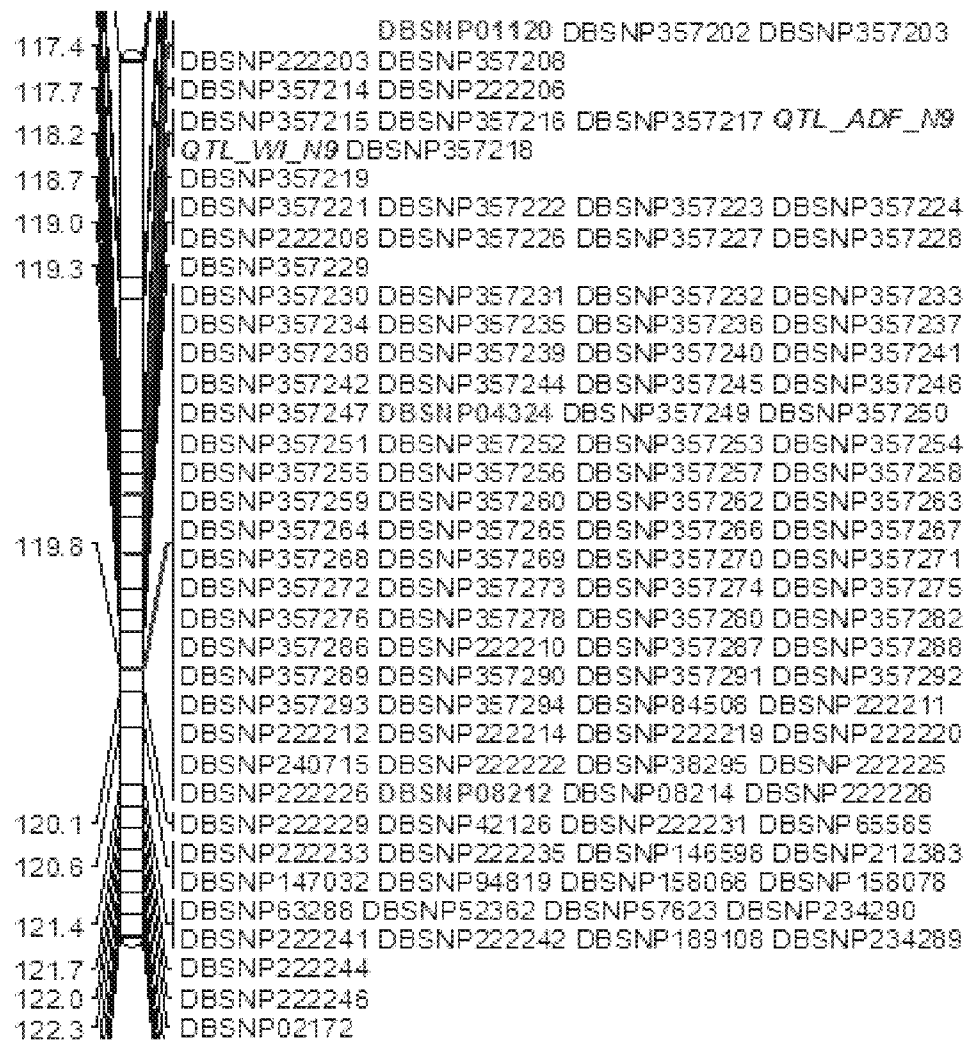
FIG. 7 shows a Map of the major ADF QTL interval on N09, constructed with the YDN DH population. Within the 4.9 cM QTL interval, 111 SNP markers were identified, including the flanking markers DBSNP01120 and DBSNP02172. The ADF_9 and WI_9 loci are also mapped within the interval.

High correlation was also observed between the seed coat color traits WI and L ($R^2$=0.81-0.99) and between seed coat color traits and ADF content ($R^2$=0.66-0.85) in both populations (FIGS. 1 and 2). Because of the large effect of the major QTL (R2=59.2%-74.7%) on N09, and bi-modal distributions of fiber content and seed coat color traits in DH lines (FIGS. 1 and 2), quantitative fiber content and seed coat color traits can be treated as qualitative traits. After conversion of the quantitative traits of ADF and WI into qualitative traits, the ADF (ADF_09) and WI (WI_09) were mapped to the same genomic region where the major QTL were located on N9 in both YSC and YDN populations. FIG. 7 shows the map location of major ADF and WI QTL, ADF_09 and WI_09 on the consensus map of N09 constructed with YSC, YDN and TN populations and 323 SNP markers.

Somers et al. (2001) and Rakow et al. (2011) indicated that the YSC line from AAFC delivers consistently low fiber content across multiple environments, and low lignin content is always associated with the yellow seed color. The YSC genetic map was constructed with 174 DH and 2,982 polymorphic SNP markers, a total length of 2,515.8 cM and an average length of 0.80 cM/marker. The YDN population was constructed with 397 DH lines and 2,972 SNP markers, a total length of 2,189 cM and an average length of 0.74 cM/marker. The TN genetic map was constructed with 181 DH lines and 2,716 polymorphic SNP markers, a total length of 1905.7 cM and an average length of 0.70 cM/marker. In embodiments, the disclosure describes a consensus map of 5,500 SNP markers with an average of 0.47 cM constructed with the YDN, YSC and TN populations (FIG. 7).

Figures 3A, 3B:
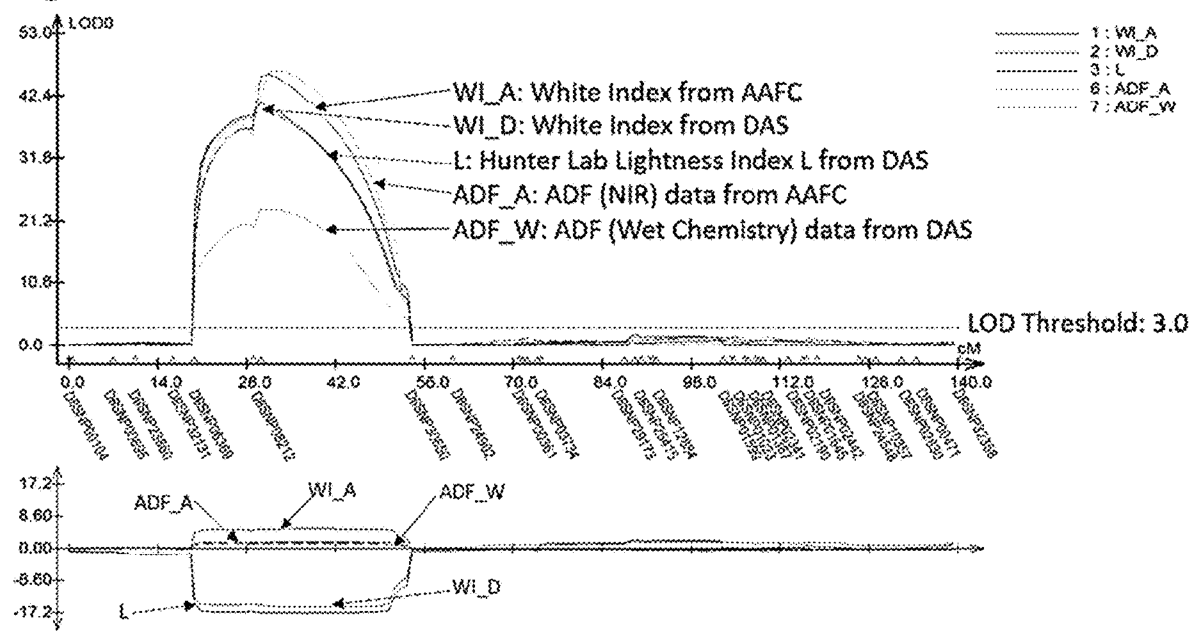
FIG. 3A shows the location (X-axis) and significance (LOD score on Y-axis) of the QTL identified on N09.
FIG. 3B shows the additive effect of the QTL identified on N09.
Figures 4A, 4B:
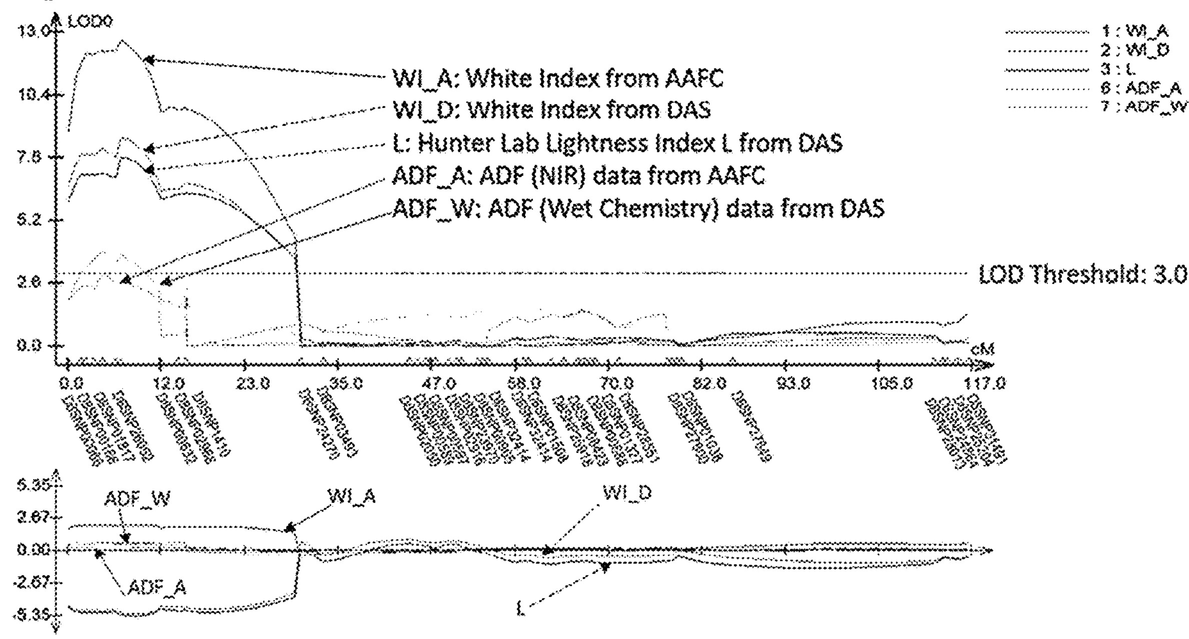
FIG. 4A shows the location (X-axis) and significance (LOD score on Y-axis) of the QTL identified on N11.
FIG. 4B shows the additive effect of the QTL identified on N09.
Figures 5A, 5B:
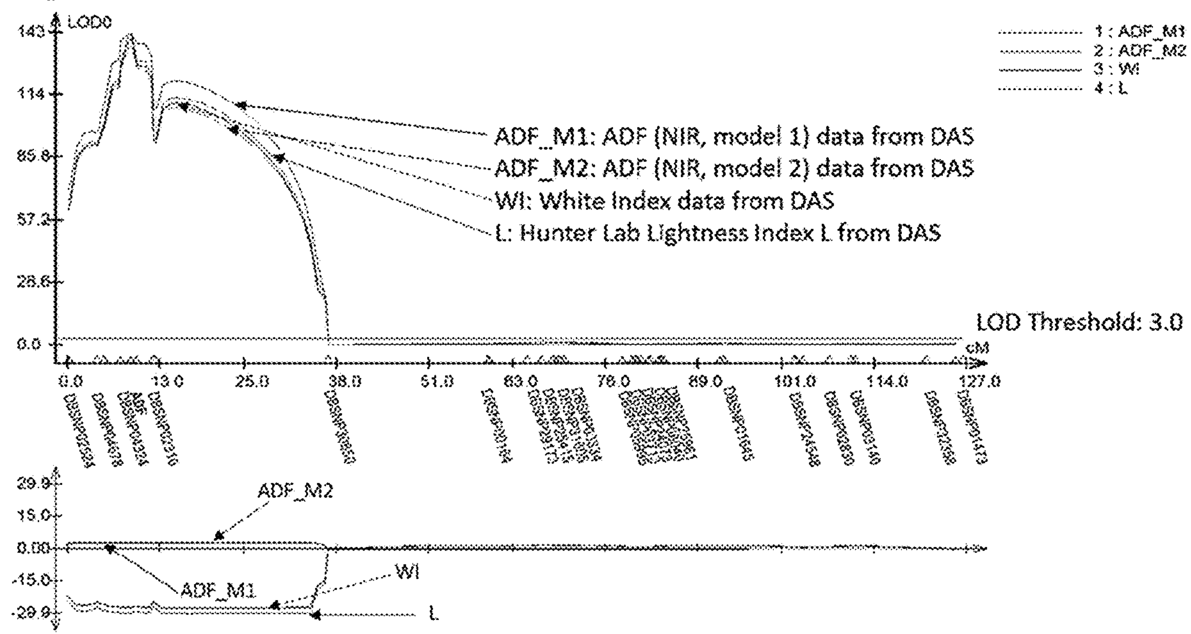
FIG. 5A shows the location (X-axis) and significance (LOD score on Y-axis) of the QTL identified on N09.
FIG. 5B shows the additive effect of the QTL identified on N09.
Figures 6A, 6B:
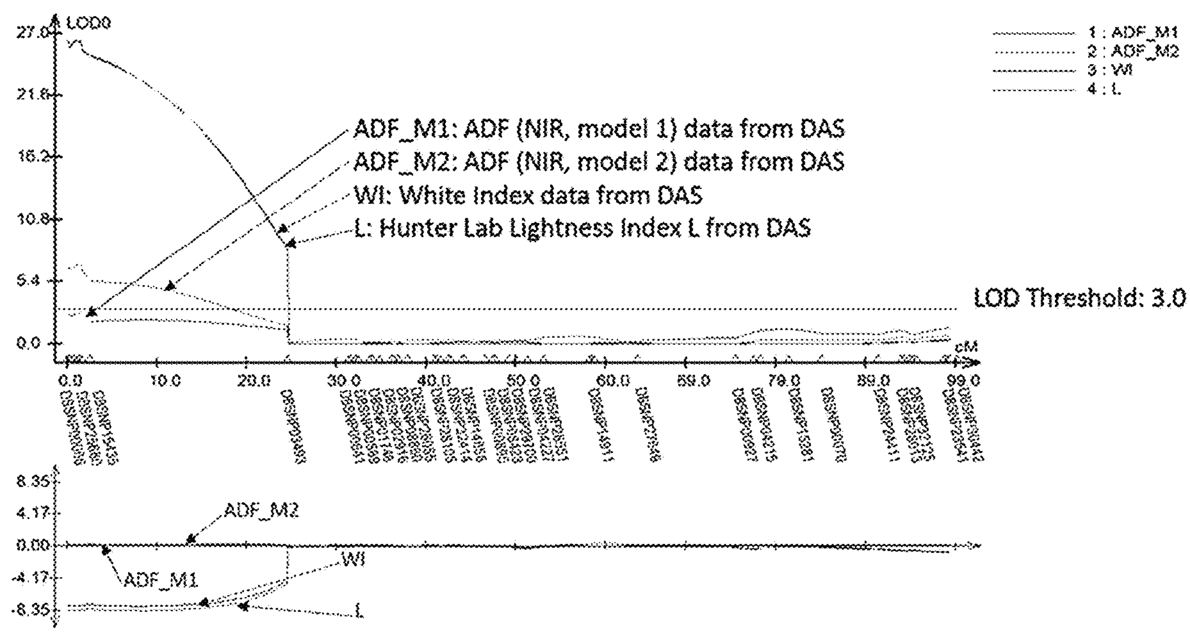
FIG. 6A shows the location (X-axis) and significance (LOD score on Y-axis) of the QTL identified on N11.
FIG. 6B shows the additive effect of the QTL identified on N11.

YSC and YDN populations segregated for fiber content and seed coat color traits and were used for QTL mapping, which further confirmed that seed coat color traits and fiber content traits were highly correlated (FIGS. 3-6). QTL mapping indicated that a major QTL was identified on linkage group (LG) N09 and a minor QTL was identified on LG N11 for all the seed coat color traits (WI and L) and ADF content in both populations (FIGS. 4-6).

In the YSC population, the major QTL identified on N09 explained 71.5% of ADF variance, and coincided with major QTL which explained 59.2% of WI and 60.8% of Lightness Index (L) variance at LOD scores ranged from 40 to 47 (FIG. 3). The minor QTL identified on N11 explained 2.4% of ADF variance, and coincided with the minor QTL which respectively explained 7.2% of WI and 6.3% of Lightness Index (L) variance at LOD scores ranged from 5 to 9 in Nex828×YN01-429 population (FIG. 4).

QTL analysis of YDN population further confirmed the results from YSC population. The major QTL identified on N09 explained 73.4% of ADF variance and coincided with the major QTL which respectively explained 74.0% of WI and 74.7% of Lightness Index (L) variance at LOD score 143 (FIG. 5). The minor QTL identified on N11 explained 1.4% of ADF variance, and coincided with the minor QTL which respectively explained 5.9% of WI and 5.7% of Lightness Index (L) variance at LOD scores ranged from 3 to 32 (FIG. 6). The results were in accordance with Somers et al. (2001) results, which indicated that a major gene explained 72.3% of the variation in seed color, as well as two additional genes that appeared to be additive and explained 21.5% of the color variation. Since seed coat color QTL (WI and L) perfectly coincided with QTL for fiber content and explained the almost the same percentage of phenotypic variance (R2=77.4%) as QTL for ADF content in both YN01-429 derived DH populations, seed coat color indexes (WI and L) were good indicators for the fiber content in canola seed if YSC line YN01-429 or its lineage is used as a low ADF content source in breeding programs.

II. SNP Markers and QTL Underlying Low Fiber Content and YSC Traits from YN01-429

In some embodiments, the disclosure describes a major QTL which explains 59.2-74.7% of the phenotypic variance of fiber content and seed coat color traits in two dihaploid (DH) plant populations. In particular embodiments, a minor QTL has been found to explain 1.4-7.2% of the phenotypic variance of these traits in two dihaploid plant populations. High correlation is disclosed between seed coat color traits (WI and L) and ADF content in both populations.

In an alternative embodiment, a set of high throughput markers closely linked to fiber content and seed coat color traits from YSC line YN01-419. In other embodiments, nucleic acid sequences linked to QTL's are associated with desirable nutritional traits. The sequence can be derived from yellow-seeded coat (YSC) line YN01-429 or its lineage. Particular embodiments related to a set of 18 SNP markers that lie within 0.0-4.9 cM of the major ADF and seed color (WI) QTL identified in Nex828×YN01-429 (YSC) and DN051493×YN01-429 (YDN) DH populations.

In a particular embodiment, the SNP markers include those markers identified as DBSNP357222 through DBSNP2222111 in FIG. 7, which flanked by DSNP01120 and DSNP02172. In another embodiment, the SNP markers include DBSNP357223, DBSNP357224, DBSNP357226, DBSNP357227, DBSNP357228, DBSNP357230, DBSNP357231, DBSNP357233, DBSNP357234, DBSNP357244, DBSNP357247, DBSNP357250, DBSNP357252, DBSNP357253, DBSNP357254, DBSNP357255, DBSNP357256, DBSNP357257, DBSNP357258, DBSNP357273, DBSNP357287, DBSNP357288, DBSNP357290, DBSNP357291, DBSNP357292, DBSNP357293, and DBSNP357294, as shown in FIG. 7.

II. Marker-Assisted Selection (MAS) of Low Fiber Content and YSC Traits from YN01-429

Certain embodiments related to a method for selecting canola plants or germplasm for a desirable nutritional trait associated with QTL's using marker-assisted selection (MAS). For example, the YSC line YN01-429 may be used. Seed color measurement may be used to replace costly and time-consuming wet chemistry analysis of fiber content SNP markers disclosed to be within 4.9 cM of the major fiber content and seed coat color QTL on N09 or the minor fiber content and seed coat color QTL on N11 can be used for MAS, and will greatly expedite the breeding of canola lines with low fiber content, one of the most important components of DAS Low Fiber product concept.

Particular embodiments describe a method for using the identified QTL in marker-assisted selection (MAS) of the complex fiber content and seed coat color traits from the YSC line YN01-429 to facilitate breeding in *Brassica* and more efficient selection of desirable nutritional traits. Particular embodiments are directed to marker-assisted selection of canola varieties to increase the nutritive value of canola meal, particularly for feed animals, including monogastric animals and ruminants.

According to certain embodiments, the method may be used to select canola seed or germplasm comprising, on average, at least about 44% crude protein, and not more than about 14% acid detergent fiber as determined by NIR on a dry mass basis. In alternative embodiments, the canola seed or germplasm may further comprise, on average, at least about 49% crude protein content. In other embodiments, the canola seed or germplasm may comprise on average, not more than about 12% acid detergent fiber content. Additionally, the canola seed or germplasm selected by the disclosed method may further comprise the following traits: reduced glucosinolate content, low tannin content, and/or low residual cell wall content.

IV. Abbreviations

ADF acid detergent fiber
AME apparent metabolizable energy
DAS Dow AgroSciences
DH dihaploid
FAME fatty acid/fatty acid methyl esters
NMR nuclear magnetic resonance
NIR near-infrared spectroscopy
QTL quantitative trait locus
RAPD random amplified polymorphic DNA
SNP Single nucleotide polymorphism
RCW residual cell walls

V. Terms

Allotetraploid: As used herein, "allotetraploid" generally refers to a hybrid organism that has a chromosome set that is four times that of a haploid organism.

Canola oil: Canola oil refers to oil extracted from commercial varieties of rapeseed. To produce canola oil, seed is typically graded and blended at grain elevators to produce an acceptably uniform product. The blended seed is then crushed, and the oil is typically extracted with hexane and subsequently refined. The resulting oil may then be sold for use. Oil content is typically measured as a percentage of the whole dried seed, and particular oil contents are characteristic of different varieties of canola. Oil content can be readily and routinely determined using various analytical techniques, for example and without limitation: NMR; NIR; and Soxhlet extraction. The percent composition of total fatty acids is typically determined by extracting a sample of oil from seed, producing methyl esters of fatty acids present in the oil sample, and analyzing the proportions of the various fatty acids in the sample using gas chromatography. The fatty acid composition may also be a distinguishing characteristic of particular varieties.

Elite line: As used herein, the term "elite line" means any line that has resulted from breeding and selection for superior agronomic performance. An elite plant is any plant from an elite line.

Enhanced canola meal: As used herein, the term "enhanced canola meal" means canola meal, produced from canola seeds, which has decreased fiber content, and may have increased protein and true metabolizable energy content, as well as reduced anti-nutritional factors such as glucosinolates, tannins, phytic acid, sinapine and erucic acid. Meal with some or all of these characteristics could allow increasing inclusion rates in the diet of animal species especially in monogastric animals.

Plant line: As used herein, a "line" refers to a group of plants that display little genetic variation (e. g., no genetic variation) between individuals for at least one trait. Inbred lines may be created by several generations of self-pollination and selection or, alternatively, by vegetative propagation from a single parent using tissue or cell culture techniques. As used herein, the terms "cultivar," "variety," and "type" are synonymous, and these terms refer to a line that is used for commercial production.

Plant material: As used herein, the term "plant material" refers to any processed or unprocessed material derived, in whole or in part, from a plant. For example and without limitation, a plant material may be a plant part, a seed, a fruit, a leaf, a root, a plant tissue, a plant tissue culture, a plant explant, or a plant cell.

Quantitative trait: As used herein, a "quantitative trait" may refer to a trait or phenotype that is expressed in varying degrees, along a generally continuous gradient and is frequently linked to two or more genes and is affected by environment Quantitative trait locus: As used herein, a "quantitative trait locus" refers to a segment or region of DNA containing or linked to a gene or genes underlying a quantitative trait.

Seed color: In some embodiments, this disclosure refers to canola varieties (e.g., inbred canola lines and hybrids) characterized by seed color. Canola seed color rating or "seed color" is generally scored on a 1-5 scale, based on seeds obtained from healthy plants at or near complete seed maturity. "1" signifies a good yellow color. "2" signifies mainly yellow with some brown. "3" indicates a mixture of brown and yellow. "4" and "5" signify brown and black, respectively. Whiteness index (WI) scores also may be used to describe canola varieties. For example, yellow-seeded lines YN97-262 and 9592 have whiteness index scores of −34.6 and −33.2, respectively, and seed color scores of 1. Dark-seeded lines, Nex 715 and Nex 705, have whiteness index scores of −0.2 and −4.4, respectively, and seed color scores of 4. Dark-seeded lines 46A65 and Q2 have whiteness index scores of 0.3 and −3.9, respectively, and seed color scores of 5. Color of particular seeds may also be described in terms of a percentage, or other ratio, as compared to any of these lines.

Stability: As used herein, the term "stability," or "stable," refers to a given plant component that is maintained at substantially the same level through multiple generations. For example, a stable component may be maintained for at least three generations at substantially the same level. In this context, the term "substantially the same" may refer in some embodiments to a component maintained to within 25% between two different generations; within 20%; within 15%; within 10%; within 5%; within 3%; within 2%; and/or within 1%, as well as a component that is maintained perfectly between two different generations. In some embodiments, a stable plant component may be, for example and without limitation, an oil component; a protein component; a fiber component; a pigment component; a glucosinolate component; and a lignin component. The stability of a component may be affected by one or more environment factors. For example, the stability of an oil component may be affected by, for example and without limitation: temperature; location; stress; and the time of planting. Subsequent generations of a plant having a stable component under field conditions will be expected to produce the plant component in a similar manner, for example, as set forth above.

Trait or phenotype: The terms "trait" and "phenotype" are used interchangeably herein. For the purposes of the present disclosure, the traits of particular interest are low fiber content and seed coat color. Some canola varieties exhibit a yellow seed coat, while further varieties exhibit a dark (e.g., black, dark, and mottled) seed coat.

A "variety" or "cultivar" is a plant line that is used for commercial production which is distinct, stable and uniform in its characteristics when propagated.

Unless indicated otherwise, the terms "a" and "an" as used herein refer to at least one.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

EXAMPLES

The following Examples are provided to illustrate certain particular features and/or aspects. These Examples should not be construed to limit the disclosure to the particular features or aspects described.

Example 1: Plant Material and DNA Extraction

For fine mapping and validation of low fiber content and seed coat color traits from yellow seed coat (YSC) line YN01-429, two dihaploid (DH) populations, YSC and YDN, were developed from crosses between spring canola lines in 2007 and 2010, respectively. The 176 DH lines of YSC population were developed from a cross between the Agriculture and Agri-Food Canada (AAFC) yellow seeded, low fiber line YN01-429 and the DAS Nexera black seeded, high fiber variety Nex828. The 399 DH lines of the YDN population were developed from a cross between YN01-429 and DAS Nexera black seeded, high fiber variety DN051493. The DH population, TN, was derived from a cross between the European winter cultivar Tapidor and the Chinese semi-winter cultivar Ningyou7. This population was a reference mapping population widely used for trait mapping and genomics studies by the international canola research community (Shi et al. 2009), and was not segregating for fiber content and seed coat color traits. It was used for consensus map construction along with the YSC and YDN populations to identify more Single Nucleotide Polymorphic (SNP) markers tightly linked to the fiber content and seed coat color traits.

Genomic DNA for the populations was extracted from 8 leaf punches per sample using the DAS Biocel extraction method (Bohl et al. 2009). DNA samples were quantified with Quant-iT™ PicoGreen® Quantification Kit (Invitrogen, Carlsbad, Calif.) using the manufacturer's instructions or with the Nanodrop 8000 Spectrophotometer (Thermo Scientific, Waltham, Mass.) per manufacturer's instructions.

Example 2: Phenotypic Data

The 176 DH lines from the YSC population were grown along with the two parents as checks in paired row plots at the AAFC Saskatoon research farm and the DAS Rosthern research farm at Canada in 2007 for phenotyping. Seed samples from all established plots were collected from both locations and analyzed by AAFC using Near Infrared Spectroscopy (NIR) for Acid Detergent Fiber (ADF) and seed coat color White Index (WI). The population was also analyzed for ADF using the AOAC reference method (AOAC Official Method 973.18) in 2007 and for seed coat color White Index and Hunter Lab Lightness Index (L) in 2011.

The YDN population was grown along with the two parents as checks in paired row plots at Pike Lake and Cudworth, Canada in 2011 for phenotyping. Seed samples from 361 DH lines were analyzed for ADF using two NIR models and for seed coat color White Index and the HunterLab Lightness Index in 2011.

Significant differences were observed between the two mapping parents for fiber content and seed coat color for both populations, as illustrated in Table 1. Distributions of fiber content in DH lines revealed bi-modal distributions skewed towards the higher fiber range in both populations (FIGS. 1 and 2). High correlation was observed between the seed coat color traits WI and L ($R^2$=0.81-0.99) and between seed coat color traits and fiber content traits ($R^2$=0.66-0.85) in both populations (FIGS. 1 and 2).

TABLE 1

The % ADF and seed coat color data, WI and L of the parents and DH lines in YSC and YDN populations.

| | YSC population | | | | YDN population | | | |
|---|---|---|---|---|---|---|---|---|
| Trait | Nex828 | YN01-429 | DH lines with Nex828 alleles | DH lines with YN01-429 alleles | DN051493 | YN01-429 | DH lines with DN051493 alleles | DH lines with YN01-429 alleles |
| % ADF | 15.6% | 9.1% | 14.0 ± 1.6% | 10.0 ± 1.0% | 19.0% | 12.6% | 18.5 ± 1.4% | 12.8 ± 0.9% |
| WI | 68.0 | 145.6 | 67.1 ± 4.2 | 100.4 ± 19.2 | 67.9 | 159.3 | 68.0 ± 5.0 | 123.5 ± 19.6 |
| L | 74.4 | 157.7 | 73.1 ± 5.0 | 109.9 ± 20.8 | 74.4 | 172.1 | 74.1 ± 5.9 | 134.8 ± 20.8 |

Example 3: Genotypic Data

The three DH populations, YSC, YDN, and TN, were genotyped with 12,000 SNP markers developed at DAS on two Illumina Infinium chips on the BeadStation 500 G per manufacturer's protocol (Illumina, San Diego, Calif.). Genotypic data was analyzed using the GenomeStudio Genotyping Analysis Module v1.8.4 (Illumina, San Diego, Calif.), which converts fluorescent signals for each SNP into A and B signals whose values reflect the relative abundance of arbitrarily assigned A and B alleles. Signal is converted into polar coordinates, using the Manhattan distance metric for the intensity R, and with Theta∈[0,1] representing angle ∈[0,90] degrees. Each marker is clustered in Cartesian coordinates, and the genotypes {AA, AB, BB} are assigned to samples in clusters close to Theta-{0, ½, 1}.

Example 4: Linkage Map and Consensus Map Construction

The individual maps of the YSC, YDN and TN populations were constructed with MAPMAKER/EXP 3.0 (Lander et al. 1987; Lincoln et al. 1992) at LOD score 10.0 and Haldane's mapping function, and the consensus map was constructed with Phenomap Enterprise 3.0 (GeneFlow Inc., Centreville, Va.).

The YSC genetic map was constructed with 176 DH lines and 2,982 polymorphic SNP markers, and had a total length of 2,515.8 cM and an average length of 0.80 cM/marker. The YDN genetic map was constructed with 399 DH lines and 2,972 SNP markers, and had a total length of 2,189 cM and an average of 0.74 cM/marker. The TN genetic map was constructed with 181 DH lines and 2,716 polymorphic SNP markers, and had a total length of 1905.7 cM and an average of 0.70 cM/marker. A consensus map of 5,500 SNP markers was constructed with the YDN, YSC and TN populations.

Example 5: QTL Mapping

The Composite Interval Mapping (CIM), as implemented in QTL Cartographer V2.5 (Wang et al. 2011), was used for QTL mapping. A LOD score of 3.0 was used as threshold to identify genomic regions significantly affecting the seed coat color and fiber content traits.

TABLE 2

The phenotypic variance explained (R2) by significant QTL underlying ADF content and seed coat color traits (WI and L) in YSC and YDN populations with LOD scores ≥3.

| Population | Trait | Linkage Group | % of Variance Explained ($R^2$) | LOD |
|---|---|---|---|---|
| YSC (n = 176) | Seed coat color_L | N09 | 60.8 | 41 |
| | Seed coat color_WI | N09 | 59.2 | 40 |
| | Fiber content_ADF | N09 | 71.5 | 47 |
| | Seed coat color_L | N11 | 6.3 | 8 |
| | Seed coat color_WI | N11 | 7.2 | 9 |
| | Fiber content_ADF | N11 | 2.4 | 3 |
| YDN (n = 399) | Seed coat color_L | N09 | 74.7 | 143 |
| | Seed coat color_WI | N09 | 74 | 141 |
| | Fiber content_ADF | N09 | 73.4 | 136 |
| | Seed coat color_L | N11 | 5.7 | 26 |
| | Seed coat color_WI | N11 | 5.9 | 26 |
| | Fiber content_ADF | N11 | 1.4 | 7 |

Example 6: Mapping of ADF and Seed Coat Color as Qualitative Traits

Because of the large effect of the major QTL ($R^2$=59.2/6-74.7%) on N09, and the bi-modal distributions of fiber content and seed coat color traits in the DH lines (FIGS. 1 and 2), quantitative fiber content and seed coat color traits can be treated as qualitative traits. Based on their ADF content and seed coat color WI, DH lines of both populations were divided into two groups, one with low fiber/high WI and homozygous YN01-429 alleles and the other group with high fiber/low WI and homozygous Nex828 or DN051493 alleles (FIGS. 1 and 2).

Example 7: Fine-mapping of the Major QTL on N09

The YDN population was later used for fine mapping and validation of the major QTL on N09. A new genetic map of N09 was constructed with 1387 SNPs. Flanking markers DBSNP01120 and DBSNP02172 defined a QTL interval of 4.9 cM, corresponding to 0.46 Mb on the *B. napus* reference genome, DH12075, which was sequenced at AAFC through an industry consortium. The major QTL has an $R^2$ of 75% on N09. Blind screenings of the markers within the QTL interval with multiple DAS proprietary DH populations from the breeding program confirmed that the concordance between marker-predicated phenotype and actual phenotype was ≥98%. FIG. 3 shows the genetic map of the ADF QTL interval along with the ADF_09 and WI_09 loci.

Within the 4.9 cM QTL interval on N09, 111 SNP markers were identified, including the flanking markers DBSNP01120 and DBSNP02172. Table 3 lists the SNPs, their genetic positions in cM, the YN01-429 allele as well as the physical positions of the SNPs on the *B. napus* reference genome (DH12075).

TABLE 3

SNP markers within the 4.9 cM QTL interval for ADF mapped on N09 with the YDN population.

| SNP_Name | SEQ ID NO: | Map Position (cM) | SNP_ Type | SNP_ Forward | YN01429 genotype | Physical Pos on Ref Genome (bp) |
|---|---|---|---|---|---|---|
| DBSNP01120 | 1 | 117.4 | SNP | [T/G] | GG | N9:35982462..35983088 |
| DBSNP357202 | 2 | 117.4 | SNP | [C/G] | GG | N9:35982582..35984072 |
| DBSNP357203 | 3 | 117.4 | SNP | [T/G] | TT | N9:35982826..35984316 |

TABLE 3-continued

SNP markers within the 4.9 cM QTL interval for ADF mapped on N09 with the YDN population.

| SNP_Name | SEQ ID NO: | Map Position (cM) | SNP_ Type | SNP_ Forward | YN01429 genotype | Physical Pos on Ref Genome (bp) |
|---|---|---|---|---|---|---|
| DBSNP222203 | 4 | 117.4 | SNP | [A/C] | AC | N9:35987647..35987947 |
| DBSNP357208 | 5 | 117.4 | SNP | [T/G] | GG | N9:35994219..35995219 |
| DBSNP357214 | 6 | 117.7 | SNP | [A/G] | AA | N9:36025967..36026963 |
| DBSNP222206 | 7 | 117.7 | SNP | [A/G] | AA | N9:36027874..36028174 |
| DBSNP357215 | 8 | 118.2Q | INDEL | [-/A] | AA | N9:36030593..36031612 |
| DBSNP357216 | 9 | 118.2Q | SNP | [T/G] | TG | N9:36030597..36031616 |
| DBSNP357217 | 10 | 118.2Q | INDEL | [+/ATCAC GCACCTG CAAATGT] | ATCACGC ACCTGCA AATGT | N9:36030617..36031636 |
| DBSNP357218 | 11 | 118.2Q | SNP | [A/G] | GG | N9:36030736..36031756 |
| DBSNP357219 | 12 | 118.7 | SNP | [A/G] | GG | N9:36030916..36031808 |
| DBSNP357221 | 13 | 119 | SNP | [C/G] | CC | N9:36038430..36039006 |
| DBSNP357222 | 14 | 119 | SNP | [T/G] | TT | N9:36038430..36039335 |
| DBSNP357223 | 15 | 119 | SNP | [A/G] | GG | N9:36038516..36039516 |
| DBSNP357224 | 16 | 119 | SNP | [T/C] | CC | N9:36038712..36039712 |
| DBSNP222208 | 17 | 119 | SNP | [T/C] | CC | N9:36039152..36039272 |
| DBSNP357226 | 18 | 119 | SNP | [C/G] | GG | N9:36039465..36040465 |
| DBSNP357227 | 19 | 119 | SNP | [A/C] | CC | N9:36039710..36040708 |
| DBSNP357228 | 20 | 119 | SNP | [T/C] | CC | N9:36039738..36040726 |
| DBSNP357229 | 21 | 119.3 | SNP | [T/G] | GG | N9:36040629..36041743 |
| DBSNP357230 | 22 | 119.8 | SNP | [T/C] | CC | N9:36041302..36042269 |
| DBSNP357231 | 23 | 119.8 | SNP | [A/G] | AA | N9:36041326..36042293 |
| DBSNP357232 | 24 | 119.8 | SNP | [T/C] | CC | N9:36041431..36042398 |
| DBSNP357233 | 25 | 119.8 | SNP | [T/C] | CC | N9:36041470..36042437 |
| DBSNP357234 | 26 | 119.8 | SNP | [T/C] | CC | N9:36041587..36042554 |
| DBSNP357235 | 27 | 119.8 | SNP | [A/T] | AA | N9:36042193..36043188 |
| DBSNP357236 | 28 | 119.8 | INDEL | [+/TT] | TT | N9:36042318..36043314 |
| DBSNP357237 | 29 | 119.8 | SNP | [T/C] | TT | N9:36042320..36043316 |
| DBSNP357238 | 30 | 119.8 | SNP | [A/T] | TT | N9:36042626..36043621 |
| DBSNP357239 | 31 | 119.8 | SNP | [T/C] | TT | N9:36042629..36043624 |
| DBSNP357240 | 32 | 119.8 | INDEL | [+/A] | + | N9:36042765..36043760 |
| DBSNP357241 | 33 | 119.8 | SNP | [A/G] | AG | N9:36043110..36044110 |
| DBSNP357242 | 34 | 119.8 | INDEL | [-/T] | T | N9:36043117..36044117 |
| DBSNP357244 | 35 | 119.8 | SNP | [T/C] | TT | N9:36043219..36044219 |
| DBSNP357245 | 36 | 119.8 | SNP | [T/C] | CC | N9:36043480..36044475 |
| DBSNP357246 | 37 | 119.8 | SNP | [A/T] | TT | N9:36044691..36045691 |
| DBSNP357247 | 38 | 119.8 | SNP | [A/T] | TT | N9:36045200..36046200 |

TABLE 3-continued

SNP markers within the 4.9 cM QTL interval for ADF mapped on N09 with the YDN population.

| SNP_Name | SEQ ID NO: | Map Position (cM) | SNP_ Type | SNP_ Forward | YN01429 genotype | Physical Pos on Ref Genome (bp) |
|---|---|---|---|---|---|---|
| DBSNP04324 | 39 | 119.8 | SNP | [T/C] | CC | N9:36046568..36047839 |
| DBSNP357249 | 40 | 119.8 | SNP | [A/G] | AA | N9:36046761..36047762 |
| DBSNP357250 | 41 | 119.8 | SNP | [A/G] | AA | N9:36046762..36047763 |
| DBSNP357251 | 42 | 119.8 | SNP | [A/G] | AA | N9:36046778..36047779 |
| DBSNP357252 | 43 | 119.8 | SNP | [A/G] | GG | N9:36046868..36047869 |
| DBSNP357253 | 44 | 119.8 | SNP | [A/G] | GG | N9:36046920..36047921 |
| DBSNP357254 | 45 | 119.8 | INDEL | [+/T] | + | N9:36047652..36048534 |
| DBSNP357255 | 46 | 119.8 | SNP | [T/C] | TT | N9:36047710..36048534 |
| DBSNP357256 | 47 | 119.8 | SNP | [A/G] | GG | N9:36047752..36048534 |
| DBSNP357257 | 48 | 119.8 | SNP | [T/C] | CC | N9:36047876..36048534 |
| DBSNP357258 | 49 | 119.8 | SNP | [A/G] | AA | N9:36047941..36048534 |
| DBSNP357259 | 50 | 119.8 | SNP | [T/C] | TT | N9:36048002..36048534 |
| DBSNP357260 | 51 | 119.8 | SNP | [C/G] | GG | N9:36048012..36048534 |
| DBSNP357262 | 52 | 119.8 | INDEL | [+/A] | + | N9:36048530..36049322 |
| DBSNP357263 | 53 | 119.8 | SNP | [A/T] | TT | N9:36048530..36049347 |
| DBSNP357264 | 54 | 119.8 | SNP | [A/T] | TT | N9:36048530..36049442 |
| DBSNP357265 | 55 | 119.8 | SNP | [A/G] | AG | N9:36048530..36049520 |
| DBSNP357266 | 56 | 119.8 | SNP | [A/G] | AA | N9:36048564..36049565 |
| DBSNP357267 | 57 | 119.8 | SNP | [C/G] | CG | N9:36048641..36049642 |
| DBSNP357268 | 58 | 119.8 | SNP | [A/C] | CC | N9:36048645..36049646 |
| DBSNP357269 | 59 | 119.8 | SNP | [T/C] | TC | N9:36048651..36049652 |
| DBSNP357270 | 60 | 119.8 | SNP | [C/G] | CC | N9:36048792..36049793 |
| DBSNP357271 | 61 | 119.8 | SNP | [T/C] | CC | N9:36048794..36049795 |
| DBSNP357272 | 62 | 119.8 | INDEL | [+/A] | + | N9:36048932..36049933 |
| DBSNP357273 | 63 | 119.8 | SNP | [A/T] | TT | N9:36048985..36049986 |
| DBSNP357274 | 64 | 119.8 | SNP | [A/G] | AG | N9:36049082..36050083 |
| DBSNP357275 | 65 | 119.8 | SNP | [T/C] | TC | N9:36049455..36050457 |
| DBSNP357276 | 66 | 119.8 | SNP | [A/G] | AA | N9:36049482..36050484 |
| DBSNP357278 | 67 | 119.8 | SNP | [C/G] | CC | N9:36049554..36050556 |
| DBSNP357280 | 68 | 119.8 | SNP | [T/G] | TT | N9:36049653..36050643 |
| DBSNP357282 | 69 | 119.8 | SNP | [T/G] | TT | N9:36049758..36050643 |
| DBSNP357286 | 70 | 119.8 | SNP | [A/G] | AA | N9:36054018..36055018 |
| DBSNP222210 | 71 | 119.8 | SNP | [A/G] | AG | N9:36054461..36054578 |
| DBSNP357287 | 72 | 119.8 | SNP | [A/T] | TT | N9:36054757..36055757 |
| DBSNP357288 | 73 | 119.8 | SNP | [A/G] | GG | N9:36054789..36055789 |
| DBSNP357289 | 74 | 119.8 | SNP | [T/C] | CC | N9:36054810..36055810 |
| DBSNP357290 | 75 | 119.8 | SNP | [A/G] | AA | N9:36054813..36055813 |

TABLE 3-continued

SNP markers within the 4.9 cM QTL interval for ADF mapped on N09 with the YDN population.

| SNP_Name | SEQ ID NO: | Map Position (cM) | SNP_ Type | SNP_ Forward | YN01429 genotype | Physical Pos on Ref Genome (bp) |
|---|---|---|---|---|---|---|
| DBSNP357291 | 76 | 119.8 | SNP | [A/C] | AA | N9:36054956..36055956 |
| DBSNP357292 | 77 | 119.8 | SNP | [C/G] | CC | N9:36054966..36055966 |
| DBSNP357293 | 78 | 119.8 | SNP | [T/C] | TT | N9:36054983..36055983 |
| DBSNP357294 | 79 | 119.8 | SNP | [T/C] | TT | N9:36055008..36056008 |
| DBSNP84508 | 80 | 119.8 | SNP | [A/C] | AC | N9:36055121..36055879 |
| DBSNP222211 | 81 | 119.8 | SNP | [A/G] | GG | N9:36060768..36060968 |
| DBSNP222212 | 82 | 119.8 | SNP | [A/G] | GG | N9:36061805..36061924 |
| DBSNP222214 | 83 | 119.8 | SNP | [A/G] | AA | N9:36076182..36076301 |
| DBSNP222219 | 84 | 119.8 | SNP (dominant) | [T/G] | - | N9:36096659..36096732 |
| DBSNP222220 | 85 | 119.8 | SNP (dominant) | [A/C] | - | N9:36096733..36096814 |
| DBSNP240715 | 86 | 119.8 | SNP | [A/G] | AG | N9:36100799..36100917 |
| DBSNP222222 | 87 | 119.8 | SNP | [A/G] | GG | N9:36119793..36119830 |
| DBSNP38295 | 88 | 119.8 | SNP | [A/G] | GG | N9:36132536..36133536 |
| DBSNP222225 | 89 | 119.8 | SNP | [A/G] | GG | N9:36132936..36133136 |
| DBSNP222226 | 90 | 119.8 | SNP | [A/G] | AA | N9:36136254..36136558 |
| DBSNP08212 | 91 | 119.8 | SNP | [A/G] | AA | N9:36143105..36143329 |
| DBSNP08214 | 92 | 119.8 | SNP | [T/G] | TT | N9:36143105..36143329 |
| DBSNP222228 | 93 | 119.8 | SNP | [T/C] | CC | N9:36147820..36147940 |
| DBSNP222229 | 94 | 120.1 | SNP | [A/G] | AA | N9:36156553..36156673 |
| DBSNP42126 | 95 | 120.1 | SNP | [T/G] | GG | N9:36157370..36158339 |
| DBSNP222231 | 96 | 120.1 | SNP | [T/C] | TT | N9:36165969..36166169 |
| DBSNP222233 | 97 | 120.6 | SNP | [A/G] | AA | N9:36175905..36176121 |
| DBSNP222235 | 98 | 120.6 | SNP | [A/G] | AA | N9:36190213..36190333 |
| DBSNP146598 | 99 | 120.6 | SNP | [T/C] | TC | N9:36207823..36208597 |
| DBSNP147032 | 100 | 120.6 | SNP | [A/G] | AG | N9:36212362..36213110 |
| DBSNP94819 | 101 | 120.6 | SNP | [T/G] | TG | N9:36213988..36214561 |
| DBSNP158066 | 102 | 120.6 | SNP | [A/T] | TA | N9:36214885..36215409 |
| DBSNP158078 | 103 | 120.6 | SNP | [T/C] | CC | N9:36214926..36215606 |
| DBSNP63288 | 104 | 121.4 | SNP | [T/G] | TG | N9:36278558..36279063 |
| DBSNP52362 | 105 | 121.4 | SNP | [T/C] | + | N9:36279239..36280186 |
| DBSNP222241 | 106 | 121.4 | SNP | [T/C] | - | N9:36291810..36291930 |
| DBSNP222242 | 107 | 121.4 | SNP | [T/C] | TT | N9:36308543..36308663 |
| DBSNP189108 | 108 | 121.4 | SNP | [T/C] | TC | N9:36308946..36309355 |
| DBSNP222244 | 109 | 121.7 | SNP | [T/C] | CC | N9:36353147..36353447 |

TABLE 3-continued

SNP markers within the 4.9 cM QTL interval for ADF mapped on N09 with the YDN population.

| SNP_Name | SEQ ID NO: | Map Position (cM) | SNP_ Type | SNP_ Forward | YN01429 genotype | Physical Pos on Ref Genome (bp) |
|---|---|---|---|---|---|---|
| DBSNP222246 | 110 | 122 | SNP | [T/G] | TT | N9:36372163..36372403 |
| DBSNP02172 | 111 | 122.3 | SNP | [C/G] | CC | N9:36447139..36448664 |

Within the 4.9 cm ADF QTL interval, flanked by DBSNP01120 and DBSNP02172, a sub-interval was defined in which the markers are most desired for marker assisted selection. Flanking markers DBSNP35722 and DBSNP222211 define a 0.5 cM sub-interval haplotype region unique to the donor YN01-429. The DBSNP35722 and DBSNP222211 flanking markers and the markers within the sub-interval can be used for marker assisted selection to track the QTL on N09 when breeding for enhanced ACM attributes.

We claim:

1. A method for producing meal from *Brassica napus* plants having low acid detergent fiber desirable nutritional value, the method comprising:

providing a population *Brassica napus* plants from *Brassica napus* line YN01-429 or its lineage or *Brassica napus* line YN97-262 or its lineage;

using marker assisted selection to analyze the population of plants or seeds thereof for the presence of at least one N09 marker allele at a locus within N09 chromosomal interval comprising and flanked by SEQ ID NO:1 and SEQ ID NO:111 associated with low acid detergent fiber;

selecting at least one plant or seeds thereof having the N09 marker allele; and producing meal having low acid detergent fiber from seeds of the selected plant or the selected seeds.

2. The method according to claim 1, wherein the selected plant seeds have lower acid detergent fiber content relative to seeds from plants in the population that do not have the N09 marker allele.

3. The method according to claim 1, wherein the selected plant seeds thereof have higher protein content relative to seeds from plants in the population that do not have the N09 marker allele.

4. The method according to claim 1, wherein the selected plant seeds have higher protein content relative to seeds from plants in the population that do not have the N09 marker allele.

5. The method according to claim 1, wherein the selected plant seeds have lower fiber and higher protein content relative to seeds from plants in the population that do not have the N09 marker allele.

6. The method according to claim 1, wherein the selected plant seeds have less than 15% acid detergent fiber content.

7. The method according to claim 1, wherein the selected plant seeds have at least 44% crude protein content.

8. The method according to claim 1, wherein the selected plant seeds have at least 49% crude protein content.

9. The method according to claim 1, wherein the population includes plants from the lineage of *Brassica napus* line YN01-429.

10. The method according to claim 1, wherein the population includes plants from the lineage of *Brassica napus* line YN97-262.

11. The method according to claim 1, wherein the at least one marker alleles are at a locus comprising and flanked by SEQ ID NO:14 and SEQ ID NO:81.

12. The method according to claim 1, wherein the at least one marker allele is a single-nucleotide polymorphism (SNP).

13. The method according to claim 1, wherein the at least one marker allele is a thymine (T) at position 501 of SEQ ID NO:14, a guanine (G) at position 501 of SEQ ID NO:15, a cytosine (C) at position 501 of SEQ ID NO:16, a C at position 61 of SEQ ID NO:17, a G at position 501 of SEQ ID NO:18, a C at position 501 of SEQ ID NO:19, a C at position 501 of SEQ ID NO:20, a G at position 501 of SEQ ID NO:21, a C at position 501 of SEQ ID NO:22, an adenine (A) at position 501 of SEQ ID NO:23, a C at position 501 of SEQ ID NO:24, a C at position 501 of SEQ ID NO:25, a C at position 501 of SEQ ID NO:26, an A at position 501 of SEQ ID NO:27, a TT at position 502 of SEQ ID NO:28, a T at position 501 of SEQ ID NO:29, a T at position 501 of SEQ ID NO:30, a T at position 501 of SEQ ID NO:31, a T at position 502 of SEQ ID NO:32, a T at position 501 of SEQ ID NO:34, a T at position 501 of SEQ ID NO:35, a C at position 501 of SEQ ID NO:36, a T at position 501 of SEQ ID NO:37, a T at position 501 of SEQ ID NO:38, a C at position 536 of SEQ ID NO:39, an A at position 501 of SEQ ID NO:40, an A at position 501 of SEQ ID NO:41, an A at position 501 of SEQ ID NO:42, a G at position 501 of SEQ ID NO:43, a G at position 501 of SEQ ID NO:44, an A at position 502 of SEQ ID NO:45, a T at position 501 of SEQ ID NO:46, a G at position 501 of SEQ ID NO:47, a C at position 501 of SEQ ID NO:48, an A at position 501 of SEQ ID NO:49, a T at position 501 of SEQ ID NO:50, a G at position 501 of SEQ ID NO:51, a C at position 502 of SEQ ID NO:52, a T at position 501 of SEQ ID NO:53, a T at position 501 of SEQ ID NO:54, an A at position 501 of SEQ ID NO:56, a C at position 501 of SEQ ID NO:58, a C at position 501 of SEQ ID NO:60, a C at position 501 of SEQ ID NO:61, a C at position 502 of SEQ ID NO:62, a T at position 501 of SEQ ID NO:63, an A at position 501 of SEQ ID NO:66, a C at position 501 of SEQ ID NO:67, a T at position 501 of SEQ ID NO:68, a T at position 501 of SEQ ID NO:69, an A at position 501 of SEQ ID NO:70, a T at position 501 of SEQ ID NO:72, a G at position 501 of SEQ ID NO:73, a C at position 501 of SEQ ID NO:74, an A at position 501 of SEQ ID NO:75, an A at position 501 of SEQ ID NO:76, a C at position 501 of SEQ ID NO:77, a Tat position 501 of SEQ ID NO:78, a T at position 501 of SEQ ID NO:79, or a G at position 101 of SEQ ID NO:81.

14. The method according to claim 13, wherein the population includes plants from the lineage of *Brassica napus* line YN01-429.

15. The method according to claim 13, wherein the population includes plants from the lineage of *Brassica napus* line YN97-262.

16. The method according to claim 1, wherein the marker alleles are selected from the group consisting of a guanine (G) at position 283 of SEQ ID NO:1, a guanine (G) at position 501 of SEQ ID NO:2, a thymine (T) at position 501 of SEQ ID NO:3, a G at position 501 of SEQ ID NO:5, an adenine (A) at position 501 of SEQ ID NO:6, an A at position 151 of SEQ ID NO:7, an A at position 501 of SEQ ID NO:8, a 19 nucleotide insertion at position 502 of SEQ ID NO:10, a G at position 501 of SEQ ID NO:11, a G at position 501 of SEQ ID NO:12, a cytosine (C) at position 501 of SEQ ID NO:13, a G at position 61 of SEQ ID NO:82, an A at position 61 of SEQ ID NO:83, a G at position 61 of SEQ ID NO:87, a G at position 501 of SEQ ID NO:88, a G at position 101 of SEQ ID NO: 89, an A at position 151 of SEQ ID NO:90, an A at position 153 of SEQ ID NO:91, a T at position 48 of SEQ ID NO:92, a C at position 61 of SEQ ID NO:93, an A at position 61 of SEQ ID NO:94, a G at position 501 of SEQ ID NO:95, a T at position 101 of SEQ ID NO:96, an A at position 151 of SEQ ID NO:97, an A at position 61 of SEQ ID NO:98, a C at position 328 of SEQ ID NO:103, a Tat position 61 of SEQ ID NO:107, a C at position 151 of SEQ ID NO:109, a Tat position 151 of SEQ ID NO:110, and a C at position 848 of SEQ ID NO:111.

17. The method according to claim 16, wherein the population includes plants from the lineage of *Brassica napus* line YN01-429.

18. The method according to claim 16, wherein the population includes plants from the lineage of *Brassica napus* line YN97-262.

* * * * *

SEQUENCE LISTING

```
<160> NUMBER OF SEQ ID NOS: 111

<210> SEQ ID NO 1
<211> LENGTH: 532
<212> TYPE: DNA
<213> ORGANISM: Brassica napus
<220> FEATURE:
<221> NAME/KEY: misc_feature
<222> LOCATION: (295)..(295)
<223> OTHER INFORMATION: where n is a, t, c, or g
<220> FEATURE:
<221> NAME/KEY: misc_feature
<222> LOCATION: (369)..(369)
<223> OTHER INFORMATION: where n is a, t, c, or g
<220> FEATURE:
<221> NAME/KEY: misc_feature
<222> LOCATION: (441)..(441)
<223> OTHER INFORMATION: where n is a, t, c, or g
<220> FEATURE:
<221> NAME/KEY: misc_feature
<222> LOCATION: (452)..(452)
<223> OTHER INFORMATION: where n is a, t, c, or g
<220> FEATURE:
<221> NAME/KEY: misc_feature
<222> LOCATION: (473)..(473)
<223> OTHER INFORMATION: where n is a, t, c, or g

<400> SEQUENCE: 1

gaatttccgg gtcgacatca tcgaggccgg gttccccgcc gcgtccaaag acgacttcga     60

ggcggtcaag accatttccg aaaccgtcgg aaacgccgtc gacgagaacg gttacgtccc    120

cgtcatctgc ggtctctcga ggtgcaacga gagagatatc cagacggctt gggaggctgt    180

gagatacgcc aaaaggccta ggatccatac gttcatcgcc acgagtgata ttcacttgga    240

gtataagctc aagaagagta aacaagaagt catcgagatc gckaggagca tggtntaggt    300

tcgctaggag cttggggtgt gatgacgtgg agtttagtcc tgaagatgca ggaaggtcgg    360

agagagagnt ttttgtatga gattcttgga gaagtgataa aagctggagc gacgacactt    420

aatattcctg atactgttgg ntatcacttt gncctagtga gtttggtcag ttngattgct    480

gatataaagg ctaatacccc tgggattgag aacgttgtca tctcgactca tt            532


<210> SEQ ID NO 2
<211> LENGTH: 1001
<212> TYPE: DNA
<213> ORGANISM: Brassica napus

<400> SEQUENCE: 2
```

```
ctccagcttt tatcacttct ccaagaatct catacaaaaa ctctctctcc gacctgttaa     60
acaaattaaa ataaatataa acagttacag agaaagtgaa agcttggtaa tcaagattag    120
aactaattaa aataaataaa agataattaa accccccacc ttcctgcatc ttcaggacta    180
aactccacgt catcacaccc caagctccta gcgaacctaa ccatgctcct cgcgatctcg    240
atgacttctt gtttactctt cttgagctta tactccaagt gaatatcact cgtggcgatg    300
aacgtatgga tcctaggcct tttggcgtat ctcacagcct cccaagccgt ctggatatct    360
ctctcgttgc acctcgagag accgcagatg acggggacgt aaccgttctc gtcgacggcg    420
tttccgacgg tttcggaaat ggtcttgacc gcctcgaagt cgtctttgga cgcggcgggg    480
aacccggcct cgatgatgtc sacgccgagc ttcgcgagct gccgcgcgat gtcgagcttc    540
tccttggagg tgagggtggc gccgggggac tgctcgccgt cgcggagcgt ggtgtcgaag    600
atgcggacgt agttggggtc ggaaatgcgg ttggggatgt agtccgggcg gcggcggcgg    660
agggggtggg gagggagagg gggcggtgga tctgagatgg agcaggagag gcggagggag    720
gcggaggagg agcggcggcg gtggtgggat ggtgggaaac ggaaggagag tggtgtggtg    780
attgttgtgg agaaggtggg gagagaaggt gttgttgttg atgatgagag tgaagggttt    840
ctgagaaggg aagacgccat tggagacgat tgtgagaaga atggtaaacc taaagagaga    900
gagagatgaa ggtttgaacg tggcggcggc agctacttgg ttaagctcta tctgttcgtt    960
cgtgtcactc ttctctttat ttgacaaaaa caaatctttt t                       1001
```

```
<210> SEQ ID NO 3
<211> LENGTH: 1001
<212> TYPE: DNA
<213> ORGANISM: Brassica napus

<400> SEQUENCE: 3

cttcttgttt actcttcttg agcttatact ccaagtgaat atcactcgtg gcgatgaacg     60
tatggatcct aggccttttg gcgtatctca cagcctccca agccgtctgg atatctctct    120
cgttgcacct cgagagaccg cagatgacgg ggacgtaacc gttctcgtcg acggcgtttc    180
cgacggtttc ggaaatggtc ttgaccgcct cgaagtcgtc tttggacgcg gcggggaacc    240
cggcctcgat gatgtcgacg ccgagcttcg cgagctgccg cgcgatgtcg agcttctcct    300
tggaggtgag ggtggcgccg ggggactgct cgccgtcgcg gagcgtggtg tcgaagatgc    360
ggacgtagtt ggggtcggaa atgcggttgg ggatgtagtc cgggcggcgg cggcggaggg    420
ggtggggagg gagaggggc ggtggatctg agatggagca ggagaggcgg agggaggcgg    480
aggaggagcg gcggcggtgg kgggatggtg ggaaacggaa ggagagtggt gtggtgattg    540
ttgtggagaa ggtggggaga gaaggtgttg ttgttgatga tgagagtgaa gggtttctga    600
gaagggaaga cgccattgga gacgattgtg agaagaatgg taaacctaaa gagagagaga    660
gatgaaggtt tgaacgtggc ggcggcagct acttggttaa gctctatctg ttcgttcgtg    720
tcactcttct ctttatttga caaaaacaaa tctttttttt tggtcccact tgaatattct    780
ccacttaaaa aaatgagtac gacaactgtg ttatacttta aacggcgtcg ttataggata    840
caatagaaaa agtcgaccgg caacgataag gacgatgagt cgattgaaca gtttagaaag    900
gacgtagaac catgagattc accaataagc attgaacaag aagacatgga gatggaaagt    960
tgttaaaaca ttttttaaat gaacttaaca tgtcacattg t                       1001

<210> SEQ ID NO 4
<211> LENGTH: 301
```

<212> TYPE: DNA
<213> ORGANISM: Brassica napus

<400> SEQUENCE: 4

```
caaracattt tcacatatat cacttycatg ctcacytcca ccaaccacaa aaaaatgacg     60

agtactataa agcaagaagg acaaagcata cccaatattt ataaataaat cccaccagct    120

gagtgcatct acatcgcctg agtattaaaa mataaaacaa ggagggccga taagaaggaa    180

gggaacgcaa taacattatc tatgaagata agacttcaga aggcagagag accaagtaag    240

aaaattatgt aggcaagcat tcaagagata caacattacc agtaagctty aggaggataa    300

a                                                                    301
```

<210> SEQ ID NO 5
<211> LENGTH: 1001
<212> TYPE: DNA
<213> ORGANISM: Brassica napus

<400> SEQUENCE: 5

```
tagcatgccc agtagtagca aaagaagtga gcacctaaca cgaaaaaacg ccaaagtcat     60

gctgctttca caagagcagg tagaaaacaa aagaaaaggg aatatacagg attcttagcc    120

atgaacaatg cctggaactt tgtatttttc aaacattagc tctgccgccc tgtcaagcat    180

acaatttgag aacatcagta acacactcaa agatgaacta acataagaca aaagtaaata    240

tctataagca gataaatcag acttctctct atgctgttga gtgtttaaag gaggctcagc    300

tagcagcatg ggctgctcct taggatcaat catcaaacaa ctccttcaga cataaaaaaa    360

catattagag atgacatcaa acaataattt atgagaaaaa actaaagctt tatacagttt    420

acctgaatgc atgttcccat ttttgtttat taaaatattg caaaaataat tgactaaatc    480

ttcatataca aaattttgac kgaaaactgc agctttcatc ttcttcctgg agatttaggt    540

ttatatctcc aattggattg gatttgttct cttgaaggga ttaaaacgaa aaagagggaa    600

aacaaaataa aacgccgttg ccggggatcg aacccgggtc acccgcgtga caggcgtgaa    660

tacttaccac tatactacaa cgactcagtt gattaaagat tcaatcaaaa tatactgaaa    720

taaaaaagtt tacgctttga aatgggagac agagctcaac gtacgcactc acgagattct    780

ccagcctcgc aaccaactcc atcagtagcg aagcgaatca aaatttactg aaataaaaaa    840

aaggttacac tttgaaactt actttctaag taattgacaa tacaatatac aaagaaatgg    900

catattaaag tctctttatc gctgtcttaa tcttcttggt tccactcttg ctccattcag    960

ctagtcagct ctcgcccaag gtccgagttg taacggcccg g                       1001
```

<210> SEQ ID NO 6
<211> LENGTH: 1001
<212> TYPE: DNA
<213> ORGANISM: Brassica napus

<400> SEQUENCE: 6

```
ctttgccttt gtcttattat ttgatcttct ttacagctgt gtacgagtca gctaaacatt     60

gctccgttac tcctctccag tattaaatca tgccaggcca gcgcaagatt gttatttgac    120

tacttttcct tccaattacg ttggattact tcttgatttt agttgtgccg caagatctca    180

gatttctaaa ctctgatgca tcaccttctc ctctattggg tttaaaagag ttaattaacc    240

agaagatcaa acatataatt tggatttgtg tttgttttga ccataaatat gttgaaagca    300

gcgtacatgc tactgctttt atctgggaat ggtgttagct taatatggaa agcgatcatg    360
```

```
attaggagca accttagacc ctatattttc tacacatggc tgaaggtgat atggtacgag    420

ataatataat tctatttatt tgtagttaat acccttctac atatatttga tgcagaatca    480

tcaaaccgta actctcccgc rgtaatttga aggccatgga aagtaatgtt tcttttactc    540

attgtaactt aatcatatgc tcttttcatg ttcgtcacat ctcacaactt aagaaatcgt    600

tgctacagtt cttcactttt ttccttgtgg taaagtatat ttttactatt ctttcataca    660

tctctttgta gttaaagtag caagagaatt atgagtctga tgtaggatac aagaggtatc    720

cccaaagaag attaactgcc caaaaacaca tgatatctac taaccagcct ctaattacca    780

aagtagtatc tttttctaat gcatatatac attgattttt atctatgtag gtttagtcac    840

tatatatata ggaggtgcga ctagccatca tttgaattta ttcccactct cattgcagtt    900

tgatcactgg tcagaaatgg gacggttaca cgatctgatt ggtagtagag gcacgcgcag    960

gggggggggg ggtacactta cagccatagt cggagaagtc t                       1001
```

<210> SEQ ID NO 7
<211> LENGTH: 301
<212> TYPE: DNA
<213> ORGANISM: Brassica napus

<400> SEQUENCE: 7

```
aacatcagca agaaggtaac ttgtacacaa ttgaggttta tgttctggta ctttcggtta     60

ggtttgcact tggtgggcaa gaaattgtgg cttttgacct ggaattagtg tgtcacaata    120

ggcaaacaac ttcagtgacc catcttaaac rtaatgctaa gaagcagtgt atttgtttcg    180

tgcttttgaa gtttgaatat attttttctt tctccttttt attaccacaa actactctta    240

tttcctggtt aaaagataaa acgtatggga agcctggtcg gtcttactga gtcattatgc    300

a                                                                    301
```

<210> SEQ ID NO 8
<211> LENGTH: 1001
<212> TYPE: DNA
<213> ORGANISM: Brassica napus
<220> FEATURE:
<221> NAME/KEY: misc_feature
<222> LOCATION: (501)..(501)
<223> OTHER INFORMATION: where n is an insertion/deletion [-/A]

<400> SEQUENCE: 8

```
caagttcaat gagaagggaa aaaaataaca gcgttaacac accttaaaag tattatcatc     60

aggaaacatc tcaagagcct gacccctggt cacttcaatc ctttcaaatg gatgtccttc    120

ctaagatgtc agaggaataa actcaaagct ttgtaaaaga agcaaagaaa tatactgtaa    180

ggagaaatac agagatatca aaaataaaga tatgacaaga ctgaataaga agcagtactc    240

gagcatcccc tgcttcagtt tcgggaaagt gttgctcgtt taaacccaga tcgccataga    300

atgcatcgta gaagaaaccc tggatagaca accaaacaaa taatagagag gcaagcacaa    360

agacacagac aaaaagaatc gctgcaggct cttagtctta cctcatctct agctttgcag    420

ggtccaacgc acagcttaca accatactcc tgttcgagaa ccatggtcaa tgtttaccac    480

aatcaagacg agataaaaaa ngtgttttta ccagggcgag aatgtgagcg ctagaacgcc    540

agaaagtatc acggcctttg tcgctgtcaa aactgaaaaa ctcaagcgaa caatcagctt    600

ccagtggcct attcatgtcc cagaggacat cgtttaccga agagatcagc gctgagtttg    660

ccaatcccac agaaatttgc ctcgcgattt ctgctggagt cgtctcccat ctcttccctt    720

ctttcacgtt tccaccatct cgaattgtaa ccctaattaa gttcacagca gaacaacatt    780
```

```
actgtagccc tagctacgca aagtatatat cagcatctat tgtgtttact tgatcggctc    840

gtgtggccga gactgaatct ccgcgagctg cttcgcttgg aactcctcga agagcctgat    900

acgcttctcg atgacggctg agagataagc ctcgtccctg ggatgttcat ccgccatcgt    960

tggacttgga ggagcacaga aagtgacgaa aggccaaggg a                       1001
```

<210> SEQ ID NO 9
<211> LENGTH: 1001
<212> TYPE: DNA
<213> ORGANISM: Brassica napus

<400> SEQUENCE: 9

```
ttcaatgaga agggaaaaaa ataacagcgt taacacacct taaaagtatt atcatcagga     60

aacatctcaa gagcctgacc cctggtcact tcaatccttt caaatggatg tccttcctaa    120

gatgtcagag gaataaactc aaagctttgt aaaagaagca aagaaatata ctgtaaggag    180

aaatacagag atatcaaaaa taaagatatg acaagactga ataagaagca gtactcgagc    240

atcccctgct tcagtttcgg gaaagtgttg ctcgtttaaa cccagatcgc catagaatgc    300

atcgtagaag aaaccctgga tagacaacca aacaaataat agagaggcaa gcacaaagac    360

acagacaaaa agaatcgctg caggctctta gtcttacctc atctctagct ttgcagggtc    420

caacgcacag cttacaacca tactcctgtt cgagaaccat ggtcaatgtt taccacaatc    480

aagacgagat aaaaaaagtg kttttaccag ggcgagaatg tgagcgctag aacgccagaa    540

agtatcacgg cctttgtcgc tgtcaaaact gaaaaactca agcgaacaat cagcttccag    600

tggcctattc atgtcccaga ggacatcgtt taccgaagag atcagcgctg agtttgccaa    660

tcccacagaa atttgcctcg cgatttctgc tggagtcgtc tcccatctct tcccttcttt    720

cacgtttcca ccatctcgaa ttgtaaccct aattaagttc acagcagaac aacattactg    780

tagccctagc tacgcaaagt atatatcagc atctattgtg tttacttgat cggctcgtgt    840

ggccgagact gaatctccgc gagctgcttc gcttggaact cctcgaagag cctgatacgc    900

ttctcgatga cggctgagag ataagcctcg tccctgggat gttcatccgc catcgttgga    960

cttggaggag cacagaaagt gacgaaaggc caagggatga t                       1001
```

<210> SEQ ID NO 10
<211> LENGTH: 1020
<212> TYPE: DNA
<213> ORGANISM: Brassica napus
<220> FEATURE:
<221> NAME/KEY: misc_feature
<222> LOCATION: (502)..(520)
<223> OTHER INFORMATION: ATCACGCACCTGCAAATGT is Indel
      (insertion/deletion) marker

<400> SEQUENCE: 10

```
ataacagcgt taacacacct taaaagtatt atcatcagga aacatctcaa gagcctgacc     60

cctggtcact tcaatccttt caaatggatg tccttcctaa gatgtcagag gaataaactc    120

aaagctttgt aaaagaagca aagaaatata ctgtaaggag aaatacagag atatcaaaaa    180

taaagatatg acaagactga ataagaagca gtactcgagc atcccctgct tcagtttcgg    240

gaaagtgttg ctcgtttaaa cccagatcgc catagaatgc atcgtagaag aaaccctgga    300

tagacaacca aacaaataat agagaggcaa gcacaaagac acagacaaaa agaatcgctg    360

caggctctta gtcttacctc atctctagct ttgcagggtc caacgcacag cttacaacca    420

tactcctgtt cgagaaccat ggtcaatgtt taccacaatc aagacgagat aaaaaaagtg    480
```

```
tttttaccag ggcgagaatg tatcacgcac ctgcaaatgt gagcgctaga acgccagaaa    540

gtatcacggc ctttgtcgct gtcaaaactg aaaaactcaa gcgaacaatc agcttccagt    600

ggcctattca tgtcccagag gacatcgttt accgaagaga tcagcgctga gtttgccaat    660

cccacagaaa tttgcctcgc gatttctgct ggagtcgtct cccatctctt cccttctttc    720

acgtttccac catctcgaat tgtaacccta attaagttca cagcagaaca acattactgt    780

agccctagct acgcaaagta tatatcagca tctattgtgt ttacttgatc ggctcgtgtg    840

gccgagactg aatctccgcg agctgcttcg cttggaactc ctcgaagagc ctgatacgct    900

tctcgatgac ggctgagaga taagcctcgt ccctgggatg ttcatccgcc atcgttggac    960

ttggaggagc acagaaagtg acgaaaggcc aagggatgat tttttaaacg acgaatgaga   1020
```

<210> SEQ ID NO 11
<211> LENGTH: 1001
<212> TYPE: DNA
<213> ORGANISM: Brassica napus

<400> SEQUENCE: 11

```
caaagctttg taaaagaagc aaagaaatat actgtaagga gaaatacaga gatatcaaaa     60

ataaagatat gacaagactg aataagaagc agtactcgag catcccctgc ttcagtttcg    120

ggaaagtgtt gctcgtttaa acccagatcg ccatagaatg catcgtagaa gaaaccctgg    180

atagacaacc aaacaaataa tagagaggca agcacaaaga cacagacaaa aagaatcgct    240

gcaggctctt agtcttacct catctctagc tttgcagggt ccaacgcaca gcttacaacc    300

atactcctgt tcgagaacca tggtcaatgt ttaccacaat caagacgaga taaaaaaagt    360

gtttttacca gggcgagaat gtgagcgcta gaacgccaga aagtatcacg gcctttgtcg    420

ctgtcaaaac tgaaaaactc aagcgaacaa tcagcttcca gtggcctatt catgtcccag    480

aggacatcgt ttaccgaaga ratcagcgct gagtttgcca atcccacaga aatttgcctc    540

gcgatttctg ctggagtcgt ctcccatctc ttcccttctt tcacgtttcc accatctcga    600

attgtaaccc taattaagtt cacagcagaa caacattact gtagccctag ctacgcaaag    660

tatatatcag catctattgt gtttacttga tcggctcgtg tggccgagac tgaatctccg    720

cgagctgctt cgcttggaac tcctcgaaga gcctgatacg cttctcgatg acggctgaga    780

gataagcctc gtccctggga tgttcatccg ccatcgttgg acttggagga gcacagaaag    840

tgacgaaagg ccaagggatg attttttaaa cgacgaatga gagcagacgg gacgatttta    900

tgacaccact ttaccaaagt ttttagtatt taagattttt ttcaaaaaaa aaaaaaagaa    960

tttaattaat ttgcctattt tcacagattt aattcctttg c                       1001
```

<210> SEQ ID NO 12
<211> LENGTH: 1001
<212> TYPE: DNA
<213> ORGANISM: Brassica napus

<400> SEQUENCE: 12

```
atagacaacc aaacaaataa tagagaggca agcacaaaga cacagacaaa aagaatcgct     60

gcaggctctt agtcttacct catctctagc tttgcagggt ccaacgcaca gcttacaacc    120

atactcctgt tcgagaacca tggtcaatgt ttaccacaat caagacgaga taaaaaaagt    180

gtttttacca gggcgagaat gtgagcgcta gaacgccaga aagtatcacg gcctttgtcg    240

ctgtcaaaac tgaaaaactc aagcgaacaa tcagcttcca gtggcctatt catgtcccag    300
```

```
aggacatcgt ttaccgaaga gatcagcgct gagtttgcca atcccacaga aatttgcctc    360
gcgatttctg ctggagtcgt ctcccatctc ttcccttctt tcacgtttcc accatctcga    420
attgtaaccc taattaagtt cacagcagaa caacattact gtagccctag ctacgcaaag    480
tatatatcag catctattgt rtttacttga tcggctcgtg tggccgagac tgaatctccg    540
cgagctgctt cgcttggaac tcctcgaaga gcctgatacg cttctcgatg acggctgaga    600
gataagcctc gtccctggga tgttcatccg ccatcgttgg acttggagga gcacagaaag    660
tgacgaaagg ccaagggatg attttttaaa cgacgaatga gagcagacgg gacgatttta    720
tgacaccact ttaccaaagt tttagtatt taagattttt ttcaaaaaaa aaaaaaagaa     780
tttaattaat ttgcctattt tcacagattt aattcctttg ctactacaga tttgttgttt    840
cttttcttta attctaattc atttacatgt atactagatt cgttttccgc gctacgcgcg    900
gattacatga ttcaaatttg ttaatttaca aaaaatttca ctacatttac aatattacta    960
attgtttata aaacatttta aaacacaata attttatagt t                       1001
```

<210> SEQ ID NO 13
<211> LENGTH: 1001
<212> TYPE: DNA
<213> ORGANISM: Brassica napus

<400> SEQUENCE: 13

```
gaagattttt cgaaagaatt ttttcagctt tttttttttt tttttttggg gtttatgggg     60
aattcttctt tggtttcatt tgttttatat tttgattttc aggcgtctga atacctgggt    120
tgttggatta agcttgaaag aaaaagtaaa cttgagaaat aagttaactt ctaatcctac    180
tgagttatgg tttaaaggat tagaaaatat ccgaataaat tatcctaatg aatttaggat    240
taagaaaaag gaaatatgtg ttttctaatg agtttaggaa atttgattta tatataagga    300
gatgcaaggg tgttgcataa cttatgagtt ttgtgattgt gtgagagctt gaggtttttg    360
agtgagtttt cctcaagaga ttaataagag agttattctt attatagagt ttatacaatt    420
cgagattcta tatgggtatg gaatcgctcg tggaactcac cacccagtca ttggcaaatt    480
atctcaaagg caagaatccc stcaccattc gatctttgtg gaaggtggaa ggcgacctca    540
ctgctgagga ggaagctaag gcgttggcga tgggcgtggc gaaattagga cattaagtcc    600
attgatgctc tacaaaatct tatgtgatta ctgaagtctg aagaagtttg tccaagtgtc    660
gtttgtttga agtcaaaaat aaagatgtag caggattatc aagttctgat cattaaaagt    720
cctattataa tttctatgtt tcatcatcac tttgaagttc agttaatcaa aagtacgatt    780
caagaatatt ccagtactgt ttctcgatcc attattacca aaaagtttag ctaattatct    840
tcctggaaac ttcttctgtt ccccccatag agaaagttgt cctgccttta gttccagatt    900
aaataagatg agtatcaagt acccatatgt attttcttcc aaaatataag aacataatat    960
ccaactataa tttaagaaaa aacaaagatt agtggagaac g                       1001
```

<210> SEQ ID NO 14
<211> LENGTH: 1001
<212> TYPE: DNA
<213> ORGANISM: Brassica napus

<400> SEQUENCE: 14

```
tttgtgattg tgtgagagct tgaggttttt gagtgagttt tcctcaagag attaataaga     60
gagttattct tattatagag tttatacaat tcgagattct atatgggtat ggaatcgctc    120
gtggaactca ccacccagtc attggcaaat tatctcaaag gcaagaatcc cctcaccatt    180
```

```
cgatctttgt ggaaggtgga aggcgacctc actgctgagg aggaagctaa ggcgttggcg    240
atgggcgtgg cgaaattagg acattaagtc cattgatgct ctacaaaatc ttatgtgatt    300
actgaagtct gaagaagttt gtccaagtgt cgtttgtttg aagtcaaaaa taaagatgta    360
gcaggattat caagttctga tcattaaaag tcctattata atttctatgt ttcatcatca    420
ctttgaagtt cagttaatca aaagtacgat tcaagaatat tccagtactg tttctcgatc    480
cattattacc aaaaagttta kctaattatc ttcctggaaa cttcttctgt tccccccata    540
gagaaagttg tcctgccttt agttccagat taaataagat gagtatcaag tacccatatg    600
tattttcttc caaaatataa gaacataata tccaactata atttaagaaa aaacaaagat    660
tagtggagaa cgttaaaaaa tactcttata taaaagttta atatatttta tgaatattta    720
aattttagtt ttttttaaaa aaaaagtctc aaaatcaatg acagagaggg tgacattaaa    780
ttaattaatc tttctttatt tggcctgaga tgcatgctgc ttataatagt tagttgcttc    840
cagaggaaac acatattcaa acagacaaga ttagctacga cagttgcctg gtaatatttt    900
ttattttatt aggcttcgtt tggaatgatt attataattt ggtatatgat agagagcttg    960
ggctgtgttc tcacattatt caaggtacat tctttctcac t                       1001
```

<210> SEQ ID NO 15
<211> LENGTH: 1001
<212> TYPE: DNA
<213> ORGANISM: Brassica napus

<400> SEQUENCE: 15

```
gatctttgtg gaaggtggaa ggcgacctca ctgctgagga ggaagctaag gcgttggcga     60
tgggcgtggc gaaattagga cattaagtcc attgatgctc tacaaaatct tatgtgatta    120
ctgaagtctg aagaagtttg tccaagtgtc gtttgtttga agtcaaaaat aaagatgtag    180
caggattatc aagttctgat cattaaaagt cctattataa tttctatgtt tcatcatcac    240
tttgaagttc agttaatcaa aagtacgatt caagaatatt ccagtactgt ttctcgatcc    300
attattacca aaaagtttag ctaattatct tcctggaaac ttcttctgtt ccccccatag    360
agaaagttgt cctgccttta gttccagatt aaataagatg agtatcaagt acccatatgt    420
attttcttcc aaaatataag aacataatat ccaactataa tttaagaaaa aacaaagatt    480
agtggagaac gttaaaaaat rctcttatat aaaagtttaa tatattttat gaatatttaa    540
attttagttt tttttaaaaa aaaagtctca aaatcaatga cagagagggt gacattaaat    600
taattaatct ttctttattt ggcctgagat gcatgctgct tataatagtt agttgcttcc    660
agaggaaaca catattcaaa cagacaagat tagctacgac agttgcctgg taatattttt    720
tattttatta ggcttcgttt ggaatgatta ttataatttg gtatatgata gagagcttgg    780
gctgtgttct cacattattc aaggtacatt ctttctcact ataattttct ttttacgtta    840
aattcaactc aaaaccaatt gctcaagtaa tactaatttc accattaatt ttgcaatatt    900
ttggtagcaa tcgacgagac caattttggg acgaatcggt ttattgatcg tattgcatgg    960
acaccatatt attttaggta aactttcaac gcaaaaccaa t                       1001
```

<210> SEQ ID NO 16
<211> LENGTH: 1001
<212> TYPE: DNA
<213> ORGANISM: Brassica napus

<400> SEQUENCE: 16

```
tgatcattaa aagtcctatt ataatttcta tgtttcatca tcactttgaa gttcagttaa     60
tcaaaagtac gattcaagaa tattccagta ctgtttctcg atccattatt accaaaaagt    120
ttagctaatt atcttcctgg aaacttcttc tgttcccccc atagagaaag ttgtcctgcc    180
tttagttcca gattaaataa gatgagtatc aagtacccat atgtattttc ttccaaaata    240
taagaacata atatccaact ataatttaag aaaaaacaaa gattagtgga gaacgttaaa    300
aaatactctt atataaaagt ttaatatatt ttatgaatat ttaaatttta gttttttttta    360
aaaaaaaagt ctcaaaatca atgacagaga gggtgacatt aaattaatta atctttcttt    420
atttggcctg agatgcatgc tgcttataat agttagttgc ttccagagga aacacatatt    480
caaacagaca agattagcta ygacagttgc ctggtaatat tttttatttt attaggcttc    540
gtttggaatg attattataa tttggtatat gatagagagc ttgggctgtg ttctcacatt    600
attcaaggta cattctttct cactataatt ttctttttac gttaaattca actcaaaacc    660
aattgctcaa gtaatactaa tttcaccatt aattttgcaa tattttggta gcaatcgacg    720
agaccaattt tgggacgaat cggtttattg atcgtattgc atggacacca tattatttta    780
ggtaaacttt caacgcaaaa ccaatagacc ttaatgataa atcgtttcaa acttttgatt    840
taacttttca tttcagtgca aacgttatcg cttttagatt ccttgttaaa ctttcaggca    900
aataaactgg aagcagactc aaaacgataa ggaaagagct cgaagaacca actgaagtgg    960
aaagtgaact gaaacgaaga cttgaccagc taactaatca t                       1001
```

<210> SEQ ID NO 17
<211> LENGTH: 121
<212> TYPE: DNA
<213> ORGANISM: Brassica napus

<400> SEQUENCE: 17

```
tgcttataat agttagttgc ttccagaggr aacacatatt caaacagaca agattagcta     60
ygacagttgc ctggtaatat tttttatttt attaggcttc gtttggaatg attattataa    120
t                                                                   121
```

<210> SEQ ID NO 18
<211> LENGTH: 1001
<212> TYPE: DNA
<213> ORGANISM: Brassica napus

<400> SEQUENCE: 18

```
gtattgcatg gacaccatat tattttaggt aaactttcaa cgcaaaacca atagacctta     60
atgataaatc gtttcaaact tttgatttaa cttttcattt cagtgcaaac gttatcgctt    120
ttagattcct tgttaaactt tcaggcaaat aaactggaag cagactcaaa acgataagga    180
aagagctcga agaaccaact gaagtggaaa gtgaactgaa acgaagactt gaccagctaa    240
ctaatcatct tactcaaaaa caatcccagg tatatgaata cttttaaata aaagagaatt    300
cagacaaaac taatataaaa acttccaact ctcctgccaa atttaccaag tcgactttcc    360
tcataggaag caactctatc gtttagaatc catattttaa ctacttcaca ctattctctc    420
cataatctct ctctcataca aatacattga aggttttgac aacaaacaca aagctctaga    480
actcaagcag gagcaattga sactctttca atctcaacta catactccag cgaagcagaa    540
ggcggtatct gaaaacccga ttcaagttca gcaccctctt ctccaaatcc taaagctggt    600
ggaacgatca ctctcctttt acctccggcc ttcatcgacc tcagaacata atctacgcct    660
tcgcataatc ctttgctata tggctttgaa cccaccacaa gtgccaatgg cttcttattc    720
```

```
ttgtctttgc ttccaaatgt gtcaacaaac acttgtcccg tttcttgcac ttgtcccttc    780

atattaatca ctaccaaatc acctgctctt ggtgttgccc ctcctccaag ccgtagatca    840

tagtacctgc atagtttgat tcaatatagt ccaagacttg accgaagcta aggagaccca    900

ttgacaaaat gtacctaatg ccattgggca agacaatctc cttctcttct tcgacgtctc    960

tacaaacaca ccatacaaaa gcagttccaa agctttgtga g                       1001
```

```
<210> SEQ ID NO 19
<211> LENGTH: 1001
<212> TYPE: DNA
<213> ORGANISM: Brassica napus

<400> SEQUENCE: 19

atcatcttac tcaaaaacaa tcccaggtat atgaatactt ttaaataaaa gagaattcag     60

acaaaactaa tataaaaact tccaactctc ctgccaaatt taccaagtcg actttcctca    120

taggaagcaa ctctatcgtt tagaatccat attttaacta cttcacacta ttctctccat    180

aatctctctc tcatacaaat acattgaagg ttttgacaac aaacacaaag ctctagaact    240

caagcaggag caattgagac tctttcaatc tcaactacat actccagcga agcagaaggc    300

ggtatctgaa aacccgattc aagttcagca ccctcttctc caaatcctaa agctggtgga    360

acgatcactc tccttttacc tccggccttc atcgacctca gaacataatc tacgccttcg    420

cataatcctt tgctatatgg ctttgaaccc accacaagtg ccaatggctt cttattcttg    480

tctttgcttc caaatgtgtc macaaacact tgtcccgttt cttgcacttg tcccttcata    540

ttaatcacta ccaaatcacc tgctcttggt gttgcccctc ctccaagccg tagatcatag    600

tacctgcata gtttgattca atatagtcca agacttgacc gaagctaagg agacccattg    660

acaaaatgta cctaatgcca ttgggcaaga caatctcctt ctcttcttcg acgtctctac    720

aaacacacca tacaaaagca gttccaaagc tttgtgagag tgatgacaac taagacagta    780

acttgaagct atggagatgt gaaaaccttg tgttagcttc ttcttgagaa acctcaagcc    840

gtgttttgat ctgctcggag atcacaccga aagctagaaa ccccgcccag gcaagacccg    900

caccgattcc aaaccgtctg gtcaaagaag aagcgaccca atccgtcgtc tcaacgctgg    960

tcttcttcct cttctgttgc gatgcgaggg gttgctccgt c                       1001
```

```
<210> SEQ ID NO 20
<211> LENGTH: 1001
<212> TYPE: DNA
<213> ORGANISM: Brassica napus

<400> SEQUENCE: 20

atgaatactt ttaaataaaa gagaattcag acaaaactaa tataaaaact tccaactctc     60

ctgccaaatt taccaagtcg actttcctca taggaagcaa ctctatcgtt tagaatccat    120

attttaacta cttcacacta ttctctccat aatctctctc tcatacaaat acattgaagg    180

ttttgacaac aaacacaaag ctctagaact caagcaggag caattgagac tctttcaatc    240

tcaactacat actccagcga agcagaaggc ggtatctgaa aacccgattc aagttcagca    300

ccctcttctc caaatcctaa agctggtgga acgatcactc tccttttacc tccggccttc    360

atcgacctca gaacataatc tacgccttcg cataatcctt tgctatatgg ctttgaaccc    420

accacaagtg ccaatggctt cttattcttg tctttgcttc caaatgtgtc aacaaacact    480

tgtcccgttt cttgcacttg ycccttcata ttaatcacta ccaaatcacc tgctcttggt    540
```

```
gttgcccctc ctccaagccg tagatcatag tacctgcata gtttgattca atatagtcca    600

agacttgacc gaagctaagg agacccattg acaaaatgta cctaatgcca ttgggcaaga    660

caatctcctt ctcttcttcg acgtctctac aaacacacca tacaaaagca gttccaaagc    720

tttgtgagag tgatgacaac taagacagta acttgaagct atggagatgt gaaaaccttg    780

tgttagcttc ttcttgagaa acctcaagcc gtgttttgat ctgctcggag atcacaccga    840

aagctagaaa ccccgcccag gcaagacccg caccgattcc aaaccgtctg gtcaaagaag    900

aagcgaccca atccgtcgtc tcaacgctgg tcttcttcct cttctgttgc gatgcgaggg    960

gttgctccgt ctttacggat tgagtcggag tagaagaaga c                       1001


<210> SEQ ID NO 21
<211> LENGTH: 1001
<212> TYPE: DNA
<213> ORGANISM: Brassica napus

<400> SEQUENCE: 21

tcaaagaaga agcgacccaa tccgtcgtct caacgctggt cttcttcctc ttctgttgcg     60

atgcgagggg ttgctccgtc tttacggatt gagtcggagt agaagaagac tctggctgag    120

aaggagggtt ctgctccgga ggagtggaag aagaggcgca acagaggtga tacggcgccg    180

tcttcgtgaa cggctttgaa aggaacggag ctgtaacggt gaatagattc gccatttcgg    240

cataaaataa aataaaaacc tcagctttat tataagtata taaacgctta tcctgttcgt    300

gtgattcatt ttaaagacag aagtcaagcc aagttcttgt cactgtcagt gataaaccga    360

atccggttag gctaaaccgg gtcgtcgaaa ttattaaaaa aaattaaatt gtttcttctt    420

cttcttctcc tttctctctc caatcagtta ggaagaaggt cgtgacccac tccgaaggac    480

aaaaccgaga gacgatccga kaaataaggt gaatttgacg agaatcatta ggctgagaag    540

gaaactcgga gacccaaaat cgtaaatcac caatctttaa tctgtttttc taattcagta    600

gtagtagttg atgggtggtg gtgggaatct cgtcgacggt gttcgtcgtt ggctttttca    660

acgaccctct tcttccaata ataatcctca cgaacccatt gttccaaagt ctgatacttt    720

ttctattccc catcatcaat ctgagcttat cattaccgaa gatctcgatt tctctggtct    780

caagcttatc aaagttccca aacgtcatca cttacccatg gatcctcaaa agaaggtacc    840

ttttggcgcg atcactgatt gtgtagacat catttgatct gtgatctttg tttgattgaa    900

gtttacttct attaatgttt tgtacattgt tcaacaagta gctagatttt gattaggcct    960

tttatagggt gttattgatt attgatttat ttatttattt g                       1001


<210> SEQ ID NO 22
<211> LENGTH: 1001
<212> TYPE: DNA
<213> ORGANISM: Brassica napus

<400> SEQUENCE: 22

attaggctga gaaggaaact cggagaccca aaatcgtaaa tcaccaatct ttaatctgtt     60

tttctaattc agtagtagta gttgatgggt ggtggtggga atctcgtcga cggtgttcgt    120

cgttggcttt ttcaacgacc ctcttcttcc aataataatc ctcacgaacc cattgttcca    180

aagtctgata ctttttctat tccccatcat caatctgagc ttatcattac cgaagatctc    240

gatttctctg gtctcaagct tatcaaagtt cccaaacgtc atcacttacc catggatcct    300

caaaagaagg taccttttgg cgcgatcact gattgtgtag acatcatttg atctgtgatc    360

tttgtttgat tgaagtttac ttctattaat gttttgtaca ttgttcaaca agtagctaga    420
```

```
ttttgattag gccttttata gggtgttatt gattattgat ttatttattt atttgattgg    480
atcctactgt ttgttcaggg ygtgcaggaa aaggacttct tcacggagta cggagaagca    540
aacaggtacc aggttcaaga agtcgttggt aaaggaagct acggtgttgt ggcctctgct    600
ctagacacac acactggcga aagagttgct atcaagaaga tcaacgacgt ctttgagcat    660
gtctctgatg caaccaggat tctcagggag atcaagctgc tgaggttgct taagcatccg    720
gatgttgtgg agattaagca tattatgctg cctccttctc gtagagagtt cagggatatt    780
tacgttgtgt ttgagctgat ggagtctgat cttcatcagg tgattaaggc gaatgatgat    840
ttgactcctg atcattatca gttcttcttg tatcagcttc tccgtggtct caaatatgtc    900
cacgcaggtt aagtttctgg ttttaaaaca gtcttctctt ttgtctgtct ttattgaaac    960
gtttgtgtgt tttcagctaa tgtgtttcat cgggatttga a                       1001
```

<210> SEQ ID NO 23
<211> LENGTH: 1001
<212> TYPE: DNA
<213> ORGANISM: Brassica napus

<400> SEQUENCE: 23

```
gacccaaaat cgtaaatcac caatctttaa tctgtttttc taattcagta gtagtagttg     60
atgggtggtg gtgggaatct cgtcgacggt gttcgtcgtt ggctttttca acgaccctct    120
tcttccaata ataatcctca cgaacccatt gttccaaagt ctgatacttt ttctattccc    180
catcatcaat ctgagcttat cattaccgaa gatctcgatt tctctggtct caagcttatc    240
aaagttccca aacgtcatca cttacccatg gatcctcaaa agaaggtacc ttttggcgcg    300
atcactgatt gtgtagacat catttgatct gtgatctttg tttgattgaa gtttacttct    360
attaatgttt tgtacattgt tcaacaagta gctagatttt gattaggcct tttatagggt    420
gttattgatt attgatttat ttatttattt gattggatcc tactgtttgt tcagggtgtg    480
caggaaaagg acttcttcac rgagtacgga gaagcaaaca ggtaccaggt tcaagaagtc    540
gttggtaaag gaagctacgg tgttgtggcc tctgctctag acacacacac tggcgaaaga    600
gttgctatca agaagatcaa cgacgtcttt gagcatgtct ctgatgcaac caggattctc    660
agggagatca agctgctgag gttgcttaag catccggatg ttgtggagat taagcatatt    720
atgctgcctc cttctcgtag agagttcagg gatatttacg ttgtgtttga gctgatggag    780
tctgatcttc atcaggtgat taaggcgaat gatgatttga ctcctgatca ttatcagttc    840
ttcttgtatc agcttctccg tggtctcaaa tatgtccacg caggttaagt ttctggtttt    900
aaaacagtct tctcttttgt ctgtctttat tgaaacgttt gtgtgttttc agctaatgtg    960
tttcatcggg atttgaaacc aaagaacatt ctagctaatg c                       1001
```

<210> SEQ ID NO 24
<211> LENGTH: 1001
<212> TYPE: DNA
<213> ORGANISM: Brassica napus

<400> SEQUENCE: 24

```
tttcaacgac cctcttcttc caataataat cctcacgaac ccattgttcc aaagtctgat     60
actttttcta ttccccatca tcaatctgag cttatcatta ccgaagatct cgatttctct    120
ggtctcaagc ttatcaaagt tcccaaacgt catcacttac ccatggatcc tcaaaagaag    180
gtaccttttg gcgcgatcac tgattgtgta gacatcattt gatctgtgat ctttgtttga    240
```

```
ttgaagttta cttctattaa tgttttgtac attgttcaac aagtagctag attttgatta    300

ggccttttat agggtgttat tgattattga tttatttatt tatttgattg gatcctactg    360

tttgttcagg gtgtgcagga aaaggacttc ttcacggagt acggagaagc aaacaggtac    420

caggttcaag aagtcgttgg taaaggaagc tacggtgttg tggcctctgc tctagacaca    480

cacactggcg aaagagttgc yatcaagaag atcaacgacg tctttgagca tgtctctgat    540

gcaaccagga ttctcaggga gatcaagctg ctgaggttgc ttaagcatcc ggatgttgtg    600

gagattaagc atattatgct gcctccttct cgtagagagt tcagggatat ttacgttgtg    660

tttgagctga tggagtctga tcttcatcag gtgattaagg cgaatgatga tttgactcct    720

gatcattatc agttcttctt gtatcagctt ctccgtggtc tcaaatatgt ccacgcaggt    780

taagtttctg gttttaaaac agtcttctct tttgtctgtc tttattgaaa cgtttgtgtg    840

ttttcagcta atgtgtttca tcgggatttg aaaccaaaga acattctagc taatgctgat    900

tgcaagttga agatctgtga ttttggactc gctcgtgtct cttttaacga cgcaccaact    960

gctatattct ggactgtgag tcctctaatt tgaatgcagc a                      1001
```

<210> SEQ ID NO 25
<211> LENGTH: 1001
<212> TYPE: DNA
<213> ORGANISM: Brassica napus

<400> SEQUENCE: 25

```
cccattgttc caaagtctga tactttttct attccccatc atcaatctga gcttatcatt     60

accgaagatc tcgatttctc tggtctcaag cttatcaaag ttcccaaacg tcatcactta    120

cccatggatc ctcaaaagaa ggtacctttt ggcgcgatca ctgattgtgt agacatcatt    180

tgatctgtga tctttgtttg attgaagttt acttctatta atgttttgta cattgttcaa    240

caagtagcta gattttgatt aggcctttta tagggtgtta ttgattattg atttatttat    300

ttatttgatt ggatcctact gtttgttcag ggtgtgcagg aaaaggactt cttcacggag    360

tacggagaag caaacaggta ccaggttcaa gaagtcgttg gtaaaggaag ctacggtgtt    420

gtggcctctg ctctagacac acacactggc gaaagagttg ctatcaagaa gatcaacgac    480

gtctttgagc atgtctctga ygcaaccagg attctcaggg agatcaagct gctgaggttg    540

cttaagcatc cggatgttgt ggagattaag catattatgc tgcctccttc tcgtagagag    600

ttcagggata tttacgttgt gtttgagctg atggagtctg atcttcatca ggtgattaag    660

gcgaatgatg atttgactcc tgatcattat cagttcttct tgtatcagct tctccgtggt    720

ctcaaatatg tccacgcagg ttaagtttct ggttttaaaa cagtcttctc ttttgtctgt    780

ctttattgaa acgtttgtgt gttttcagct aatgtgtttc atcgggattt gaaaccaaag    840

aacattctag ctaatgctga ttgcaagttg aagatctgtg attttggact cgctcgtgtc    900

tcttttaacg acgcaccaac tgctatattc tggactgtga gtcctctaat ttgaatgcag    960

cagagcttct cattaaactg tttgtgaact cactctttta t                      1001
```

<210> SEQ ID NO 26
<211> LENGTH: 1001
<212> TYPE: DNA
<213> ORGANISM: Brassica napus

<400> SEQUENCE: 26

```
ttacccatgg atcctcaaaa gaaggtacct tttggcgcga tcactgattg tgtagacatc     60

atttgatctg tgatctttgt ttgattgaag tttacttcta ttaatgtttt gtacattgtt    120
```

caacaagtag ctagattttg attaggcctt ttatagggtg ttattgatta ttgatttatt 180
tatttatttg attggatcct actgtttgtt cagggtgtgc aggaaaagga cttcttcacg 240
gagtacggag aagcaaacag gtaccaggtt caagaagtcg ttggtaaagg aagctacggt 300
gttgtggcct ctgctctaga cacacacact ggcgaaagag ttgctatcaa gaagatcaac 360
gacgtctttg agcatgtctc tgatgcaacc aggattctca gggagatcaa gctgctgagg 420
ttgcttaagc atccggatgt tgtggagatt aagcatatta tgctgcctcc ttctcgtaga 480
gagttcaggg atatttacgt ygtgtttgag ctgatggagt ctgatcttca tcaggtgatt 540
aaggcgaatg atgatttgac tcctgatcat tatcagttct tcttgtatca gcttctccgt 600
ggtctcaaat atgtccacgc aggttaagtt tctggtttta aaacagtctt ctcttttgtc 660
tgtctttatt gaaacgtttg tgtgttttca gctaatgtgt ttcatcggga tttgaaacca 720
aagaacattc tagctaatgc tgattgcaag ttgaagatct gtgattttgg actcgctcgt 780
gtctctttta acgacgcacc aactgctata ttctggactg tgagtcctct aatttgaatg 840
cagcagagct tctcattaaa ctgtttgtga actcactctt ttatctatgt tttgtaggat 900
tatgtagcta ctcggtggta ccgtgcccct gaactctgtg gatcgttttt ctccaaagta 960
agattctttt tttttgttta ttcactgaac ctctctgtat c 1001

<210> SEQ ID NO 27
<211> LENGTH: 1001
<212> TYPE: DNA
<213> ORGANISM: Brassica napus

<400> SEQUENCE: 27
aaaacagtct tctcttttgt ctgtctttat tgaaacgttt gtgtgttttc agctaatgtg 60
tttcatcggg atttgaaacc aaagaacatt ctagctaatg ctgattgcaa gttgaagatc 120
tgtgattttg gactcgctcg tgtctctttt aacgacgcac caactgctat attctggact 180
gtgagtcctc taatttgaat gcagcagagc ttctcattaa actgtttgtg aactcactct 240
tttatctatg ttttgtagga ttatgtagct actcggtggt accgtgcccc tgaactctgt 300
ggatcgtttt tctccaaagt aagattcttt ttttttgttt attcactgaa cctctctgta 360
tcacaagaac ggacttcttg atctaggtcc tatattttca taagatatac cgtctaatgc 420
taagttaact ttcagtacac tcctgcgatt gatatatgga gtgttggttg catttttgcg 480
gaaatgatat tgggaaagcc wttgtttccc gggaagaacg tggtgcacca acttgatctt 540
atgactgact ttcttggcac tcctccgcct gagtccatat caagggttag tcactcaaac 600
atgtgttaca ttcccatcat ttgagagcta gttaatgagt tttttttgtt tttttttgca 660
atcttgaaat tatgacagat aagaaatgaa aaggcgagga gatatctaag cagcatgagg 720
aagaaacagc cggttccttt ctctcacaag ttccctaaag ctgatccttt ggctctccgc 780
cttctcgaac gccttattgc ctttgatcct aaagatcgtg tctcagctga agatgtaagc 840
gacaagcaac tttcattttt tttttaatta caaagactta aaactctcaa gttcattatt 900
ctgatttggt tatttacagg cactagctga tccttatttc agtggtctgt caaactcaga 960
gcgtgaacca tcaacgcagc caatctcaaa gcttgagttt g 1001

<210> SEQ ID NO 28
<211> LENGTH: 1003
<212> TYPE: DNA
<213> ORGANISM: Brassica napus
<220> FEATURE:

<221> NAME/KEY: misc_feature
<222> LOCATION: (502)..(503)
<223> OTHER INFORMATION: TT is Indel (insertion/deletion) marker

<400> SEQUENCE: 28

```
ttttggactc gctcgtgtct cttttaacga cgcaccaact gctatattct ggactgtgag     60
tcctctaatt tgaatgcagc agagcttctc attaaactgt ttgtgaactc actcttttat    120
ctatgttttg taggattatg tagctactcg gtggtaccgt gcccctgaac tctgtggatc    180
gtttttctcc aaagtaagat tctttttttt tgtttattca ctgaacctct ctgtatcaca    240
agaacggact tcttgatcta ggtcctatat tttcataaga tataccgtct aatgctaagt    300
taactttcag tacactcctg cgattgatat atggagtgtt ggttgcattt ttgcggaaat    360
gatattggga aagcctttgt ttcccgggaa gaacgtggtg caccaacttg atcttatgac    420
tgactttctt ggcactcctc cgcctgagtc catatcaagg gttagtcact caaacatgtg    480
ttacattccc atcatttgag attgctagtt aatgagtttt ttttgttttt ttttgcaatc    540
ttgaaattat gacagataag aaatgaaaag gcgaggagat atctaagcag catgaggaag    600
aaacagccgg ttcctttctc tcacaagttc cctaaagctg atcctttggc tctccgcctt    660
ctcgaacgcc ttattgcctt tgatcctaaa gatcgtgtct cagctgaaga tgtaagcgac    720
aagcaacttt catttttttt ttaattacaa agacttaaaa ctctcaagtt cattattctg    780
atttggttat ttacaggcac tagctgatcc ttatttcagt ggtctgtcaa actcagagcg    840
tgaaccatca acgcagccaa tctcaaagct tgagtttgat tttgagagaa agaagttgaa    900
caaagatgac gtcagagaat taatctaccg agaggtaaca caaaaaaaaa tgcttttgac    960
tatgtcttat tgttctcttc attgatctaa cattcacttt atc                     1003
```

<210> SEQ ID NO 29
<211> LENGTH: 1001
<212> TYPE: DNA
<213> ORGANISM: Brassica napus

<400> SEQUENCE: 29

```
ttggactcgc tcgtgtctct tttaacgacg caccaactgc tatattctgg actgtgagtc     60
ctctaatttg aatgcagcag agcttctcat taaactgttt gtgaactcac tcttttatct    120
atgttttgta ggattatgta gctactcggt ggtaccgtgc ccctgaactc tgtggatcgt    180
ttttctccaa agtaagattc tttttttttg tttattcact gaacctctct gtatcacaag    240
aacggacttc ttgatctagg tcctatattt tcataagata taccgtctaa tgctaagtta    300
actttcagta cactcctgcg attgatatat ggagtgttgg ttgcattttt gcggaaatga    360
tattgggaaa gcctttgttt cccgggaaga acgtggtgca ccaacttgat cttatgactg    420
actttcttgg cactcctccg cctgagtcca tatcaagggt tagtcactca aacatgtgtt    480
acattcccat catttgagag ytagttaatg agtttttttt gttttttttt gcaatcttga    540
aattatgaca gataagaaat gaaaaggcga ggagatatct aagcagcatg aggaagaaac    600
agccggttcc tttctctcac aagttcccta aagctgatcc tttggctctc cgccttctcg    660
aacgccttat tgcctttgat cctaaagatc gtgtctcagc tgaagatgta agcgacaagc    720
aactttcatt tttttttaa ttacaaagac ttaaaactct caagttcatt attctgattt      780
ggttatttac aggcactagc tgatccttat ttcagtggtc tgtcaaactc agagcgtgaa    840
ccatcaacgc agccaatctc aaagcttgag tttgattttg agagaaagaa gttgaacaaa    900
gatgacgtca gagaattaat ctaccgagag gtaacacaaa aaaaaatgct tttgactatg    960
```

tcttattgtt ctcttcattg atctaacatt cactttatct t 1001

<210> SEQ ID NO 30
<211> LENGTH: 1001
<212> TYPE: DNA
<213> ORGANISM: Brassica napus

<400> SEQUENCE: 30
agtacactcc tgcgattgat atatggagtg ttggttgcat tttgcggaa atgatattgg 60 gaaagccttt gtttcccggg aagaacgtgg tgcaccaact tgatcttatg actgactttc 120
ttggcactcc tccgcctgag tccatatcaa gggttagtca ctcaaacatg tgttacattc 180
ccatcatttg agagctagtt aatgagtttt ttttgttttt ttttgcaatc ttgaaattat 240
gacagataag aaatgaaaag gcgaggagat atctaagcag catgaggaag aaacagccgg 300
ttcctttctc tcacaagttc cctaaagctg atcctttggc tctccgcctt ctcgaacgcc 360
ttattgcctt tgatcctaaa gatcgtgtct cagctgaaga tgtaagcgac aagcaacttt 420
catttttttt ttaattacaa agacttaaaa ctctcaagtt cattattctg atttggttat 480
ttacaggcac tagctgatcc wtatttcagt ggtctgtcaa actcagagcg tgaaccatca 540
acgcagccaa tctcaaagct tgagtttgat tttgagagaa agaagttgaa caaagatgac 600
gtcagagaat taatctaccg agaggtaaca caaaaaaaaa tgcttttgac tatgtcttat 660
tgttctcttc attgatctaa cattcacttt atctttggga aaaacattta gatattggag 720
tatcatcctc agatgctgga ggagtacaag cgcggtggtg atcagctcag cttcatgtac 780
cctaggttag ctaattaaac acctcatgaa ctataattcc ctgaaaacag aatgaaacca 840
agaactcttc tgttgtttac gcagtggggt tgatcggttc aagaggcagt ttgctcacct 900
tgaagagaat caaggtaaac caggagcagg ggcaggagga ggaagaagta ctgcaatgca 960
tagacaccat gcttccttgc caatgtaatg tctttttcac a 1001

<210> SEQ ID NO 31
<211> LENGTH: 1001
<212> TYPE: DNA
<213> ORGANISM: Brassica napus

<400> SEQUENCE: 31
acactcctgc gattgatata tggagtgttg gttgcatttt tgcggaaatg atattgggaa 60
agcctttgtt tcccgggaag aacgtggtgc accaacttga tcttatgact gactttcttg 120
gcactcctcc gcctgagtcc atatcaaggg ttagtcactc aaacatgtgt tacattccca 180
tcatttgaga gctagttaat gagttttttt tgtttttttt tgcaatcttg aaattatgac 240
agataagaaa tgaaaaggcg aggagatatc taagcagcat gaggaagaaa cagccggttc 300
ctttctctca caagttccct aaagctgatc ctttggctct ccgccttctc gaacgcctta 360
ttgcctttga tcctaaagat cgtgtctcag ctgaagatgt aagcgacaag caactttcat 420
ttttttttta attacaaaga cttaaaactc tcaagttcat tattctgatt tggttattta 480
caggcactag ctgatcctta yttcagtggt ctgtcaaact cagagcgtga accatcaacg 540
cagccaatct caaagcttga gtttgatttt gagagaaaga agttgaacaa agatgacgtc 600
agagaattaa tctaccgaga ggtaacacaa aaaaaaatgc ttttgactat gtcttattgt 660
tctcttcatt gatctaacat tcactttatc tttgggaaaa acatttagat attggagtat 720
catcctcaga tgctggagga gtacaagcgc ggtggtgatc agctcagctt catgtaccct 780

```
aggttagcta attaaacacc tcatgaacta taattccctg aaaacagaat gaaaccaaga    840

actcttctgt tgtttacgca gtggggttga tcggttcaag aggcagtttg ctcaccttga    900

agagaatcaa ggtaaaccag gagcaggggc aggaggagga agaagtactg caatgcatag    960

acaccatgct tccttgccaa tgtaatgtct tttcacaga a                        1001


<210> SEQ ID NO 32
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion [+/A]

<400> SEQUENCE: 32

gtccatatca agggttagtc actcaaacat gtgttacatt cccatcattt gagagctagt     60

taatgagttt tttttgtttt tttttgcaat cttgaaatta tgacagataa gaaatgaaaa    120

ggcgaggaga tatctaagca gcatgaggaa gaaacagccg gttcctttct ctcacaagtt    180

ccctaaagct gatcctttgg ctctccgcct tctcgaacgc cttattgcct ttgatcctaa    240

agatcgtgtc tcagctgaag atgtaagcga caagcaactt tcattttttt tttaattaca    300

aagacttaaa actctcaagt tcattattct gatttggtta tttacaggca ctagctgatc    360

cttatttcag tggtctgtca aactcagagc gtgaaccatc aacgcagcca atctcaaagc    420

ttgagtttga ttttgagaga aagaagttga acaaagatga cgtcagagaa ttaatctacc    480

gagaggtaac acaaaaaaaa antgcttttg actatgtctt attgttctct tcattgatct    540

aacattcact ttatctttgg gaaaaacatt tagatattgg agtatcatcc tcagatgctg    600

gaggagtaca agcgcggtgg tgatcagctc agcttcatgt accctaggtt agctaattaa    660

acacctcatg aactataatt ccctgaaaac agaatgaaac caagaactct tctgttgttt    720

acgcagtggg gttgatcggt tcaagaggca gtttgctcac cttgaagaga atcaaggtaa    780

accaggagca ggggcaggag gaggaagaag tactgcaatg catagacacc atgcttcctt    840

gccaatgtaa tgtctttttc acagaatctc ttgctttgct ctctctttct ctgaaagcgt    900

tgggcttctt tgtgattgtg tgttgcagag agagagttcc tgctcagagt ggtcagactg    960

tagaagaaag cagtgatgtt gagagaagag cagcagctgc tg                      1002


<210> SEQ ID NO 33
<211> LENGTH: 1001
<212> TYPE: DNA
<213> ORGANISM: Brassica napus

<400> SEQUENCE: 33

ctagctgatc cttatttcag tggtctgtca aactcagagc gtgaaccatc aacgcagcca     60

atctcaaagc ttgagtttga ttttgagaga aagaagttga acaaagatga cgtcagagaa    120

ttaatctacc gagaggtaac acaaaaaaaa atgcttttga ctatgtctta ttgttctctt    180

cattgatcta acattcactt tatctttggg aaaaacattt agatattgga gtatcatcct    240

cagatgctgg aggagtacaa gcgcggtggt gatcagctca gcttcatgta ccctaggtta    300

gctaattaaa cacctcatga actataattc cctgaaaaca gaatgaaacc aagaactctt    360

ctgttgttta cgcagtgggg ttgatcggtt caagaggcag tttgctcacc ttgaagagaa    420

tcaaggtaaa ccaggagcag gggcaggagg aggaagaagt actgcaatgc atagacacca    480

tgcttccttg ccaatgtaat rtctttttca cagaatctct tgctttgctc tctctttctc    540
```

```
tgaaagcgtt gggcttcttt gtgattgtgt gttgcagaga gagagttcct gctcagagtg    600

gtcagactgt agaagaaagc agtgatgttg agagaagagc agcagctgct gtggcttcaa    660

ctttggaatc tgaggaagca gacaatggag gaggttacag tgctcgtagc ctcatgaaga    720

gttcgagcat cagtggttct aaatgcatcg gtgtccaatc taaaaccgac aaagaggtta    780

gttagttagt tagttagtgg agttaaaaaa acagaggatc ttgaaaggaa catggagatg    840

gagtttgctt acttactgtt gtttctgttc tgtgttgtag gacaccatag ctgaggaagg    900

agatgatgaa tcagtggcgg agcttactga tagagttgct tctcttcgta attcttaaaa    960

cgtttttgtt tttttttttg gcgtttggtg aaagctttct g                       1001
```

```
<210> SEQ ID NO 34
<211> LENGTH: 1001
<212> TYPE: DNA
<213> ORGANISM: Brassica napus
<220> FEATURE:
<221> NAME/KEY: misc_feature
<222> LOCATION: (501)..(501)
<223> OTHER INFORMATION: where n is an insertion/deletion [-/T]

<400> SEQUENCE: 34

atccttattt cagtggtctg tcaaactcag agcgtgaacc atcaacgcag ccaatctcaa     60

agcttgagtt tgattttgag agaaagaagt tgaacaaaga tgacgtcaga gaattaatct    120

accgagaggt aacacaaaaa aaaatgcttt tgactatgtc ttattgttct cttcattgat    180

ctaacattca ctttatcttt gggaaaaaca tttagatatt ggagtatcat cctcagatgc    240

tggaggagta caagcgcggt ggtgatcagc tcagcttcat gtaccctagg ttagctaatt    300

aaacacctca tgaactataa ttccctgaaa acagaatgaa accaagaact cttctgttgt    360

ttacgcagtg gggttgatcg gttcaagagg cagtttgctc accttgaaga gaatcaaggt    420

aaaccaggag caggggcagg aggaggaaga agtactgcaa tgcatagaca ccatgcttcc    480

ttgccaatgt aatgtctttt ncacagaatc tcttgctttg ctctctcttt ctctgaaagc    540

gttgggcttc tttgtgattg tgtgttgcag agagagagtt cctgctcaga gtggtcagac    600

tgtagaagaa agcagtgatg ttgagagaag agcagcagct gctgtggctt caactttgga    660

atctgaggaa gcagacaatg gaggaggtta cagtgctcgt agcctcatga agagttcgag    720

catcagtggt tctaaatgca tcggtgtcca atctaaaacc gacaaagagg ttagttagtt    780

agttagttag tggagttaaa aaaacagagg atcttgaaag gaacatggag atggagtttg    840

cttacttact gttgtttctg ttctgtgttg taggacacca tagctgagga aggagatgat    900

gaatcagtgg cggagcttac tgatagagtt gcttctcttc gtaattctta aaacgttttt    960

gttttttttt ttggcgtttg gtgaaagctt tctggtgaaa a                       1001
```

```
<210> SEQ ID NO 35
<211> LENGTH: 1001
<212> TYPE: DNA
<213> ORGANISM: Brassica napus

<400> SEQUENCE: 35

acgtcagaga attaatctac cgagaggtaa cacaaaaaaa aatgcttttg actatgtctt     60

attgttctct tcattgatct aacattcact ttatctttgg gaaaaacatt tagatattgg    120

agtatcatcc tcagatgctg gaggagtaca agcgcggtgg tgatcagctc agcttcatgt    180

accctaggtt agctaattaa acacctcatg aactataatt ccctgaaaac agaatgaaac    240
```

```
caagaactct tctgttgttt acgcagtggg gttgatcggt tcaagaggca gtttgctcac    300

cttgaagaga atcaaggtaa accaggagca ggggcaggag gaggaagaag tactgcaatg    360

catagacacc atgcttcctt gccaatgtaa tgtctttttc acagaatctc ttgctttgct    420

ctctctttct ctgaaagcgt tgggcttctt tgtgattgtg tgttgcagag agagagttcc    480

tgctcagagt ggtcagactg yagaagaaag cagtgatgtt gagagaagag cagcagctgc    540

tgtggcttca actttggaat ctgaggaagc agacaatgga ggaggttaca gtgctcgtag    600

cctcatgaag agttcgagca tcagtggttc taaatgcatc ggtgtccaat ctaaaaccga    660

caaagaggtt agttagttag ttagttagtg gagttaaaaa aacagaggat cttgaaagga    720

acatggagat ggagtttgct tacttactgt tgtttctgtt ctgtgttgta ggacaccata    780

gctgaggaag gagatgatga atcagtggcg gagcttactg atagagttgc ttctcttcgt    840

aattcttaaa acgtttttgt ttttttttt ggcgtttggt gaaagctttc tggtgaaaat    900

tggtttctac attttatttt cacttcttcc acatctatct tcgtggttgg gtttgatttg    960

ttggatttaa tagtttgggg gcgagaatga gacctttttta a                     1001
```

```
<210> SEQ ID NO 36
<211> LENGTH: 1001
<212> TYPE: DNA
<213> ORGANISM: Brassica napus

<400> SEQUENCE: 36

acgcagtggg gttgatcggt tcaagaggca gtttgctcac cttgaagaga atcaaggtaa     60

accaggagca ggggcaggag gaggaagaag tactgcaatg catagacacc atgcttcctt    120

gccaatgtaa tgtctttttc acagaatctc ttgctttgct ctctctttct ctgaaagcgt    180

tgggcttctt tgtgattgtg tgttgcagag agagagttcc tgctcagagt ggtcagactg    240

tagaagaaag cagtgatgtt gagagaagag cagcagctgc tgtggcttca actttggaat    300

ctgaggaagc agacaatgga ggaggttaca gtgctcgtag cctcatgaag agttcgagca    360

tcagtggttc taaatgcatc ggtgtccaat ctaaaaccga caaagaggtt agttagttag    420

ttagttagtg gagttaaaaa aacagaggat cttgaaagga acatggagat ggagtttgct    480

tacttactgt tgtttctgtt ytgtgttgta ggacaccata gctgaggaag gagatgatga    540

atcagtggcg gagcttactg atagagttgc ttctcttcgt aattcttaaa acgtttttgt    600

tttttttttt ggcgtttggt gaaagctttc tggtgaaaat tggtttctac attttatttt    660

cacttcttcc acatctatct tcgtggttgg gtttgatttg ttggatttaa tagtttgggg    720

gcgagaatga gaccttttta ataagaacat ctatctccat gtaatttctt ttatcctttt    780

ctataaattg ttctttcaat ctttttaccg attcagtttg cttaagtaca tcatgaaatc    840

agaattaaac taaaaaatag tatactaaaa aaggaaaaca tccaaaaaac ctttatagtt    900

gaagtaaaca tatatatata tatatatata tatatgcagt ttgctttata ttatgatctg    960

aattagttat atatacatac taagtgtttt tcaaaaatag t                      1001
```

```
<210> SEQ ID NO 37
<211> LENGTH: 1001
<212> TYPE: DNA
<213> ORGANISM: Brassica napus

<400> SEQUENCE: 37

agataccacc ttcaccggtt gaaaacaagt tttgcgagaa tcacgttcga gtaaaattta     60

tgcacttcat ttaaatatta caagtgttta tttattcgac tataaatgtt cgtaaagacc    120
```

```
acaattcatt tgaagattta ttttattttt cactctcata aaatcctttt gtattcacca    180

gggtcatcaa tatacataca ctcatctgat ttatatagtt gcatggcagt taattgcaat    240

ttagtcctag gtgatttgtt ctattataaa tcaaaccaag agagttgcat gttttccatg    300

acgaagtatc ttctactagt agattactgg cagttggtgt aatagttacc accagtagaa    360

actagtttac caacgagtac aacgaggatc atccacgtgc aaggagtgat cctcgtaact    420

gacggcagga atgatgtaac gtggcaggac gaaccaaagg gatcgtgggt aacagctgag    480

accgtgatac ggcacgtgtc wtgtttgtgg atgaaaagaa gtgtgaaatg gcctatgcat    540

ggtctatagg ttacactaat ctgaccaaaa gcttctttta accttttcct tttgtttctt    600

ctttcgctta taaccaagtg agaaactgta ttgtatttcc ctgaaaacat tagattaagt    660

atgagggatt acatatactt aaggcatctt taaccttagt ttatttatga taaagttagt    720

ttcagagtaa tatagcatta ttagctttga tggtttgtac aatagtgatg aatttggaca    780

tgaccataaa ctacaagaca cgagtggatt ctcataatat ttgcaccact aaggacaaaa    840

taactcatca tgctactttg ttgaaatata ttaccattat tattaatgta ttataaaaat    900

acgaacaagt tattattgaa ttgggtttac agctttcaag atatatttta tataaaaatg    960

aaaataaaaa caagaatttg tttacatata aaaagcaaac a                        1001
```

<210> SEQ ID NO 38
<211> LENGTH: 1001
<212> TYPE: DNA
<213> ORGANISM: Brassica napus

<400> SEQUENCE: 38

```
gatgaaaaga agtgtgaaat ggcctatgca tggtctatag gttacactaa tctgaccaaa     60

agcttctttt aaccttttcc ttttgtttct tctttcgctt ataaccaagt gagaaactgt    120

attgtatttc cctgaaaaca ttagattaag tatgagggat tacatatact taaggcatct    180

ttaaccttag tttatttatg ataaagttag tttcagagta atatagcatt attagctttg    240

atggtttgta caatagtgat gaatttggac atgaccataa actacaagac acgagtggat    300

tctcataata tttgcaccac taaggacaaa ataactcatc atgctacttt gttgaaatat    360

attaccatta ttattaatgt attataaaaa tacgaacaag ttattattga attgggttta    420

cagctttcaa gatatatttt atataaaaat gaaaataaaa acaagaattt gtttacatat    480

aaaaagcaaa cacgcatgta waataaattg gactgcatgt aaatcattgt tcaaattcat    540

tgtatttgtc gatggattaa ttaaatatct ttttgctata aaataaaatt ttatctttta    600

accaaaaaaa ataaaaaaaa taaaaaaaaa taaaatttta tctatataaa ccattacata    660

gatgtccatc ccaatacgga catgcgctga acacaacaaa cgattctttt taagagaatc    720

tctctctctc tattctctcc acttctctct ctgtggatcg atggcagctt cggttgatcc    780

tttggtggtt ggaagagtga tcggagatgt gttggacatg ttcatcccca ccgccaacat    840

gtctgtctac tttggcccca aacacataac taacggctgc gagatcaaac cctctgccgc    900

agtcaaccct ccaaaagtca acatctccgg caactccaat gagctttaca ctctcgtata    960

catattaatc ttctcgcttc tatccatttt ttgtgctagc t                        1001
```

<210> SEQ ID NO 39
<211> LENGTH: 685
<212> TYPE: DNA
<213> ORGANISM: Brassica napus

<400> SEQUENCE: 39
tgtggatcga tggcagcttc ggttgatcct ttggtggttg gaagagtgat cggagatgtg 60
ttggacatgt tcatccccac cgccaacatg tctgtctact ttggccccaa acacataact 120
aacggctgcg agatcaaacc ctctgccgca gtcaaccctc caaaagtcaa catctccggc 180
aactccaatg agctttacac tctcgtgatg actgacccgg acgcacctag cccgagtgag 240
ccgaacatga gagaatgggt ccattggatt gtcgtggata tcccgggagg caccaacccc 300
tcaaaaggaa aggagatact gccatatatg gagccgagac caccggtggg gattcaccgt 360
tacatatttg tacttttcag gcagaactca ccggtgggta tgatggtgca gcagccgcct 420
tcgcgagcca acttcagcac ccgaatgttc gctggacatc tcgatcttgg tttgcctgtg 480
gccacagttt acttcaacgc ccagaaagag ccagcttcac gcagacgctg atgcaygtca 540
accaaaataa aagagagagc cttttccggt tttacctaaa aaccggaccg gaaagaaata 600
tggggtttat atatcaaacc atattttgta tcatccggtt ctcgactata tatatgtgta 660
gatgcatata caattataca aatat 685

<210> SEQ ID NO 40
<211> LENGTH: 1001
<212> TYPE: DNA
<213> ORGANISM: Brassica napus

<400> SEQUENCE: 40
atgatttatt atgtttcagg attgtcgtgg atatcccggg aggcaccaac ccctcaaaag 60
gtatgaaaat aaaagccaaa actaaatttt cgatttttga attttaattg tttcgctatt 120
ttccggaatc tcttaattat tatttttcta aacttttttt acaaatgaat ttcacttttt 180
aactcacttt ctaactcact tgcttagata taaaataacg ttagtgtgaa agccactaag 240
aacacatgat aatggttaac tatgtccatg aagacgtgtt tgaatctaat tgaaaaatcc 300
gatacactag tatgttttat tcatttaaac atattatctg tgcaacgtgg tgctttcggt 360
ttgatatgaa atggattccc cgtattgcac gatattgatt ggttcaacaa cacaaatatg 420
catgactctc acatgcatat aggtataaga gtcactatgt aattttcctt ggtttcaagt 480
tatgccccaa aataatacgt ratgtcttct aaaaccaaca tctaatgtat gtctgtacgt 540
gtacactgat gtatatcaac taaacaacgg acacatgtct tcataaaaaa accttaaaca 600
tgacaaagca taagtgaata gaggatgata attattttat ttttattatt agtaccacgg 660
gaaactttga aatcgatata ctagcatgtt tttcatttta ggaaaggaga tactgccata 720
tatggagccg agaccaccgg tggggattca ccgttacata tttgtacttt tcaggcagaa 780
ctcaccggtg ggtatgatgg tgcagcagcc gccttcgcga gccaacttca gcacccgaat 840
gttcgctgga catctcgatc ttggtttgcc tgtggccaca gtttacttca acgcccagaa 900
agagccagct tcacgcagac gctgatgcac gcaaccaaaa taaaagagag agccttttcc 960
ggttttacct aaaaaccgga ccggaaagaa atatggggtt t 1001

<210> SEQ ID NO 41
<211> LENGTH: 1001
<212> TYPE: DNA
<213> ORGANISM: Brassica napus

<400> SEQUENCE: 41
tgatttatta tgtttcagga ttgtcgtgga tatcccggga ggcaccaacc cctcaaaagg 60
tatgaaaata aaagccaaaa ctaaattttc gatttttgaa ttttaattgt ttcgctattt 120

```
tccggaatct cttaattatt atttttctaa acttttttta caaatgaatt tcacttttta    180

actcactttc taactcactt gcttagatat aaaataacgt tagtgtgaaa gccactaaga    240

acacatgata atggttaact atgtccatga agacgtgttt gaatctaatt gaaaaatccg    300

atacactagt atgttttatt catttaaaca tattatctgt gcaacgtggt gctttcggtt    360

tgatatgaaa tggattcccc gtattgcacg atattgattg gttcaacaac acaaatatgc    420

atgactctca catgcatata ggtataagag tcactatgta attttccttg gtttcaagtt    480

atgccccaaa ataatacgta rtgtcttcta aaaccaacat ctaatgtatg tctgtacgtg    540

tacactgatg tatatcaact aaacaacgga cacatgtctt cataaaaaaa ccttaaacat    600

gacaaagcat aagtgaatag aggatgataa ttattttatt tttattatta gtaccacggg    660

aaactttgaa atcgatatac tagcatgttt ttcattttag gaaaggagat actgccatat    720

atggagccga gaccaccggt ggggattcac cgttacatat ttgtactttt caggcagaac    780

tcaccggtgg gtatgatggt gcagcagccg ccttcgcgag ccaacttcag cacccgaatg    840

ttcgctggac atctcgatct tggtttgcct gtggccacag tttacttcaa cgcccagaaa    900

gagccagctt cacgcagacg ctgatgcacg caaccaaaat aaaagagaga gccttttccg    960

gttttaccta aaaaccggac cggaaagaaa tatggggttt a                       1001
```

<210> SEQ ID NO 42
<211> LENGTH: 1001
<212> TYPE: DNA
<213> ORGANISM: Brassica napus

<400> SEQUENCE: 42

```
aggattgtcg tggatatccc gggaggcacc aacccctcaa aaggtatgaa aataaaagcc     60

aaaactaaat tttcgatttt tgaattttaa ttgtttcgct attttccgga atctcttaat    120

tattattttt ctaaactttt tttacaaatg aatttcactt tttaactcac tttctaactc    180

acttgcttag atataaaata acgttagtgt gaaagccact aagaacacat gataatggtt    240

aactatgtcc atgaagacgt gtttgaatct aattgaaaaa tccgatacac tagtatgttt    300

tattcattta aacatattat ctgtgcaacg tggtgctttc ggtttgatat gaaatggatt    360

ccccgtattg cacgatattg attggttcaa caacacaaat atgcatgact ctcacatgca    420

tataggtata agagtcacta tgtaattttc cttggtttca agttatgccc caaaataata    480

cgtaatgtct tctaaaacca rcatctaatg tatgtctgta cgtgtacact gatgtatatc    540

aactaaacaa cggacacatg tcttcataaa aaaaccttaa acatgacaaa gcataagtga    600

atagaggatg ataattattt tatttttatt attagtacca cgggaaactt tgaaatcgat    660

atactagcat gtttttcatt ttaggaaagg agatactgcc atatatggag ccgagaccac    720

cggtggggat tcaccgttac atatttgtac ttttcaggca gaactcaccg gtgggtatga    780

tggtgcagca gccgccttcg cgagccaact tcagcacccg aatgttcgct ggacatctcg    840

atcttggttt gcctgtggcc acagtttact tcaacgccca gaaagagcca gcttcacgca    900

gacgctgatg cacgcaacca aaataaaaga gagagccttt tccggtttta cctaaaaacc    960

ggaccggaaa gaaatatggg gtttatatat caaaccatat t                       1001
```

<210> SEQ ID NO 43
<211> LENGTH: 1001
<212> TYPE: DNA
<213> ORGANISM: Brassica napus

<400> SEQUENCE: 43
ttgtttcgct attttccgga atctcttaat tattattttt ctaaactttt tttacaaatg 60
aatttcactt tttaactcac tttctaactc acttgcttag atataaaata acgttagtgt 120
gaaagccact aagaacacat gataatggtt aactatgtcc atgaagacgt gtttgaatct 180
aattgaaaaa tccgatacac tagtatgttt tattcattta aacatattat ctgtgcaacg 240
tggtgctttc ggtttgatat gaaatggatt ccccgtattg cacgatattg attggttcaa 300
caacacaaat atgcatgact ctcacatgca tataggtata agagtcacta tgtaattttc 360
cttggtttca agttatgccc caaaataata cgtaatgtct tctaaaacca acatctaatg 420
tatgtctgta cgtgtacact gatgtatatc aactaaacaa cggacacatg tcttcataaa 480
aaaaccttaa acatgacaaa rcataagtga atagaggatg ataattattt tatttttatt 540
attagtacca cgggaaactt tgaaatcgat atactagcat gtttttcatt ttaggaaagg 600
agatactgcc atatatggag ccgagaccac cggtggggat tcaccgttac atatttgtac 660
ttttcaggca gaactcaccg gtgggtatga tggtgcagca gccgccttcg cgagccaact 720
tcagcacccg aatgttcgct ggacatctcg atcttggttt gcctgtggcc acagtttact 780
tcaacgccca gaaagagcca gcttcacgca gacgctgatg cacgcaacca aaataaaaga 840
gagagccttt tccggtttta cctaaaaacc ggaccggaaa gaaatatggg gtttatatat 900
caaaccatat tttgtatcat ccggttctcg actatatata tgtgtagatg catatacaat 960
tatacaaata tgtttatgtt tgtgtgttat attaagtggc t 1001

<210> SEQ ID NO 44
<211> LENGTH: 1001
<212> TYPE: DNA
<213> ORGANISM: Brassica napus

<400> SEQUENCE: 44
tacaaatgaa tttcactttt taactcactt tctaactcac ttgcttagat ataaaataac 60
gttagtgtga aagccactaa gaacacatga taatggttaa ctatgtccat gaagacgtgt 120
ttgaatctaa ttgaaaaatc cgatacacta gtatgtttta ttcatttaaa catattatct 180
gtgcaacgtg gtgctttcgg tttgatatga aatggattcc ccgtattgca cgatattgat 240
tggttcaaca acacaaatat gcatgactct cacatgcata taggtataag agtcactatg 300
taattttcct tggtttcaag ttatgcccca aaataatacg taatgtcttc taaaaccaac 360
atctaatgta tgtctgtacg tgtacactga tgtatatcaa ctaaacaacg gacacatgtc 420
ttcataaaaa aaccttaaac atgacaaagc ataagtgaat agaggatgat aattatttta 480
tttttattat tagtaccacg rgaaactttg aaatcgatat actagcatgt ttttcatttt 540
aggaaaggag atactgccat atatggagcc gagaccaccg gtggggattc accgttacat 600
atttgtactt ttcaggcaga actcaccggt gggtatgatg gtgcagcagc cgccttcgcg 660
agccaacttc agcacccgaa tgttcgctgg acatctcgat cttggtttgc ctgtggccac 720
agtttacttc aacgcccaga aagagccagc ttcacgcaga cgctgatgca cgcaaccaaa 780
ataaaagaga gagccttttc cggttttacc taaaaaccgg accggaaaga aatatggggt 840
ttatatatca aaccatattt tgtatcatcc ggttctcgac tatatatatg tgtagatgca 900
tatacaatta tacaaatatg tttatgtttg tgtgttatat taagtggctt gcgtataata 960
tatggttttc gttttctttt atctttaaat aaactaaaaa a 1001

```
<210> SEQ ID NO 45
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion [+/T]

<400> SEQUENCE: 45

cgcccagaaa gagccagctt cacgcagacg ctgatgcacg caaccaaaat aaaagagaga     60

gccttttccg gttttaccta aaaaccggac cggaaagaaa tatggggttt atatatcaaa    120

ccatattttg tatcatccgg ttctcgacta tatatatgtg tagatgcata tacaattata    180

caaatatgtt tatgtttgtg tgttatatta agtggcttgc gtataatata tggttttcgt    240

tttcttttat ctttaaataa actaaaaaat aaaggtatgt atcaaattat aaagaaacaa    300

gaagagagga taaacaaaaa aaatgaaaat tctagtatac tgccttatta aaaaaaaaaa    360

atactattag ttcttaaacc gaaattcaga aatataaatg tcggttacaa atttgattcg    420

aacaaaatga accatttccc gtttaaataa actagtttca accaccacat ttaagttaaa    480

atatatcata ttattaattt tnaacccaaa actcaagaat acaaatgtca gttacaagct    540

taattccaac aaaatgattt aattctaact taaataaact agcttgcttg accgccggct    600

gacttaaata aactagcttt tcttgttgat cattagcctt cttctcctct gaacctatgt    660

agcttgtttt ctaaagattt tgatccacgc actctccttg aatttcaact acatcttctg    720

tggactcata tctttccttc tctctattct cagagtcttg ttttattcca gaatcatcaa    780

agcttggaca aatcgaatgt aacttcacgt tgatccactg aaaaatcttg ttcgtaagag    840

tttggtgttg aagtaacatc tagtgcttcg ccattggttt cttagagcat gattattgca    900

aagacccata ttaggggttc ttattatttt ttaatgcttt taagtacaaa aagtgattta    960

agagacaaat ttaagaaacc ctaacattta attgctccat tg                      1002


<210> SEQ ID NO 46
<211> LENGTH: 1001
<212> TYPE: DNA
<213> ORGANISM: Brassica napus

<400> SEQUENCE: 46

agagcctttt ccggttttac ctaaaaaccg gaccggaaag aaatatgggg tttatatatc     60

aaaccatatt ttgtatcatc cggttctcga ctatatatat gtgtagatgc atatacaatt    120

atacaaatat gtttatgttt gtgtgttata ttaagtggct tgcgtataat atatggtttt    180

cgttttcttt tatctttaaa taaactaaaa aataaaggta tgtatcaaat tataaagaaa    240

caagaagaga ggataaacaa aaaaaatgaa aattctagta tactgcctta ttaaaaaaaa    300

aaaatactat tagttcttaa accgaaattc agaaatataa atgtcggtta caaatttgat    360

tcgaacaaaa tgaaccattt cccgtttaaa taaactagtt tcaaccacca catttaagtt    420

aaaatatatc atattattaa ttttaaccca aaactcaaga atacaaatgt cagttacaag    480

cttaattcca acaaaatgat ytaattctaa cttaaataaa ctagcttgct tgaccgccgg    540

ctgacttaaa taaactagct tttcttgttg atcattagcc ttcttctcct ctgaacctat    600

gtagcttgtt ttctaaagat tttgatccac gcactctcct tgaatttcaa ctacatcttc    660

tgtggactca tatctttcct tctctctatt ctcagagtct tgttttattc cagaatcatc    720

aaagcttgga caaatcgaat gtaacttcac gttgatccac tgaaaaatct tgttcgtaag    780
```

```
agtttggtgt tgaagtaaca tctagtgctt cgccattggt ttcttagagc atgattattg    840

caaagaccca tattaggggt tcttattatt ttttaatgct tttaagtaca aaaagtgatt    900

taagagacaa atttaagaaa ccctaacatt taattgctcc attgcaaggt tcttacaaca    960

ttactttcac tcttcttact tgatcttctt tagccaatgt t                       1001
```

<210> SEQ ID NO 47
<211> LENGTH: 1001
<212> TYPE: DNA
<213> ORGANISM: Brassica napus

<400> SEQUENCE: 47

```
atatggggtt tatatatcaa accatatttt gtatcatccg gttctcgact atatatatgt     60

gtagatgcat atacaattat acaaatatgt ttatgtttgt gtgttatatt aagtggcttg    120

cgtataatat atggttttcg ttttctttta tctttaaata aactaaaaaa taaaggtatg    180

tatcaaatta taaagaaaca agaagagagg ataaacaaaa aaaatgaaaa ttctagtata    240

ctgccttatt aaaaaaaaaa aatactatta gttcttaaac cgaaattcag aaatataaat    300

gtcggttaca aatttgattc gaacaaaatg aaccatttcc cgtttaaata aactagtttc    360

aaccaccaca tttaagttaa aatatatcat attattaatt ttaacccaaa actcaagaat    420

acaaatgtca gttacaagct taattccaac aaaatgattt aattctaact taaataaact    480

agcttgcttg accgccggct racttaaata aactagcttt tcttgttgat cattagcctt    540

cttctcctct gaacctatgt agcttgtttt ctaaagattt tgatccacgc actctccttg    600

aatttcaact acatcttctg tggactcata tctttccttc tctctattct cagagtcttg    660

ttttattcca gaatcatcaa agcttggaca aatcgaatgt aacttcacgt tgatccactg    720

aaaaatcttg ttcgtaagag tttggtgttg aagtaacatc tagtgcttcg ccattggttt    780

cttagagcat gattattgca aagacccata ttaggggttc ttattatttt ttaatgcttt    840

taagtacaaa aagtgattta agagacaaat ttaagaaacc ctaacattta attgctccat    900

tgcaaggttc ttacaacatt actttcactc ttcttacttg atcttcttta gccaatgttg    960

ttccaatgtc aaagacgatg aaacagaaac aagaaaacct c                       1001
```

<210> SEQ ID NO 48
<211> LENGTH: 1001
<212> TYPE: DNA
<213> ORGANISM: Brassica napus

<400> SEQUENCE: 48

```
taatatatgg ttttcgtttt cttttatctt taaataaact aaaaaataaa ggtatgtatc     60

aaattataaa gaaacaagaa gagaggataa acaaaaaaaa tgaaaattct agtatactgc    120

cttattaaaa aaaaaaaata ctattagttc ttaaaccgaa attcagaaat ataaatgtcg    180

gttacaaatt tgattcgaac aaaatgaacc atttcccgtt taaataaact agtttcaacc    240

accacattta agttaaaata tatcatatta ttaattttaa cccaaaactc aagaatacaa    300

atgtcagtta caagcttaat tccaacaaaa tgatttaatt ctaacttaaa taaactagct    360

tgcttgaccg ccggctgact taaataaact agcttttctt gttgatcatt agccttcttc    420

tcctctgaac ctatgtagct tgttttctaa agattttgat ccacgcactc tccttgaatt    480

tcaactacat cttctgtgga ytcatatctt tccttctctc tattctcaga gtcttgtttt    540

attccagaat catcaaagct tggacaaatc gaatgtaact tcacgttgat ccactgaaaa    600

atcttgttcg taagagtttg gtgttgaagt aacatctagt gcttcgccat tggtttctta    660
```

```
gagcatgatt attgcaaaga cccatattag gggttcttat tattttttaa tgcttttaag    720

tacaaaaagt gatttaagag acaaatttaa gaaaccctaa catttaattg ctccattgca    780

aggttcttac aacattactt tcactcttct tacttgatct tctttagcca atgttgttcc    840

aatgtcaaag acgatgaaac agaaacaaga aaacctcaat aaaatgaatc aataaccaga    900

accttgaaac atgaaacaaa acaacaaagc atatcattct cattactcaa acagaacaag    960

aacattaaca tgaaacagag acagaataag caaaacaacg t                       1001
```

<210> SEQ ID NO 49
<211> LENGTH: 1001
<212> TYPE: DNA
<213> ORGANISM: Brassica napus

<400> SEQUENCE: 49

```
ataaagaaac aagaagagag gataaacaaa aaaaatgaaa attctagtat actgccttat     60

taaaaaaaaa aaatactatt agttcttaaa ccgaaattca gaaatataaa tgtcggttac    120

aaatttgatt cgaacaaaat gaaccatttc ccgtttaaat aaactagttt caaccaccac    180

atttaagtta aaatatatca tattattaat tttaacccaa aactcaagaa tacaaatgtc    240

agttacaagc ttaattccaa caaaatgatt taattctaac ttaaataaac tagcttgctt    300

gaccgccggc tgacttaaat aaactagctt ttcttgttga tcattagcct tcttctcctc    360

tgaacctatg tagcttgttt tctaaagatt ttgatccacg cactctcctt gaatttcaac    420

tacatcttct gtggactcat atctttcctt ctctctattc tcagagtctt gttttattcc    480

agaatcatca aagcttggac raatcgaatg taacttcacg ttgatccact gaaaaatctt    540

gttcgtaaga gtttggtgtt gaagtaacat ctagtgcttc gccattggtt tcttagagca    600

tgattattgc aaagacccat attaggggtt cttattattt tttaatgctt ttaagtacaa    660

aaagtgattt aagagacaaa tttaagaaac cctaacattt aattgctcca ttgcaaggtt    720

cttacaacat tactttcact cttcttactt gatcttcttt agccaatgtt gttccaatgt    780

caaagacgat gaaacagaaa caagaaaacc tcaataaaat gaatcaataa ccagaacctt    840

gaaacatgaa acaaaacaac aaagcatatc attctcatta ctcaaacaga acaagaacat    900

taacatgaaa cagagacaga ataagcaaaa caacgtgtag ttccccgtac gtcttgtgca    960

gcattgtaat tcttcacgga atcagtagta aaagttattt a                       1001
```

<210> SEQ ID NO 50
<211> LENGTH: 1001
<212> TYPE: DNA
<213> ORGANISM: Brassica napus

<400> SEQUENCE: 50

```
attaaaaaaa aaaaatacta ttagttctta aaccgaaatt cagaaatata aatgtcggtt     60

acaaatttga ttcgaacaaa atgaaccatt tcccgtttaa ataaactagt ttcaaccacc    120

acatttaagt taaaatatat catattatta attttaaccc aaaactcaag aatacaaatg    180

tcagttacaa gcttaattcc aacaaaatga tttaattcta acttaaataa actagcttgc    240

ttgaccgccg gctgacttaa ataaactagc ttttcttgtt gatcattagc cttcttctcc    300

tctgaaccta tgtagcttgt tttctaaaga ttttgatcca cgcactctcc ttgaatttca    360

actacatctt ctgtggactc atatctttcc ttctctctat tctcagagtc ttgttttatt    420

ccagaatcat caaagcttgg acaaatcgaa tgtaacttca cgttgatcca ctgaaaaatc    480
```

```
ttgttcgtaa gagtttggtg ytgaagtaac atctagtgct tcgccattgg tttcttagag    540

catgattatt gcaaagaccc atattagggg ttcttattat tttttaatgc ttttaagtac    600

aaaaagtgat ttaagagaca aatttaagaa accctaacat ttaattgctc cattgcaagg    660

ttcttacaac attactttca ctcttcttac ttgatcttct ttagccaatg ttgttccaat    720

gtcaaagacg atgaaacaga aacaagaaaa cctcaataaa atgaatcaat aaccagaacc    780

ttgaaacatg aaacaaaaca acaaagcata tcattctcat tactcaaaca gaacaagaac    840

attaacatga aacagagaca gaataagcaa aacaacgtgt agttccccgt acgtcttgtg    900

cagcattgta attcttcacg gaatcagtag taaaagttat ttattaaacc gttctaacag    960

tagtaaacaa acatccaggt gctgtgaaaa aaatctatca a                       1001
```

<210> SEQ ID NO 51
<211> LENGTH: 1001
<212> TYPE: DNA
<213> ORGANISM: Brassica napus

<400> SEQUENCE: 51

```
tactattagt tcttaaaccg aaattcagaa atataaatgt cggttacaaa tttgattcga     60

acaaaatgaa ccatttcccg tttaaataaa ctagtttcaa ccaccacatt taagttaaaa    120

tatatcatat tattaatttt aacccaaaac tcaagaatac aaatgtcagt tacaagctta    180

attccaacaa aatgatttaa ttctaactta aataaactag cttgcttgac cgccggctga    240

cttaaataaa ctagcttttc ttgttgatca ttagccttct tctcctctga acctatgtag    300

cttgttttct aaagattttg atccacgcac tctccttgaa tttcaactac atcttctgtg    360

gactcatatc tttccttctc tctattctca gagtcttgtt ttattccaga atcatcaaag    420

cttggacaaa tcgaatgtaa cttcacgttg atccactgaa aaatcttgtt cgtaagagtt    480

tggtgttgaa gtaacatcta stgcttcgcc attggtttct tagagcatga ttattgcaaa    540

gacccatatt aggggttctt attatttttt aatgctttta agtacaaaaa gtgatttaag    600

agacaaattt aagaaaccct aacatttaat tgctccattg caaggttctt acaacattac    660

tttcactctt cttacttgat cttctttagc caatgttgtt ccaatgtcaa agacgatgaa    720

acagaaacaa gaaaacctca ataaaatgaa tcaataacca gaaccttgaa acatgaaaca    780

aaacaacaaa gcatatcatt ctcattactc aaacagaaca agaacattaa catgaaacag    840

agacagaata agcaaaacaa cgtgtagttc cccgtacgtc ttgtgcagca ttgtaattct    900

tcacggaatc agtagtaaaa gttatttatt aaaccgttct aacagtagta aacaaacatc    960

caggtgctgt gaaaaaaatc tatcaattga aacaacgatc t                       1001
```

<210> SEQ ID NO 52
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion [+/A]

<400> SEQUENCE: 52

```
tggtggaaga agaagactca gctttgttgt tgttgcagag ataaccgcgg ctcagaggta     60

aggacgaaga agaatgcgac agctgtctca taagagacgt cccttgcgga gccaaattaa    120

gagacgtctt ctccgtgttt tgtatttttc attttttttt aatcacaata acctaagaga    180

catgcttagg agactgcgat aatggtgctc ttacagaccc cacgacagga gggcttgttc    240
```

```
actgtattct aattggtgga aaagaaagct acgggaaaga aatactcttg tgagcacata    300
tgttgttgtt caattctaag ggcagaaacg agttgctaga gttccatttt aaccagtttc    360
tgtacacctt taaacattgt aattgttgca tacacgccag cttattaaga aaatacaaat    420
tcaagtgtga ctactctgtt ccctcatttt gataggatta tcaaagatat cacattgaaa    480
caaaacagaa gcaactaaaa ancagtaaga tctctcacaa acaatataaa agatcgaaac    540
ctagaattga cataaaacaa aacattattg caaaatctca gtttgttgac aaaacaaaag    600
tgtgatagat aaaaaacaca tccaaggaga gagacagggc aaagagatgg gataaactag    660
taacggccaa taccccaaac tctgataact ccatcggtgt atccactgaa caaggtgctt    720
ccatccgcac tccagctcag gctagtgcag taaataacct gtccaaaaaa gtaaatgttt    780
aagtctagtt tctcaatcta ggcaagaaaa aaaaacagtt cttaccaaaa tataaaaaca    840
ttcaaaaatt gccatagata gaaaaatcta tatcagatct atcgattaca ttcacatatt    900
gataaaacac tagccaacaa tatactgcaa tctatggcaa acatgtataa aagtaaattc    960
agacaaaaga acacaagaca tttgagcatc cacatgaaaa ac                      1002
```

<210> SEQ ID NO 53
<211> LENGTH: 1001
<212> TYPE: DNA
<213> ORGANISM: Brassica napus

<400> SEQUENCE: 53

```
gttgttgttg cagagataac cgcggctcag aggtaaggac gaagaagaat gcgacagctg     60
tctcataaga gacgtccctt gcggagccaa attaagagac gtcttctccg tgttttgtat    120
ttttcatttt tttttaatca caataaccta agagacatgc ttaggagact gcgataatgg    180
tgctcttaca gaccccacga caggagggct tgttcactgt attctaattg gtggaaaaga    240
aagctacggg aaagaaatac tcttgtgagc acatatgttg ttgttcaatt ctaagggcag    300
aaacgagttg ctagagttcc attttaacca gtttctgtac acctttaaac attgtaattg    360
ttgcatacac gccagcttat taagaaaata caaattcaag tgtgactact ctgttccctc    420
attttgatag gattatcaaa gatatcacat tgaaacaaaa cagaagcaac taaaaacagt    480
aagatctctc acaaacaata waaaagatcg aaacctagaa ttgacataaa acaaaacatt    540
attgcaaaat ctcagtttgt tgacaaaaca aaagtgtgat agataaaaaa cacatccaag    600
gagagagaca gggcaaagag atgggataaa ctagtaacgg ccaatacccc aaactctgat    660
aactccatcg gtgtatccac tgaacaaggt gcttccatcc gcactccagc tcaggctagt    720
gcagtaaata acctgtccaa aaaagtaaat gtttaagtct agtttctcaa tctaggcaag    780
aaaaaaaaac agttcttacc aaaatataaa aacattcaaa aattgccata gatagaaaaa    840
tctatatcag atctatcgat tacattcaca tattgataaa acactagcca acaatatact    900
gcaatctatg gcaaacatgt ataaaagtaa attcagacaa aagaacacaa gacatttgag    960
catccacatg aaaaacaaac atatttacaa aacataaaca a                       1001
```

<210> SEQ ID NO 54
<211> LENGTH: 1001
<212> TYPE: DNA
<213> ORGANISM: Brassica napus

<400> SEQUENCE: 54

```
agagacgtct tctccgtgtt ttgtattttt catttttttt taatcacaat aacctaagag     60
```

-continued

```
acatgcttag gagactgcga taatggtgct cttacagacc ccacgacagg agggcttgtt    120

cactgtattc taattggtgg aaaagaaagc tacgggaaag aaatactctt gtgagcacat    180

atgttgttgt tcaattctaa gggcagaaac gagttgctag agttccattt taaccagttt    240

ctgtacacct ttaaacattg taattgttgc atacacgcca gcttattaag aaaatacaaa    300

ttcaagtgtg actactctgt tccctcattt tgataggatt atcaaagata tcacattgaa    360

acaaaacaga agcaactaaa aacagtaaga tctctcacaa acaatataaa agatcgaaac    420

ctagaattga cataaaacaa aacattattg caaaatctca gtttgttgac aaaacaaaag    480

tgtgatagat aaaaaacaca wccaaggaga gagacagggc aaagagatgg gataaactag    540

taacggccaa taccccaaac tctgataact ccatcggtgt atccactgaa caaggtgctt    600

ccatccgcac tccagctcag gctagtgcag taaataacct gtccaaaaaa gtaaatgttt    660

aagtctagtt tctcaatcta ggcaagaaaa aaaaacagtt cttaccaaaa tataaaaaca    720

ttcaaaaatt gccatagata gaaaaatcta tatcagatct atcgattaca ttcacatatt    780

gataaaacac tagccaacaa tatactgcaa tctatggcaa acatgtataa aagtaaattc    840

agacaaaaga acacaagaca tttgagcatc cacatgaaaa acaaacatat ttacaaaaca    900

taaacaagga tataaaacca caatcataac cataagcatg catcgtttat ttgcatttca    960

atagatcaat ccaaaagaac catttctata aacactatcc t                       1001
```

<210> SEQ ID NO 55
<211> LENGTH: 1001
<212> TYPE: DNA
<213> ORGANISM: Brassica napus

<400> SEQUENCE: 55

```
gataatggtg ctcttacaga ccccacgaca ggagggcttg ttcactgtat tctaattggt     60

ggaaaagaaa gctacgggaa agaaatactc ttgtgagcac atatgttgtt gttcaattct    120

aagggcagaa acgagttgct agagttccat tttaaccagt ttctgtacac ctttaaacat    180

tgtaattgtt gcatacacgc cagcttatta agaaaataca aattcaagtg tgactactct    240

gttccctcat tttgatagga ttatcaaaga tatcacattg aaacaaaaca gaagcaacta    300

aaaacagtaa gatctctcac aaacaatata aaagatcgaa acctagaatt gacataaaac    360

aaaacattat tgcaaaatct cagtttgttg acaaaacaaa agtgtgatag ataaaaaaca    420

catccaagga gagagacagg gcaaagagat gggataaact agtaacggcc aataccccaa    480

actctgataa ctccatcggt rtatccactg aacaaggtgc ttccatccgc actccagctc    540

aggctagtgc agtaaataac ctgtccaaaa aagtaaatgt ttaagtctag tttctcaatc    600

taggcaagaa aaaaaaacag ttcttaccaa aatataaaaa cattcaaaaa ttgccataga    660

tagaaaaatc tatatcagat ctatcgatta cattcacata ttgataaaac actagccaac    720

aatatactgc aatctatggc aaacatgtat aaaagtaaat tcagacaaaa gaacacaaga    780

catttgagca tccacatgaa aaacaaacat atttacaaaa cataaacaag gatataaaac    840

cacaatcata accataagca tgcatcgttt atttgcattt caatagatca atccaaaaga    900

accatttcta taaacactat cctctatcaa cagtttacct aaactaaaga aatattatcc    960

atacaataag catcaaactt gcatgtcttt gtacctttct t                       1001
```

<210> SEQ ID NO 56
<211> LENGTH: 1001
<212> TYPE: DNA
<213> ORGANISM: Brassica napus

<400> SEQUENCE: 56

```
tgtattctaa ttggtggaaa agaaagctac gggaaagaaa tactcttgtg agcacatatg     60
ttgttgttca attctaaggg cagaaacgag ttgctagagt tccattttaa ccagtttctg    120
tacaccttta aacattgtaa ttgttgcata cacgccagct tattaagaaa atacaaattc    180
aagtgtgact actctgttcc ctcattttga taggattatc aaagatatca cattgaaaca    240
aaacagaagc aactaaaaac agtaagatct ctcacaaaca atataaaaga tcgaaaccta    300
gaattgacat aaaacaaaac attattgcaa aatctcagtt tgttgacaaa acaaaagtgt    360
gatagataaa aaacacatcc aaggagagag acagggcaaa gagatgggat aaactagtaa    420
cggccaatac cccaaactct gataactcca tcggtgtatc cactgaacaa ggtgcttcca    480
tccgcactcc agctcaggct rgtgcagtaa ataacctgtc caaaaaagta aatgtttaag    540
tctagtttct caatctaggc aagaaaaaaa aacagttctt accaaaatat aaaaacattc    600
aaaaattgcc atagatagaa aaatctatat cagatctatc gattacattc acatattgat    660
aaaacactag ccaacaatat actgcaatct atggcaaaca tgtataaaag taaattcaga    720
caaaagaaca caagacattt gagcatccac atgaaaaaca aacatattta caaaacataa    780
acaaggatat aaaaccacaa tcataaccat aagcatgcat cgtttatttg catttcaata    840
gatcaatcca aaagaaccat ttctataaac actatcctct atcaacagtt tacctaaact    900
aaagaaatat tatccataca ataagcatca aacttgcatg tctttgtacc tttcttttgg    960
tggcagcagt accacttcca tcggacttct cagcctcagc c                       1001
```

<210> SEQ ID NO 57
<211> LENGTH: 1001
<212> TYPE: DNA
<213> ORGANISM: Brassica napus

<400> SEQUENCE: 57

```
gggcagaaac gagttgctag agttccattt taaccagttt ctgtacacct ttaaacattg     60
taattgttgc atacacgcca gcttattaag aaaatacaaa ttcaagtgtg actactctgt    120
tccctcattt tgataggatt atcaaagata tcacattgaa acaaaacaga agcaactaaa    180
aacagtaaga tctctcacaa acaatataaa agatcgaaac ctagaattga cataaaacaa    240
aacattattg caaaatctca gtttgttgac aaaacaaaag tgtgatagat aaaaaacaca    300
tccaaggaga gagacagggc aaagagatgg gataaactag taacggccaa taccccaaac    360
tctgataact ccatcggtgt atccactgaa caaggtgctt ccatccgcac tccagctcag    420
gctagtgcag taaataacct gtccaaaaaa gtaaatgttt aagtctagtt tctcaatcta    480
ggcaagaaaa aaaaacagtt sttaccaaaa tataaaaaca ttcaaaaatt gccatagata    540
gaaaaatcta tatcagatct atcgattaca ttcacatatt gataaaacac tagccaacaa    600
tatactgcaa tctatggcaa acatgtataa aagtaaattc agacaaaaga acacaagaca    660
tttgagcatc cacatgaaaa acaaacatat ttacaaaaca taaacaagga tataaaacca    720
caatcataac cataagcatg catcgtttat ttgcatttca atagatcaat ccaaaagaac    780
catttctata aacactatcc tctatcaaca gtttacctaa actaaagaaa tattatccat    840
acaataagca tcaaacttgc atgtctttgt acctttcttt tggtggcagc agtaccactt    900
ccatcggact tctcagcctc agccttgaga tcaaccttca agtcctcaac aacactcttg    960
ctctcaagat cccaaatctt aataccctgc tcagtcgcag c                       1001
```

<210> SEQ ID NO 58
<211> LENGTH: 1001
<212> TYPE: DNA
<213> ORGANISM: Brassica napus

<400> SEQUENCE: 58
agaaacgagt tgctagagtt ccattttaac cagtttctgt acacctttaa acattgtaat 60
tgttgcatac acgccagctt attaagaaaa tacaaattca agtgtgacta ctctgttccc 120
tcattttgat aggattatca aagatatcac attgaaacaa aacagaagca actaaaaaca 180
gtaagatctc tcacaaacaa tataaaagat cgaaacctag aattgacata aaacaaaaca 240
ttattgcaaa atctcagttt gttgacaaaa caaaagtgtg atagataaaa aacacatcca 300
aggagagaga cagggcaaag agatgggata aactagtaac ggccaatacc ccaaactctg 360
ataactccat cggtgtatcc actgaacaag gtgcttccat ccgcactcca gctcaggcta 420
gtgcagtaaa taacctgtcc aaaaaagtaa atgtttaagt ctagtttctc aatctaggca 480
agaaaaaaaa acagttctta mcaaaatata aaaacattca aaaattgcca tagatagaaa 540
aatctatatc agatctatcg attacattca catattgata aaacactagc caacaatata 600
ctgcaatcta tggcaaacat gtataaaagt aaattcagac aaaagaacac aagacatttg 660
agcatccaca tgaaaaacaa acatatttac aaaacataaa caaggatata aaaccacaat 720
cataaccata agcatgcatc gtttatttgc atttcaatag atcaatccaa aagaaccatt 780
tctataaaca ctatcctcta tcaacagttt acctaaacta aagaaatatt atccatacaa 840
taagcatcaa acttgcatgt ctttgtacct ttcttttggt ggcagcagta ccacttccat 900
cggacttctc agcctcagcc ttgagatcaa ccttcaagtc ctcaacaaca ctcttgctct 960
caagatccca aatcttaata ccctgctcag tcgcagcaca a 1001

<210> SEQ ID NO 59
<211> LENGTH: 1001
<212> TYPE: DNA
<213> ORGANISM: Brassica napus

<400> SEQUENCE: 59
gagttgctag agttccattt taaccagttt ctgtacacct ttaaacattg taattgttgc 60
atacacgcca gcttattaag aaaatacaaa ttcaagtgtg actactctgt tccctcattt 120
tgataggatt atcaaagata tcacattgaa acaaaacaga agcaactaaa aacagtaaga 180
tctctcacaa acaatataaa agatcgaaac ctagaattga cataaaacaa aacattattg 240
caaaatctca gtttgttgac aaaacaaaag tgtgatagat aaaaaacaca tccaaggaga 300
gagacagggc aaagagatgg gataaactag taacggccaa taccccaaac tctgataact 360
ccatcggtgt atccactgaa caaggtgctt ccatccgcac tccagctcag gctagtgcag 420
taaataacct gtccaaaaaa gtaaatgttt aagtctagtt tctcaatcta ggcaagaaaa 480
aaaaacagtt cttaccaaaa yataaaaaca ttcaaaaatt gccatagata gaaaaatcta 540
tatcagatct atcgattaca ttcacatatt gataaaacac tagccaacaa tatactgcaa 600
tctatggcaa acatgtataa aagtaaattc agacaaaaga acacaagaca tttgagcatc 660
cacatgaaaa acaaacatat ttacaaaaca taaacaagga tataaaacca caatcataac 720
cataagcatg catcgtttat ttgcatttca atagatcaat ccaaaagaac catttctata 780
aacactatcc tctatcaaca gtttacctaa actaaagaaa tattatccat acaataagca 840
tcaaacttgc atgtctttgt acctttcttt tggtggcagc agtaccactt ccatcggact 900

```
tctcagcctc agccttgaga tcaaccttca agtcctcaac aacactcttg ctctcaagat    960

cccaaatctt aataccctgc tcagtcgcag cacaaagcca g                       1001


<210> SEQ ID NO 60
<211> LENGTH: 1001
<212> TYPE: DNA
<213> ORGANISM: Brassica napus

<400> SEQUENCE: 60

cacattgaaa caaaacagaa gcaactaaaa acagtaagat ctctcacaaa caatataaaa     60

gatcgaaacc tagaattgac ataaaacaaa acattattgc aaaatctcag tttgttgaca    120

aaacaaaagt gtgatagata aaaaacacat ccaaggagag agacagggca aagagatggg    180

ataaactagt aacggccaat accccaaact ctgataactc catcggtgta tccactgaac    240

aaggtgcttc catccgcact ccagctcagg ctagtgcagt aaataacctg tccaaaaaag    300

taaatgttta agtctagttt ctcaatctag gcaagaaaaa aaaacagttc ttaccaaaat    360

ataaaaacat tcaaaaattg ccatagatag aaaaatctat atcagatcta tcgattacat    420

tcacatattg ataaaacact agccaacaat atactgcaat ctatggcaaa catgtataaa    480

agtaaattca gacaaaagaa sacaagacat ttgagcatcc acatgaaaaa caaacatatt    540

tacaaaacat aaacaaggat ataaaaccac aatcataacc ataagcatgc atcgtttatt    600

tgcatttcaa tagatcaatc caaaagaacc atttctataa acactatcct ctatcaacag    660

tttacctaaa ctaaagaaat attatccata caataagcat caaacttgca tgtctttgta    720

cctttctttt ggtggcagca gtaccacttc catcggactt ctcagcctca gccttgagat    780

caaccttcaa gtcctcaaca acactcttgc tctcaagatc ccaaatctta ataccctgct    840

cagtcgcagc acaaagccag tacctattag gactaaagca aagagcgtga atcacagagt    900

tggcttcaag agagtaaagc ttcttcccct cagccaaatc ccagagcaaa acgacaccgt    960

ctttgcctcc actagcacac agagaaccat caggcgacac a                       1001


<210> SEQ ID NO 61
<211> LENGTH: 1001
<212> TYPE: DNA
<213> ORGANISM: Brassica napus

<400> SEQUENCE: 61

cattgaaaca aaacagaagc aactaaaaac agtaagatct ctcacaaaca atataaaaga     60

tcgaaaccta gaattgacat aaaacaaaac attattgcaa aatctcagtt tgttgacaaa    120

acaaaagtgt gatagataaa aaacacatcc aaggagagag acagggcaaa gagatgggat    180

aaactagtaa cggccaatac cccaaactct gataactcca tcggtgtatc cactgaacaa    240

ggtgcttcca tccgcactcc agctcaggct agtgcagtaa ataacctgtc caaaaaagta    300

aatgtttaag tctagtttct caatctaggc aagaaaaaaa aacagttctt accaaaatat    360

aaaaacattc aaaaattgcc atagatagaa aaatctatat cagatctatc gattacattc    420

acatattgat aaaacactag ccaacaatat actgcaatct atggcaaaca tgtataaaag    480

taaattcaga caaaagaaca yaagacattt gagcatccac atgaaaaaca aacatattta    540

caaaacataa acaaggatat aaaaccacaa tcataaccat aagcatgcat cgtttatttg    600

catttcaata gatcaatcca aaagaaccat ttctataaac actatcctct atcaacagtt    660

tacctaaact aaagaaatat tatccataca ataagcatca aacttgcatg tctttgtacc    720
```

```
tttcttttgg tggcagcagt accacttcca tcggacttct cagcctcagc cttgagatca    780

accttcaagt cctcaacaac actcttgctc tcaagatccc aaatcttaat accctgctca    840

gtcgcagcac aaagccagta cctattagga ctaaagcaaa gagcgtgaat cacagagttg    900

gcttcaagag agtaaagctt cttcccctca gccaaatccc agagcaaaac gacaccgtct    960

ttgcctccac tagcacacag agaaccatca ggcgacacag c                       1001
```

<210> SEQ ID NO 62
<211> LENGTH: 1002
<212> TYPE: DNA
<213> ORGANISM: Brassica napus
<220> FEATURE:
<221> NAME/KEY: misc_feature
<222> LOCATION: (502)..(502)
<223> OTHER INFORMATION: where n is an insertion/deletion [+/A]

<400> SEQUENCE: 62

```
aaaaacacat ccaaggagag agacagggca aagagatggg ataaactagt aacggccaat     60

accccaaact ctgataactc catcggtgta tccactgaac aaggtgcttc catccgcact    120

ccagctcagg ctagtgcagt aaataacctg tccaaaaaag taaatgttta agtctagttt    180

ctcaatctag gcaagaaaaa aaaacagttc ttaccaaaat ataaaaacat tcaaaaattg    240

ccatagatag aaaaatctat atcagatcta tcgattacat tcacatattg ataaaacact    300

agccaacaat atactgcaat ctatggcaaa catgtataaa agtaaattca gacaaaagaa    360

cacaagacat ttgagcatcc acatgaaaaa caaacatatt tacaaaacat aaacaaggat    420

ataaaaccac aatcataacc ataagcatgc atcgtttatt tgcatttcaa tagatcaatc    480

caaaagaacc atttctataa ancactatcc tctatcaaca gtttacctaa actaaagaaa    540

tattatccat acaataagca tcaaacttgc atgtctttgt acctttcttt tggtggcagc    600

agtaccactt ccatcggact tctcagcctc agccttgaga tcaaccttca agtcctcaac    660

aacactcttg ctctcaagat cccaaatctt aataccctgc tcagtcgcag cacaaagcca    720

gtacctatta ggactaaagc aaagagcgtg aatcacagag ttggcttcaa gagagtaaag    780

cttcttcccc tcagccaaat cccagagcaa aacgacaccg tctttgcctc cactagcaca    840

cagagaacca tcaggcgaca cagccacagt actaacgtaa ccagtgtgac cagcaagagt    900

cgacctcagc ttacagttcg acaagttcca aactttcacg gtcttgtccc acgacgccga    960

cacaatcgtc ggctggagcg tgttgggact gaacctaacg ca                      1002
```

<210> SEQ ID NO 63
<211> LENGTH: 1001
<212> TYPE: DNA
<213> ORGANISM: Brassica napus

<400> SEQUENCE: 63

```
ggccaatacc ccaaactctg ataactccat cggtgtatcc actgaacaag gtgcttccat     60

ccgcactcca gctcaggcta gtgcagtaaa taacctgtcc aaaaaagtaa atgtttaagt    120

ctagtttctc aatctaggca agaaaaaaaa acagttctta ccaaaatata aaaacattca    180

aaaattgcca tagatagaaa aatctatatc agatctatcg attacattca catattgata    240

aaacactagc caacaatata ctgcaatcta tggcaaacat gtataaaagt aaattcagac    300

aaaagaacac aagacatttg agcatccaca tgaaaaacaa acatatttac aaaacataaa    360

caaggatata aaaccacaat cataaccata agcatgcatc gtttatttgc atttcaatag    420

atcaatccaa aagaaccatt tctataaaca ctatcctcta tcaacagttt acctaaacta    480
```

```
aagaaatatt atccatacaa waagcatcaa acttgcatgt ctttgtacct ttcttttggt    540

ggcagcagta ccacttccat cggacttctc agcctcagcc ttgagatcaa ccttcaagtc    600

ctcaacaaca ctcttgctct caagatccca aatcttaata ccctgctcag tcgcagcaca    660

aagccagtac ctattaggac taaagcaaag agcgtgaatc acagagttgg cttcaagaga    720

gtaaagcttc ttcccctcag ccaaatccca gagcaaaacg acaccgtctt tgcctccact    780

agcacacaga gaaccatcag gcgacacagc cacagtacta acgtaaccag tgtgaccagc    840

aagagtcgac ctcagcttac agttcgacaa gttccaaact ttcacggtct tgtcccacga    900

cgccgacaca atcgtcggct ggagcgtgtt gggactgaac ctaacgcagc tgacccagtc    960

acggtgccct tcgcctcctt cggagattgt gtacttacac t                       1001
```

<210> SEQ ID NO 64
<211> LENGTH: 1001
<212> TYPE: DNA
<213> ORGANISM: Brassica napus

<400> SEQUENCE: 64

```
tccaaaaaag taaatgttta agtctagttt ctcaatctag gcaagaaaaa aaaacagttc     60

ttaccaaaat ataaaaacat tcaaaaattg ccatagatag aaaaatctat atcagatcta    120

tcgattacat tcacatattg ataaaacact agccaacaat atactgcaat ctatggcaaa    180

catgtataaa agtaaattca gacaaaagaa cacaagacat ttgagcatcc acatgaaaaa    240

caaacatatt tacaaaacat aaacaaggat ataaaaccac aatcataacc ataagcatgc    300

atcgtttatt tgcatttcaa tagatcaatc caaaagaacc atttctataa acactatcct    360

ctatcaacag tttacctaaa ctaaagaaat attatccata caataagcat caaacttgca    420

tgtctttgta cctttctttt ggtggcagca gtaccacttc catcggactt ctcagcctca    480

gccttgagat caaccttcaa rtcctcaaca acactcttgc tctcaagatc ccaaatctta    540

ataccctgct cagtcgcagc acaaagccag tacctattag gactaaagca aagagcgtga    600

atcacagagt tggcttcaag agagtaaagc ttcttcccct cagccaaatc ccagagcaaa    660

acgacaccgt ctttgcctcc actagcacac agagaaccat caggcgacac agccacagta    720

ctaacgtaac cagtgtgacc agcaagagtc gacctcagct tacagttcga caagttccaa    780

actttcacgg tcttgtccca cgacgccgac acaatcgtcg gctggagcgt gttgggactg    840

aacctaacgc agctgaccca gtcacggtgc ccttcgcctc cttcggagat tgtgtactta    900

cactccccca gagtgttcca gagcttgatc gtgcggtcac gggaggccga cacgatctga    960

cggttgtcga gcgagaaggc cacggagagg acgtctttgg t                       1001
```

<210> SEQ ID NO 65
<211> LENGTH: 1001
<212> TYPE: DNA
<213> ORGANISM: Brassica napus

<400> SEQUENCE: 65

```
tacctaaact aaagaaatat tatccataca ataagcatca aacttgcatg tctttgtacc     60

tttcttttgg tggcagcagt accacttcca tcggacttct cagcctcagc cttgagatca    120

accttcaagt cctcaacaac actcttgctc tcaagatccc aaatcttaat accctgctca    180

gtcgcagcac aaagccagta cctattagga ctaaagcaaa gagcgtgaat cacagagttg    240

gcttcaagag agtaaagctt cttcccctca gccaaatccc agagcaaaac gacaccgtct    300
```

```
ttgcctccac tagcacacag agaaccatca ggcgacacag ccacagtact aacgtaacca    360

gtgtgaccag caagagtcga cctcagctta cagttcgaca agttccaaac tttcacggtc    420

ttgtcccacg acgccgacac aatcgtcggc tggagcgtgt tgggactgaa cctaacgcag    480

ctgacccagt cacggtgccc ytcgcctcct tcggagattg tgtacttaca ctcccccaga    540

gtgttccaga gcttgatcgt gcggtcacgg gaggccgaca cgatctgacg gttgtcgagc    600

gagaaggcca cggagaggac gtctttggtg tgtccgacga atctgcgagt ggagacgccg    660

gcggcgaggt cccagagacg aagctcgccg tcccagctgc cggaaagcgc gaattggccg    720

tcggaggaga ggacgacgtc ttcgacgaag tgggagtggc cggtgaggcg tctctgggct    780

acgccgtagg atttgtcgtc ctttgtgagt ttccagacga tgatggattt gtcgcgggaa    840

gcggacacga tggtgtcgga gttgtcgatg gggtggcga ttgcggtgac catgtcggtg    900

tgagcacgca tggtgccctt gaggacgagt ccttccgcca ttgtcgaagt ctggtgaagc    960

ttagggttat cagtttctcg gggaggcgg agattcagac g                        1001
```

<210> SEQ ID NO 66
<211> LENGTH: 1001
<212> TYPE: DNA
<213> ORGANISM: Brassica napus

<400> SEQUENCE: 66

```
acaataagca tcaaacttgc atgtctttgt acctttcttt tggtggcagc agtaccactt     60

ccatcggact tctcagcctc agccttgaga tcaaccttca agtcctcaac aacactcttg    120

ctctcaagat cccaaatctt aataccctgc tcagtcgcag cacaaagcca gtacctatta    180

ggactaaagc aaagagcgtg aatcacagag ttggcttcaa gagagtaaag cttcttcccc    240

tcagccaaat cccagagcaa aacgacaccg tctttgcctc cactagcaca cagagaacca    300

tcaggcgaca cagccacagt actaacgtaa ccagtgtgac cagcaagagt cgacctcagc    360

ttacagttcg acaagttcca aactttcacg gtcttgtccc acgacgccga cacaatcgtc    420

ggctggagcg tgttgggact gaacctaacg cagctgaccc agtcacggtg cccttcgcct    480

ccttcggaga ttgtgtactt rcactccccc agagtgttcc agagcttgat cgtgcggtca    540

cgggaggccg acacgatctg acggttgtcg agcgagaagg ccacggagag gacgtctttg    600

gtgtgtccga cgaatctgcg agtggagacg ccggcggcga ggtcccagag acgaagctcg    660

ccgtcccagc tgccggaaag cgcgaattgg ccgtcggagg agaggacgac gtcttcgacg    720

aagtgggagt ggccggtgag gcgtctctgg gctacgccgt aggatttgtc gtcctttgtg    780

agtttccaga cgatgatgga tttgtcgcgg gaagcggaca cgatggtgtc ggagttgtcg    840

atgggggtgg cgattgcggt gaccatgtcg gtgtgagcac gcatggtgcc cttgaggacg    900

agtccttccg ccattgtcga agtctggtga agcttagggt tatcagtttc tcgggggagg    960

cggagattca gacgaaatgg cgtcgagagg taagattcag t                        1001
```

<210> SEQ ID NO 67
<211> LENGTH: 1001
<212> TYPE: DNA
<213> ORGANISM: Brassica napus

<400> SEQUENCE: 67

```
tcagcctcag ccttgagatc aaccttcaag tcctcaacaa cactcttgct ctcaagatcc     60

caaatcttaa taccctgctc agtcgcagca caaagccagt acctattagg actaaagcaa    120

agagcgtgaa tcacagagtt ggcttcaaga gagtaaagct tcttcccctc agccaaatcc    180
```

```
cagagcaaaa cgacaccgtc tttgcctcca ctagcacaca gagaaccatc aggcgacaca    240

gccacagtac taacgtaacc agtgtgacca gcaagagtcg acctcagctt acagttcgac    300

aagttccaaa ctttcacggt cttgtcccac gacgccgaca caatcgtcgg ctggagcgtg    360

ttgggactga acctaacgca gctgacccag tcacggtgcc cttcgcctcc ttcggagatt    420

gtgtacttac actcccccag agtgttccag agcttgatcg tgcggtcacg ggaggccgac    480

acgatctgac ggttgtcgag sgagaaggcc acggagagga cgtctttggt gtgtccgacg    540

aatctgcgag tggagacgcc ggcggcgagg tcccagagac gaagctcgcc gtcccagctg    600

ccggaaagcg cgaattggcc gtcggaggag aggacgacgt cttcgacgaa gtgggagtgg    660

ccggtgaggc gtctctgggc tacgccgtag gatttgtcgt cctttgtgag tttccagacg    720

atgatggatt tgtcgcggga agcggacacg atggtgtcgg agttgtcgat gggggtggcg    780

attgcggtga ccatgtcggt gtgagcacgc atggtgccct tgaggacgag tccttccgcc    840

attgtcgaag tctggtgaag cttagggtta tcagtttctc gggggaggcg gagattcaga    900

cgaaatggcg tcgagaggta agattcagtt tatatcagag acaacacaat ggattagggt    960

ttacttttat tggctttga tgattaagtt taatgaatgg g                        1001
```

<210> SEQ ID NO 68
<211> LENGTH: 1001
<212> TYPE: DNA
<213> ORGANISM: Brassica napus

<400> SEQUENCE: 68

```
tacctattag gactaaagca aagagcgtga atcacagagt tggcttcaag agagtaaagc     60

ttcttcccct cagccaaatc ccagagcaaa acgacaccgt ctttgcctcc actagcacac    120

agagaaccat caggcgacac agccacagta ctaacgtaac cagtgtgacc agcaagagtc    180

gacctcagct tacagttcga caagttccaa actttcacgg tcttgtccca cgacgccgac    240

acaatcgtcg gctggagcgt gttgggactg aacctaacgc agctgaccca gtcacggtgc    300

ccttcgcctc cttcggagat tgtgtactta cactccccca gagtgttcca gagcttgatc    360

gtgcggtcac gggaggccga cacgatctga cggttgtcga gcgagaaggc cacggagagg    420

acgtctttgg tgtgtccgac gaatctgcga gtggagacgc cggcggcgag gtcccagaga    480

cgaagctcgc cgtcccagct kccggaaagc gcgaattggc cgtcggagga gaggacgacg    540

tcttcgacga agtgggagtg gccggtgagg cgtctctggg ctacgccgta ggatttgtcg    600

tcctttgtga gtttccagac gatgatggat ttgtcgcggg aagcggacac gatggtgtcg    660

gagttgtcga tgggggtggc gattgcggtg accatgtcgg tgtgagcacg catggtgccc    720

ttgaggacga gtccttccgc cattgtcgaa gtctggtgaa gcttagggtt atcagtttct    780

cgggggaggc ggagattcag acgaaatggc gtcgagaggt aagattcagt ttatatcaga    840

gacaacacaa tggattaggg tttactttta ttggctttg atgattaagt ttaatgaatg    900

ggtcttgcgt aaatgggctt tttttgtact ggtaagagtt tttttggttt tacttggtgt    960

taagaattta ccaatgttcg agaatcggta actagactag c                       1001
```

<210> SEQ ID NO 69
<211> LENGTH: 1001
<212> TYPE: DNA
<213> ORGANISM: Brassica napus

<400> SEQUENCE: 69
cctccactag cacacagaga accatcaggc gacacagcca cagtactaac gtaaccagtg 60
tgaccagcaa gagtcgacct cagcttacag ttcgacaagt tccaaacttt cacggtcttg 120
tcccacgacg ccgacacaat cgtcggctgg agcgtgttgg gactgaacct aacgcagctg 180
acccagtcac ggtgcccttc gcctccttcg gagattgtgt acttacactc ccccagagtg 240
ttccagagct tgatcgtgcg gtcacgggag gccgacacga tctgacggtt gtcgagcgag 300
aaggccacgg agaggacgtc tttggtgtgt ccgacgaatc tgcgagtgga gacgccggcg 360
gcgaggtccc agagacgaag ctcgccgtcc cagctgccgg aaagcgcgaa ttggccgtcg 420
gaggagagga cgacgtcttc gacgaagtgg gagtggccgg tgaggcgtct ctgggctacg 480
ccgtaggatt tgtcgtcctt kgtgagtttc cagacgatga tggatttgtc gcgggaagcg 540
gacacgatgg tgtcggagtt gtcgatgggg gtggcgattg cggtgaccat gtcggtgtga 600
gcacgcatgg tgcccttgag gacgagtcct tccgccattg tcgaagtctg gtgaagctta 660
gggttatcag tttctcgggg gaggcggaga ttcagacgaa atggcgtcga gaggtaagat 720
tcagtttata tcagagacaa cacaatggat tagggtttac ttttattggg ctttgatgat 780
taagtttaat gaatgggtct tgcgtaaatg ggcttttttt gtactggtaa gagttttttt 840
ggttttactt ggtgttaaga atttaccaat gttcgagaat cggtaactag actagcgcct 900
agacggatta ttcagaacct aaacgagatc tagatattaa cgaattatta atttatttta 960
tatttatata aaacatttta atttttaatt ataaaattat t 1001

<210> SEQ ID NO 70
<211> LENGTH: 1001
<212> TYPE: DNA
<213> ORGANISM: Brassica napus

<400> SEQUENCE: 70
gattcggcag gttattcctg aagatgacaa gcttaatcat cttttttttg tttcgcattg 60
gtgctaaatg tttgtgttga tatatgctgc agaagaaaac aacggagttg ttatcccgga 120
agctcataac tctgatgaag ttgagaaatt ggatacagca gaagaaggtt cattgtagca 180
tgagcatgac atttttttgt ttatgctttc tttgttacac tgtttaaaat ttggctatct 240
gtgggtcgtt tattagatgc gtaagacatt aactagtggt taagggaggg ttatactatc 300
atgagattgg atactgattc taatactagg tatcatcctt gctttgcaga cctgaaagac 360
aaggtggaag agtcagcacc ggttcctgat gagcaacaag gttcaatctt ttatcttctc 420
tttctgtctc atttttctta acgtttagtt taatatatct gagtttggcg agttttattt 480
atttttgctt gtcattggtg rtttcagtgt ccgaggatca tgatcaagaa gtgcaccatg 540
cagtgcataa cccagcgaaa ggttcataga tctctcattc tacagtcttc tcatcttatg 600
agcgttcatg ttgtctggtt gaagatttat ttatctcttt cgtatatttt atccattcag 660
ctaaagagaa ggcagcccaa gagaaggctg ccaaagagga agctgaagaa gaggcagaag 720
caaacaagaa aagacacttg aacgtggtgt tcatcgggca tgttggtatg gctacttgtt 780
gatttctttt catcagctct actttcataa tagatatatc atctgcactt gtttagactc 840
agggcttaaa agcgtatgta acacattctt gaaattagga tcatgagctt ttagtcggtg 900
tgttttaact tttaagcttc ttgatttaat ctttacatgg tcaccttttc aattgtagat 960
gctggaaagt ctacaattgg aggacaaatt ctcttcctta g 1001

<210> SEQ ID NO 71
<211> LENGTH: 121

<212> TYPE: DNA
<213> ORGANISM: Brassica napus

<400> SEQUENCE: 71
acrtttagtt taatatatct gagtttggcg agttttattt atttttgctt gtcattggtg 60
rtttcagykt ccgaggatca tgatcwagaa gtgcaccatg cagtgcataa cccagcgaaa 120
g 121

<210> SEQ ID NO 72
<211> LENGTH: 1001
<212> TYPE: DNA
<213> ORGANISM: Brassica napus

<400> SEQUENCE: 72
gaacgtggtg ttcatcgggc atgttggtat ggctacttgt tgatttcttt tcatcagctc 60
tactttcata atagatatat catctgcact tgtttagact cagggcttaa aagcgtatgt 120
aacacattct tgaaattagg atcatgagct tttagtcggt gtgttttaac ttttaagctt 180
cttgatttaa tctttacatg gtcacctttt caattgtaga tgctggaaag tctacaattg 240
gaggacaaat tctcttcctt agcggtcagg tggacgaccg acaaatccaa aagtatgaaa 300
aagaagcaaa agaaaaaagt agagaaagct ggtgggtggt tctgattaat ttgaaatgat 360
aaggaattct tttgttctct ttttcttttt gtttttataa acttgttatc gttctgtatg 420
ctaggtatat ggcttatata atggatacaa atgaagaaga gagggcgaag gtatttcctg 480
atttttattt tatgtttctt wgtgtgctat aaatgtgtca gagatgataa gaattcacgt 540
gtctgtagaa ttttcagcaa tgtttatggt tgaatttaac ttagctaact gttatgactt 600
acttgctaca ttgaacaggg caaaacagtt gaagttggaa gggctcattt tgaaactgcg 660
agtacgagat ttaccatttt ggatgctccg gtaagagacc aacttaaaag aataattttt 720
tgttcacttg tctttatgag agtattttgt tctaattctt ttgcgccttt tttgaacttg 780
tagggtcaca agagttatgt accaaatatg attagtggag catctcaagc ggacattggt 840
gtactggtaa gttattatct taatttggtc ggagtcgtta ctgtgtagtg tgcgtctttg 900
gtaggaagct tattaatttt catgtccttg tccctctgtt gtaggtgatt tcggctcgta 960
aaggtgaatt tgaaacggga tatgagaggg gtgggcagac c 1001

<210> SEQ ID NO 73
<211> LENGTH: 1001
<212> TYPE: DNA
<213> ORGANISM: Brassica napus

<400> SEQUENCE: 73
ctacttgttg atttcttttc atcagctcta ctttcataat agatatatca tctgcacttg 60
tttagactca gggcttaaaa gcgtatgtaa cacattcttg aaattaggat catgagcttt 120
tagtcggtgt gttttaactt ttaagcttct tgatttaatc tttacatggt caccttttca 180
attgtagatg ctggaaagtc tacaattgga ggacaaattc tcttccttag cggtcaggtg 240
gacgaccgac aaatccaaaa gtatgaaaaa gaagcaaaag aaaaaagtag agaaagctgg 300
tgggtggttc tgattaattt gaaatgataa ggaattcttt tgttctcttt ttctttttgt 360
ttttataaac ttgttatcgt tctgtatgct aggtatatgg cttatataat ggatacaaat 420
gaagaagaga gggcgaaggt atttcctgat tttttattta tgtttcttag tgtgctataa 480
atgtgtcaga gatgataaga rttcacgtgt ctgtagaatt ttcagcaatg tttatggttg 540

-continued

```
aatttaactt agctaactgt tatgacttac ttgctacatt gaacagggca aaacagttga    600

agttggaagg gctcattttg aaactgcgag tacgagattt accattttgg atgctccggt    660

aagagaccaa cttaaaagaa taattttttg ttcacttgtc tttatgagag tattttgttc    720

taattctttt gcgccttttt tgaacttgta gggtcacaag agttatgtac caaatatgat    780

tagtggagca tctcaagcgg acattggtgt actggtaagt tattatctta atttggtcgg    840

agtcgttact gtgtagtgtg cgtctttggt aggaagctta ttaattttca tgtccttgtc    900

cctctgttgt aggtgatttc ggctcgtaaa ggtgaatttg aaacgggata tgagaggggt    960

gggcagaccc gtgaacatgt tcaacttgca aaaacattgg g                      1001
```

<210> SEQ ID NO 74
<211> LENGTH: 1001
<212> TYPE: DNA
<213> ORGANISM: Brassica napus

<400> SEQUENCE: 74

```
tcagctctac tttcataata gatatatcat ctgcacttgt ttagactcag ggcttaaaag     60

cgtatgtaac acattcttga aattaggatc atgagctttt agtcggtgtg ttttaacttt    120

taagcttctt gatttaatct ttacatggtc accttttcaa ttgtagatgc tggaaagtct    180

acaattggag gacaaattct cttccttagc ggtcaggtgg acgaccgaca aatccaaaag    240

tatgaaaaag aagcaaaaga aaaaagtaga gaaagctggt gggtggttct gattaatttg    300

aaatgataag gaattctttt gttctctttt tctttttgtt tttataaact tgttatcgtt    360

ctgtatgcta ggtatatggc ttatataatg gatacaaatg aagaagagag ggcgaaggta    420

tttcctgatt ttttatttat gtttcttagt gtgctataaa tgtgtcagag atgataagaa    480

ttcacgtgtc tgtagaattt ycagcaatgt ttatggttga atttaactta gctaactgtt    540

atgacttact tgctacattg aacagggcaa aacagttgaa gttggaaggg ctcattttga    600

aactgcgagt acgagattta ccattttgga tgctccggta agagaccaac ttaaaagaat    660

aattttttgt tcacttgtct ttatgagagt attttgttct aattcttttg cgcctttttt    720

gaacttgtag ggtcacaaga gttatgtacc aaatatgatt agtggagcat ctcaagcgga    780

cattggtgta ctggtaagtt attatcttaa tttggtcgga gtcgttactg tgtagtgtgc    840

gtctttggta ggaagcttat taattttcat gtccttgtcc ctctgttgta ggtgatttcg    900

gctcgtaaag gtgaatttga aacgggatat gagaggggtg ggcagacccg tgaacatgtt    960

caacttgcaa aaacattggg cgtgtcgaag ctggttgtcg t                      1001
```

<210> SEQ ID NO 75
<211> LENGTH: 1001
<212> TYPE: DNA
<213> ORGANISM: Brassica napus

<400> SEQUENCE: 75

```
gctctacttt cataatagat atatcatctg cacttgttta gactcagggc ttaaaagcgt     60

atgtaacaca ttcttgaaat taggatcatg agcttttagt cggtgtgttt taacttttaa    120

gcttcttgat ttaatcttta catggtcacc ttttcaattg tagatgctgg aaagtctaca    180

attggaggac aaattctctt ccttagcggt caggtggacg accgacaaat ccaaaagtat    240

gaaaaagaag caaaagaaaa aagtagagaa agctggtggg tggttctgat taatttgaaa    300

tgataaggaa ttcttttgtt ctctttttct ttttgttttt ataaacttgt tatcgttctg    360

tatgctaggt atatggctta tataatggat acaaatgaag aagagagggc gaaggtattt    420
```

cctgatttt tatttatgtt tcttagtgtg ctataaatgt gtcagagatg ataagaattc 480
acgtgtctgt agaattttca rcaatgttta tggttgaatt taacttagct aactgttatg 540
acttacttgc tacattgaac agggcaaaac agttgaagtt ggaagggctc attttgaaac 600
tgcgagtacg agatttacca ttttggatgc tccggtaaga gaccaactta aaagaataat 660
tttttgttca cttgtcttta tgagagtatt ttgttctaat tcttttgcgc cttttttgaa 720
cttgtagggt cacaagagtt atgtaccaaa tatgattagt ggagcatctc aagcggacat 780
tggtgtactg gtaagttatt atcttaattt ggtcggagtc gttactgtgt agtgtgcgtc 840
tttggtagga agcttattaa ttttcatgtc cttgtccctc tgttgtaggt gatttcggct 900
cgtaaaggtg aatttgaaac gggatatgag aggggtgggc agacccgtga acatgttcaa 960
cttgcaaaaa cattgggcgt gtcgaagctg gttgtcgttg t 1001

<210> SEQ ID NO 76
<211> LENGTH: 1001
<212> TYPE: DNA
<213> ORGANISM: Brassica napus

<400> SEQUENCE: 76
ggtcaccttt tcaattgtag atgctggaaa gtctacaatt ggaggacaaa ttctcttcct 60
tagcggtcag gtggacgacc gacaaatcca aaagtatgaa aaagaagcaa aagaaaaaag 120
tagagaaagc tggtgggtgg ttctgattaa tttgaaatga taaggaattc ttttgttctc 180
tttttctttt tgtttttata aacttgttat cgttctgtat gctaggtata tggcttatat 240
aatggataca aatgaagaag agagggcgaa ggtatttcct gattttttat ttatgtttct 300
tagtgtgcta taaatgtgtc agagatgata agaattcacg tgtctgtaga attttcagca 360
atgtttatgg ttgaatttaa cttagctaac tgttatgact tacttgctac attgaacagg 420
gcaaaacagt tgaagttgga agggctcatt ttgaaactgc gagtacgaga tttaccattt 480
tggatgctcc ggtaagagac maacttaaaa gaataatttt ttgttcactt gtctttatga 540
gagtattttg ttctaattct tttgcgcctt ttttgaactt gtagggtcac aagagttatg 600
taccaaatat gattagtgga gcatctcaag cggacattgg tgtactggta agttattatc 660
ttaatttggt cggagtcgtt actgtgtagt gtgcgtcttt ggtaggaagc ttattaattt 720
tcatgtcctt gtccctctgt tgtaggtgat ttcggctcgt aaaggtgaat ttgaaacggg 780
atatgagagg ggtgggcaga cccgtgaaca tgttcaactt gcaaaaacat tgggcgtgtc 840
gaagctggtt gtcgttgtga acaaaatgga tgatccaact gtgaactggt cgaaagagag 900
gtatgtgcat tatcctttcg aattcatgct actgtttttc gtatctactt ccattcatcc 960
gcgtatgtac tcttgtgcag gtacgatgaa atagaacaaa a 1001

<210> SEQ ID NO 77
<211> LENGTH: 1001
<212> TYPE: DNA
<213> ORGANISM: Brassica napus

<400> SEQUENCE: 77
tcaattgtag atgctggaaa gtctacaatt ggaggacaaa ttctcttcct tagcggtcag 60
gtggacgacc gacaaatcca aaagtatgaa aaagaagcaa aagaaaaaag tagagaaagc 120
tggtgggtgg ttctgattaa tttgaaatga taaggaattc ttttgttctc tttttctttt 180
tgtttttata aacttgttat cgttctgtat gctaggtata tggcttatat aatggataca 240

```
aatgaagaag agagggcgaa ggtatttcct gatttttat ttatgtttct tagtgtgcta    300
taaatgtgtc agagatgata agaattcacg tgtctgtaga attttcagca atgtttatgg    360
ttgaatttaa cttagctaac tgttatgact tacttgctac attgaacagg gcaaaacagt    420
tgaagttgga agggctcatt ttgaaactgc gagtacgaga tttaccattt tggatgctcc    480
ggtaagagac caacttaaaa saataatttt ttgttcactt gtctttatga gagtattttg    540
ttctaattct tttgcgcctt ttttgaactt gtagggtcac aagagttatg taccaaatat    600
gattagtgga gcatctcaag cggacattgg tgtactggta agttattatc ttaatttggt    660
cggagtcgtt actgtgtagt gtgcgtcttt ggtaggaagc ttattaattt tcatgtcctt    720
gtccctctgt tgtaggtgat ttcggctcgt aaaggtgaat ttgaaacggg atatgagagg    780
ggtgggcaga cccgtgaaca tgttcaactt gcaaaaacat tgggcgtgtc gaagctggtt    840
gtcgttgtga acaaaatgga tgatccaact gtgaactggt cgaaagagag gtatgtgcat    900
tatcctttcg aattcatgct actgtttttc gtatctactt ccattcatcc gcgtatgtac    960
tcttgtgcag gtacgatgaa atagaacaaa aaatggtacc a                      1001
```

<210> SEQ ID NO 78
<211> LENGTH: 1001
<212> TYPE: DNA
<213> ORGANISM: Brassica napus

<400> SEQUENCE: 78

```
aaagtctaca attggaggac aaattctctt ccttagcggt caggtggacg accgacaaat     60
ccaaaagtat gaaaaagaag caaaagaaaa aagtagagaa agctggtggg tggttctgat    120
taatttgaaa tgataaggaa ttcttttgtt ctctttttct ttttgttttt ataaacttgt    180
tatcgttctg tatgctaggt atatggctta tataatggat acaaatgaag aagagagggc    240
gaaggtattt cctgattttt tatttatgtt tcttagtgtg ctataaatgt gtcagagatg    300
ataagaattc acgtgtctgt agaattttca gcaatgttta tggttgaatt taacttagct    360
aactgttatg acttacttgc tacattgaac agggcaaaac agttgaagtt ggaagggctc    420
attttgaaac tgcgagtacg agatttacca ttttggatgc tccggtaaga gaccaactta    480
aaagaataat tttttgttca yttgtcttta tgagagtatt ttgttctaat tcttttgcgc    540
ctttttttgaa cttgtagggt cacaagagtt atgtaccaaa tatgattagt ggagcatctc    600
aagcggacat tggtgtactg gtaagttatt atcttaattt ggtcggagtc gttactgtgt    660
agtgtgcgtc tttggtagga agcttattaa ttttcatgtc cttgtccctc tgttgtaggt    720
gatttcggct cgtaaaggtg aatttgaaac gggatatgag aggggtgggc agacccgtga    780
acatgttcaa cttgcaaaaa cattgggcgt gtcgaagctg gttgtcgttg tgaacaaaat    840
ggatgatcca actgtgaact ggtcgaaaga gaggtatgtg cattatcctt tcgaattcat    900
gctactgttt ttcgtatcta cttccattca tccgcgtatg tactcttgtg caggtacgat    960
gaaatagaac aaaaaatggt accatttctt aaatcctctg g                      1001
```

<210> SEQ ID NO 79
<211> LENGTH: 1001
<212> TYPE: DNA
<213> ORGANISM: Brassica napus

<400> SEQUENCE: 79

```
ctcttcctta gcggtcaggt ggacgaccga caaatccaaa agtatgaaaa agaagcaaaa     60
gaaaaaagta gagaaagctg gtgggtggtt ctgattaatt tgaaatgata aggaattctt    120
```

```
ttgttctctt tttctttttg tttttataaa cttgttatcg ttctgtatgc taggtatatg    180

gcttatataa tggatacaaa tgaagaagag agggcgaagg tatttcctga tttttttattt    240

atgtttctta gtgtgctata aatgtgtcag agatgataag aattcacgtg tctgtagaat    300

tttcagcaat gtttatggtt gaatttaact tagctaactg ttatgactta cttgctacat    360

tgaacagggc aaaacagttg aagttggaag ggctcatttt gaaactgcga gtacgagatt    420

taccattttg gatgctccgg taagagacca acttaaaaga ataatttttt gttcacttgt    480

ctttatgaga gtattttgtt ytaattcttt tgcgcctttt ttgaacttgt agggtcacaa    540

gagttatgta ccaaatatga ttagtggagc atctcaagcg gacattggtg tactggtaag    600

ttattatctt aatttggtcg gagtcgttac tgtgtagtgt gcgtctttgg taggaagctt    660

attaattttc atgtccttgt ccctctgttg taggtgattt cggctcgtaa aggtgaattt    720

gaaacgggat atgagagggg tgggcagacc cgtgaacatg ttcaacttgc aaaaacattg    780

ggcgtgtcga agctggttgt cgttgtgaac aaaatggatg atccaactgt gaactggtcg    840

aaagagaggt atgtgcatta tcctttcgaa ttcatgctac tgtttttcgt atctacttcc    900

attcatccgc gtatgtactc ttgtgcaggt acgatgaaat agaacaaaaa atggtaccat    960

ttcttaaatc ctctggctac aacacaaaga aaggtatgca g                       1001
```

<210> SEQ ID NO 80
<211> LENGTH: 760
<212> TYPE: DNA
<213> ORGANISM: Brassica napus

<400> SEQUENCE: 80

```
aattcttttg ttctcttttt ctttttgttt ttataaactt gttatcgtct tgtatgctag     60

gtatatggct tatataatgg atacaaatga agaagagagg gcgaaggtat ttcctgattt    120

ttttatttat gtttctttgt gtgctataaa tgtgtcagag atgataagag ttcacgtgtc    180

tgtagaattt tcagcaatgt ttatggttga atttaactta gctaactgtt atgacttact    240

tgctacattg aacagggcaa aacagttgaa gttggaaggg ctcattttga aactgcgagt    300

acgagattta ccattttgga tgctccggta agagacmaac ttaaaasaat aatttttttgt    360

tcacttgtct ttatgagagt attttgttct aattcttttg cgcctttttt gaacttgtag    420

ggtcacaaga gttatgtacc aaatatgatt agtggagcat ctcaagcgga cattggtgta    480

ctggtaagtt attatcttaa tttggtcgga gtcgttactg tgtagtgtgc gtctttggta    540

ggaagcttat taattttcat gtccttgtcc ctctgttgta ggtgatttcg gctcgtaaag    600

gtgaatttga aacgggatat gagaggggtg ggcagacccg tgaacatgtt caacttgcaa    660

aaacattggg cgtgtcgaag ctggttgtcg ttgtgaacaa aatggatgat ccaactgtga    720

actggtcgaa agagaggtat gtgcattatc ctttcgaatt                          760
```

<210> SEQ ID NO 81
<211> LENGTH: 201
<212> TYPE: DNA
<213> ORGANISM: Brassica napus

<400> SEQUENCE: 81

```
ccagakgcaa aacygaatgt aagagaacat tactattaga aatcgagatc aagcttcctc     60

ttcagatgag atctatcggc actacaaaat gaacaacaac ragaagcttt taaaacacat    120

wcaakcttga gmctgtaaaa acaactaatc aaagagatcg ctctatttgc wcmtggtgat    180
```

```
ggttggtcgg kkaggaggcc g                                          201


<210> SEQ ID NO 82
<211> LENGTH: 121
<212> TYPE: DNA
<213> ORGANISM: Brassica napus

<400> SEQUENCE: 82

yagaaactgg tcgatgaggt aaccatgtgc accgtgaacc tccaccccat caaagcctat     60

rawtamcaca agtgtcatgt tcagctaaca tyatacatcc aaaggggaaa aagacttttc    120

t                                                                    121


<210> SEQ ID NO 83
<211> LENGTH: 121
<212> TYPE: DNA
<213> ORGANISM: Brassica napus

<400> SEQUENCE: 83

ratgcatttt cttcatcatt ggtaacatgg tgctttatgt yaacaataaa acctcttaat     60

ragctctaac tgattcgtaa tgaaaccaaa catatataaa taaacaatct tagatttgat    120

g                                                                    121


<210> SEQ ID NO 84
<211> LENGTH: 121
<212> TYPE: DNA
<213> ORGANISM: Brassica napus

<400> SEQUENCE: 84

gtcttttatc ttatttcaaa atatattagg tgtgacatgt gaaaaggttc tagaaactgg     60

ktggttatgc ttcctagact ccatcaagaa ataaagctga attgtttttt tacmcatcca    120

c                                                                    121


<210> SEQ ID NO 85
<211> LENGTH: 121
<212> TYPE: DNA
<213> ORGANISM: Brassica napus

<400> SEQUENCE: 85

aaactggktg gttatgcttc ctagactcca tcaagaaata aagctgaatt gtttttttac     60

mcatccactc atttttkatc aaacaggtac aagagaagaa gatcaagaaa atttctgaaa    120

t                                                                    121


<210> SEQ ID NO 86
<211> LENGTH: 121
<212> TYPE: DNA
<213> ORGANISM: Brassica napus

<400> SEQUENCE: 86

yactgcgata tcatctccta ttatacycca tgtttctttg aagaactctg ysgtataacc     60

rtctggccct ggagctttgc ttcctggcat cttaaataaa actcctttga tttcttcttt    120

r                                                                    121


<210> SEQ ID NO 87
<211> LENGTH: 121
<212> TYPE: DNA
<213> ORGANISM: Brassica napus

<400> SEQUENCE: 87
```

```
attattagtt tttccaaaat caaatgttat tagattgtac atataaaaaa aaacctaaga     60

raaaamaact catctcattc ttttatacta agakggtcta aagaaattaa tgatataaaa    120

a                                                                    121


<210> SEQ ID NO 88
<211> LENGTH: 1001
<212> TYPE: DNA
<213> ORGANISM: Brassica napus

<400> SEQUENCE: 88

ctatgtgtag tagataaagt atggtactga ccataggtat gtgacatttt agtttatatt     60

gaatgttaat atttgatatt gtatgctaac tataaacaca tgtgttattt taatagttga    120

accacaacca aagtcagcct ctatacatga ttacatccag ctggagatta catgacacat    180

gcaccagagg catacacact tggatctcta atcctaacac ctccaattac aggccaaaga    240

agacaaggat gttgttaaaa ggtgaattca aggtagacct aagctaactt cagctgatac    300

tgaacttgca ctgatgtgat tgttattaat atcattaatc gttattgaaa gttctcaaca    360

tcaaattgat tgttcatgaa acaaggtgtc atagggtgaa gagaaagaac ctgtaggaag    420

tgtggtgaaa ctgatcacag tcgcgctctc tgcaaaataa tgtataacac tattacttag    480

cggttacaca ttagttttga rccttgaagt tcacttgaaa acacgtagga gagaagcaaa    540

tagaacagcc actagcgtga tgcagatagg aatgcctata aacatgtgtg cagttgtatt    600

cttgagaagg tggatgatat ggcagatcct tgtggcttga tgattcagta cataaaaggg    660

catatcagtt tctttgaaaa aggttctttg ttgtacctat aaaagaaagg agattgtttc    720

aaaaaagaac tacataaatc atgctagaga ctggatccag agtataaata ttcacctctt    780

cgtttggttt gtccctaaaa tgttctacag aatcagcttc ttcaagggaa tcacatccgt    840

gtgcatcaag aaactgtaga ctcagtggga gtttttccac tgatctgaga ttcttgcagt    900

tattaaggca aagagttacc agtgaggtaa gatctctgat gcttgatggc aatgcaacaa    960

actcatggcc gctgagatct aaatttgtca acttaatgaa a                       1001


<210> SEQ ID NO 89
<211> LENGTH: 201
<212> TYPE: DNA
<213> ORGANISM: Brassica napus

<400> SEQUENCE: 89

gagaaagaac ctgtaggaag tgtggtgaaa ctgatcacag tcgcgctctc tgcaaaataa     60

tgtataacac tattacttag cggttacaca ttagttttga rccttgaagt tcacttgaaa    120

acacgtagra gagaagcaam tagaacagcs actagcgtga tgcagatagg aatgcctata    180

aacatgwgtg cagttgtatt c                                              201


<210> SEQ ID NO 90
<211> LENGTH: 301
<212> TYPE: DNA
<213> ORGANISM: Brassica napus

<400> SEQUENCE: 90

aatggaactt cagttgataa tggagtwtat gaaggargga acacttgaag tcttccctgt     60

cttctatgga gttgatcctt ccaccgtcag gcatcagcta gggagtttct ctttagaacg    120

gtacaagggt cgtccagaaa tggtgcacaa rgttcacaag tggagagaag ctcttcacct    180
```

```
aatagctaac ctttcaggcc tggattcaag acaytggtaa gctcttctta ccataatata    240

gttacaaaaa tatatatact tacgtctttt ctttaaaaat atattttcta gtgttttcac    300

a                                                                    301


<210> SEQ ID NO 91
<211> LENGTH: 229
<212> TYPE: DNA
<213> ORGANISM: Brassica napus

<400> SEQUENCE: 91

tttaaattta gtgactaaac cagaatgaga caggtgaaac tcctagcgag atactattac     60

cttacgcgct ttgattagtt tgttttgagt ctctagcttt gcacgttgct ccctcctcct    120

cataattgca tggagctgct tcrcattgac aaagacaggc tcatcttcaa tgaggtccag    180

tggtaaagga acccgaccca ccatttgggg attccatacc tgcaggtct                229


<210> SEQ ID NO 92
<211> LENGTH: 229
<212> TYPE: DNA
<213> ORGANISM: Brassica napus

<400> SEQUENCE: 92

tttaaattta gtgactaaac cagaatgaga caggtgaaac tcctagckag atactattac     60

cttacgcgct ttgattagtt tgttttgagt ctctagcttt gcacgttgct ccctcctcct    120

cataattgca tggagctgct tcgcattgac aaagacaggc tcatcttcaa tgaggtccag    180

tggtaaagga acccgaccca ccatttgggg attccatacc tgcaggtct                229


<210> SEQ ID NO 93
<211> LENGTH: 121
<212> TYPE: DNA
<213> ORGANISM: Brassica napus

<400> SEQUENCE: 93

aaccaaaaga gtgtgcggtt tgatactcaa agtagtagtg atcttgaaac tgtggtgaga     60

ycttttggta aacacawctc gcaagtgttg ttttgccaac tytttcctca ccacaaatgc    120

c                                                                    121


<210> SEQ ID NO 94
<211> LENGTH: 121
<212> TYPE: DNA
<213> ORGANISM: Brassica napus

<400> SEQUENCE: 94

ctcaaatatc tgaaaatyta caaccacagg cgttacaaaa gtttagattc waggacacag     60

rgcaatccaa acgaaatttt acaaccttat aaacttagat tgctacagtg ggatgcatat    120

c                                                                    121


<210> SEQ ID NO 95
<211> LENGTH: 970
<212> TYPE: DNA
<213> ORGANISM: Brassica napus

<400> SEQUENCE: 95

aaccggagat gaccatcatt acctagctat tgcccatcgt cttacataga agaagcacac     60

ccaaacatag agcaaaagcc attagtttca aggtttcgga gctaaaacgg tctgtgtaga    120

ttgttctgac actcctcatc cctcgatcaa gcgtattcaa tatcttaggt ttctggatgc    180
```

```
aagcacatag ctgtacctat taaacgaaat aaaaggaagt tagctttgcg tatagagatt    240

gagagaataa ggattacagt agagggttgt tttacctctt cactacgtct tcctgatgga    300

aaacgagtga attgacttaa aaactgattc ggttggaagc aagggctgag atcaaggtca    360

tcaacagaat gatcaactga aagggagaaa gtttctaagg acatgcagcc atgtgaatat    420

aggtgcttaa tgctcaatgg aagctctgaa agtgatttta gtttcatgca atagttgagg    480

cagagagtta tcagcgagga kaggtctttg atgcttgtag gcactgtttc aaaatcgtgg    540

cgactgatat ctaaatacgt caactttgta aaaaaccgaa gctgatccga caatgtctcg    600

acatgtttgc agttgtcaag acgaagctca agcaaattgt attttccatg gtcttgttct    660

gcctgcgaaa tgctcaccaa tgtgtggagg ttggtacaat cagaaagtgt gagcgtctcc    720

agctgatata gttgtggcaa agcttcaagt ctacgacagt tacaaagcct cacatgtttt    780

aacttcgtaa gatgagtcat tgatgaaggt aaacccctga agaagtttcc acttaggttc    840

aacttctcta gaacttgcat gtgatgaatg tcatctggta tttcttcgat gtttaagttg    900

attagattta gctccatcaa ccagggaaaa tatgaaaagc tataacactc gaaaggatcc    960

ctttgctcac                                                           970
```

<210> SEQ ID NO 96
<211> LENGTH: 201
<212> TYPE: DNA
<213> ORGANISM: Brassica napus

<400> SEQUENCE: 96

```
gataaaatgg tttgattgat aagtaacctt gcaaatgtag gaaacatatt aagaacagaa     60

agcttcaact tcaattctat tgagagaaag aaaaaagcca yaaagaagca aatactgyac    120

ctctcctgca taatgcgata tcgtaaaatc agtctgagag agcttcggtt tggaaaatct    180

ctcgtgacct ttgaacgtct g                                              201
```

<210> SEQ ID NO 97
<211> LENGTH: 301
<212> TYPE: DNA
<213> ORGANISM: Brassica napus

<400> SEQUENCE: 97

```
acatgtgtat gataaatcaa ttgcaaaaca agaaaaatat attatttgtc catcaagaaa     60

ctgatacctt gatgactaaa ttttgtagct ttggggtctt tctgagcaga cgtggcagaa    120

cttgccagct tttatccttg tcgctctcga rtgataaagt aacgaggttg tcgaatgtga    180

agatcaattt gcagccgaaa tgaagcgcct aatgcatgta ttatcgaaac cataagcata    240

tatacagata tatatattca taatagattt atgaattaat tttattttag ttttactatt    300

t                                                                    301
```

<210> SEQ ID NO 98
<211> LENGTH: 121
<212> TYPE: DNA
<213> ORGANISM: Brassica napus

<400> SEQUENCE: 98

```
acaataaatt tataattgtt aaccragtgg tcttggccta gtggtaaatg agttctacct     60

rgagtttctg ccctaggttc gattcccgga ttaagtggca agaaaaaccg gatttatatg    120

g                                                                    121
```

<210> SEQ ID NO 99
<211> LENGTH: 698
<212> TYPE: DNA
<213> ORGANISM: Brassica napus

<400> SEQUENCE: 99
agctttcaca aatctccacc agcttggttt aagcccaacc ttggcccatc cgacaaccct 60
agtgccgaca gcttcctccc ttgtctcttt gtctttcttg tgaaatgaga aagtcgatct 120
tgactctctc tctctcttcc tcgtctctct cactcgcgac ccttctccgc cgattcggac 180
ttggtgtcgt cgtgaggagt tataggttgc tctgcctcgc aaccgtagct ccatgaaggt 240
ctcgtcagct ccaccgcgat ggcgtcgcat ctccttctct ccattcttcc ctcgaagtyt 300
cttcgccgaa cggcgatttg cttctctgat gatggctcac accatcgtga ctccatcatc 360
tttcctccct aatatcccca ggtacatcta atctctcctc ttcatgagcg attaggatca 420
tctgttaggg atactaagtg agtcttgtgg gaacttgagc taacttgagg attctttgcc 480
tttgcatgtc gtctcaggtg actcgtgact ctatctctag tcgcgattga gaacctgaca 540
tgtcggtaag ctcttgcctg agctccatca tcacgctcta cctctttcgt agataacgta 600
agctcatgtc ttaacgaacc ttctctaata tgcttttcac ttgtcgatct gactcttctg 660
tttctgtttc agaagccggt ttagctctgt gacgagct 698

<210> SEQ ID NO 100
<211> LENGTH: 749
<212> TYPE: DNA
<213> ORGANISM: Brassica napus

<400> SEQUENCE: 100
agcttctggg cagaggcagc atctactgct atccatgtga tcaatagatc acctaactct 60
acactcgagt tcagaatgcc tgaagaattg tggaccggcg cgaaacctga cttgggacat 120
ctaagaactt ttggatgcac tgcgtatgtc cacataactg aggagaaaac aggacctaga 180
gccatcaaag gggtgtttgt ggggtaccct atgggtacta aaggctatcg agtttggata 240
gaggatgarg gcagatgcag aacaagtaga aatgttgttt tcaacgaaga cgagctatac 300
aagcacaccg ttgctaaagc aaaagaaagc acaggagtga ctaaagatac agagaaacga 360
gctaaaaaga gggtctcatt cagtgatgat ttgatcagag ggccttctcc ttctgtcgaa 420
tccaaagaca catctgatca aggtggagaa gaatcatcat catctgagga gtcgagtagt 480
tcgagtgacc aagaacagaa tgacgaggtt gaaagtgaaa gtggtgacac tggatcttta 540
gacacctatg ttctagctcg agacagagca agaagacaga acgtgaggcc cccatctcgc 600
tatgaggatg gaaactttgt agcctatgcg ctaaatgtca tcaacgactt agaggttgaa 660
gaacctaaat cctacgctga ggcaatgaaa agtccacaga agaagttgtg gaaaaatgca 720
gctgaggagg agatggaatc tcataggaa 749

<210> SEQ ID NO 101
<211> LENGTH: 574
<212> TYPE: DNA
<213> ORGANISM: Brassica napus

<400> SEQUENCE: 101
aattcttgaa gctagttgca gatttaaaca atttgcaagt tgaagtatcc gaggaagttc 60
aagctatcct attgctaagt tctctaccaa acaagtatga tcaactcaaa gagactctca 120
agtatggaag agacacccta agcctagctg aggttacagg ggctgcaagg tcgaaagaaa 180

```
gagagttgat tgagagtggt aagtttacca ggtctggtgg agaaggtctg atggtgacag    240
acagaggaag atcagaccaa cgctctggca aaggaaatgg aaaatcctac aggggaagat    300
ccaagagcag acagggacgt tccaagtcgc gtcctaggaa caccaaaggc tcaaagggat    360
gttttgtatg cgggaaggag ggccactgga agcgtgactg ccctgataag aaaccttaca    420
aaacgccaga ctcagcaaat gttgtggcag agtccaakga acctctaatc ctcaccgtga    480
gcacccaata ctccaaggac gaatgggtga tggactctgg ctgctcgttc cacatcacac    540
cagacaagag ttttttgttt gacctggaag aatt                                574
```

<210> SEQ ID NO 102
<211> LENGTH: 524
<212> TYPE: DNA
<213> ORGANISM: Brassica napus

<400> SEQUENCE: 102

```
agcttctcat cggtgagaat agctttcagt ccaagcactc caaagtgagc aagcattctc     60
actttccata gggcgaagtc accatctcct tcgaaacggt cgatctcgat gcgttccttt    120
gacttcaccw ttgagaaggt actgagtatg cacctcctct gtctctctct ctatcctaag    180
caaccttgat gaaaaccgga gctctgatac cacttgtaga atgtaattag ctcaggttaa    240
cttaggttag aggttatatt gatctaggtc taatactgaa agtaaagaca caagcgattt    300
aacgacttcc cggccctcgg cgcggtacgt gtcgtgggag aacttctgct cccaaaatcc    360
actagatcaa agagtctcta gcaccactaa atcagtgtgc tagataggta ggttacaata    420
agatcccttc aacttagcta gggaatacaa caaccttaat atgagacaat agccttaagt    480
ctaagctagt tgtccttgtt gaagtctcct ttcccttgat gctg                     524
```

<210> SEQ ID NO 103
<211> LENGTH: 681
<212> TYPE: DNA
<213> ORGANISM: Brassica napus

<400> SEQUENCE: 103

```
aaagtgagca agcattctca ctttccatag ggcgaagtca ccatctcctt cgaaacggtc     60
gatctcgatg cgttcctttg acttcaccat tgagaaggta ctgagtatgc acctcctctg    120
tctctctctc tatcctaagc aaccttgatg aaaaccggaa gctctgatac cacttgtaga    180
atgtaattag ctcaggttaa cttaggttag aggttatatt gatctaggtc taatactgaa    240
agtaaagaca caagcgattt aacgacttcc cggccctcgg ctcggtacgt gtcgtgggag    300
aacttctgct cccaaaatcy actagatyaa agagtctcta gcaccactaa atcagtgtgc    360
tagataggta ggttacaata agatcccttc aacttagcta gggaatacaa caaccttaat    420
atgagacaat agccttaagt ctaagctagt tgtccttgtt gaagtctcct ttcccttgat    480
gctgtatctt gttgactgat ctctgatgct ataacctgct gttgttgctt ctatccggta    540
accctaatca cccatactaa cattgtatat atatgtgtcg tatgtgatca ggtagtgcaa    600
cctggagtgg gcctgcgcat gacttcggcc catcagatgt gatgctgctg ctggcccatc    660
acgcagggat aaacccaagc t                                              681
```

<210> SEQ ID NO 104
<211> LENGTH: 519
<212> TYPE: DNA
<213> ORGANISM: Brassica napus

<400> SEQUENCE: 104

```
gctgcaatcg ccttttgtgg gaggttgatg caagggaata gatacatagc tccttcagct     60
ctgttgcatg ttacacctc taacttgttc aaagcttctt caagggtctg tgtggctcaa    120
ctcaaaactc attaaaacca taacaaaaat ctagttccat gattgctagt aagttctgtg    180
agaatggcta acctttgcac gtgttgctaa agacgagagg atcccctctt tctctgctat    240
gtatgaatca tacgagtcat caccaggctg atcaaattac attaaagagc tgttaaagac    300
aattgagctt ttaaaccaaa ccagctgtta aagtaataca ataccttggg agggctcatg    360
acgaggctgg cgagaatttg accagagatg ttggagcaaa gattgacaga agccactttg    420
tatatctgtt ctcttacatc agaagtgaat ccggtaacct ccatgtaacc gcctctcttc    480
ccacactctc cataataccc tattgaaaga aaggagtac                           519
```

<210> SEQ ID NO 105
<211> LENGTH: 946
<212> TYPE: DNA
<213> ORGANISM: Brassica napus

<400> SEQUENCE: 105

```
tatatgttct gaacctcact acaattcagc atctgagctt gttttttttt ctttcttcta     60
gtggtgtaag attttgttta accaatggat gttgcaattt ttctatcagt tcggattcta    120
ttgatcgtgc ttggaagatc ctcgaccaaa tccccgggaa agctaccggt gcttacagcc    180
acagccaggt tttgtggcct ttgtcaatct taaacagtga atgatggatg atacactctc    240
ttaatcttct gctttgtctc tcagggtatc aagggactac gtgatgcgat agctgctgga    300
atcgaagccc gtgacggttt ccctgctgat cctaatgata ttttcatgac agatggtgca    360
agccctgggg taaccagtca tcaaactttc cctaaactta tataaattac agaaaaaagg    420
ttagtaatgt tactctcgtt cttttaggtt cacatgatga tgcaactcct cataagttca    480
gagaaagatg gaatcctttg ycctattcct cagtacccct tgtactcagc ttctattgcc    540
cttcacggcg gtagtctggt atgttccttt atgtctctct gatgcatgtc tatagtgact    600
tctgattgct gtcatcttct tgaggtaggt tccatactac ctagacgaag catcagggtg    660
gggtcttgaa atatctgagc tgaagaagca gcttgaggat gctaagtcaa aaggcatcac    720
tgtaagagcc ttggcggtta ttaaccctgg taaccctaca ggacaggtaa agactaaacc    780
acaaatctat ttccatccaa attcaacact ttgtctgaac tctagcctgt tattttcctg    840
gttaaaggtt ctgtcagaag aaaaccagcg tgacattgtt gatttctgta agaaagaagg    900
cttggtgctt ctagcagacg aggtttatca ggaaacgttt acgtcc                   946
```

<210> SEQ ID NO 106
<211> LENGTH: 121
<212> TYPE: DNA
<213> ORGANISM: Brassica napus

<400> SEQUENCE: 106

```
tctcgtgacc cataatcaag cattgaatat atattctgag agaagccata tatattcaaa     60
ytaattaaaa actaatmtat tcwgaaagta twgtgaaata ttgaatatta cgagcaagta    120
g                                                                    121
```

<210> SEQ ID NO 107
<211> LENGTH: 121
<212> TYPE: DNA
<213> ORGANISM: Brassica napus

<400> SEQUENCE: 107
atcaacaaga gaaaagctaa caagacttgc acataaytct aaacaggaag aaaaactgag 60
yagaacatga acagagacca aaaggtccaa aactgatttg atttaagggc cagtttgaat 120
a 121

<210> SEQ ID NO 108
<211> LENGTH: 408
<212> TYPE: DNA
<213> ORGANISM: Brassica napus

<400> SEQUENCE: 108
agtttggttt aatgtgatta acaattgtgg tttaggtgta tggtccaacg aggttgatat 60
ggggagcgaa aggagaggag caagaggcgg ggacgaagga gttcattgag atgctcaaga 120
tgctagagtc tgagcttgga gacaagactt actttggagg ygaaacattc ggttatgtgg 180
atatagctat gattggattc tactgctggt tcgacgtttt ggagaagtgt gggaatttta 240
gcatcgaagc agagtgtcca aagctgattg cttgggctaa aaggtgtatg aagagagaga 300
gtgtggctaa gtctcttcct gattcaaaca agatcactaa gttcgttcct gagctaaaga 360
aaaaaattgg catcgagtag ttctgttata atttaatctg tgttctgt 408

<210> SEQ ID NO 109
<211> LENGTH: 301
<212> TYPE: DNA
<213> ORGANISM: Brassica napus

<400> SEQUENCE: 109
tgaagcataa cctcaaacgc ctcagcaaca tcttcacagt aaagatagct acgaacatta 60
gtaccatctc tatgaatagg aagagctttc cctcttatca ccaacaaaaa taaacttagg 120
tccaacaaca gcatcttcat ctgtctcagc yatwaacctc atctgctctc acatgtataa 180
mcctcctgat ctatcctcta gtcactttac aagcctcgag aaggacatgc gttccgtaga 240
tattgttttt tagtgaactc gaaactgtta cggaaggagt tgtccacgtg agttctgtga 300
g 301

<210> SEQ ID NO 110
<211> LENGTH: 301
<212> TYPE: DNA
<213> ORGANISM: Brassica napus
<220> FEATURE:
<221> NAME/KEY: misc_feature
<222> LOCATION: (242)..(271)
<223> OTHER INFORMATION: where n is a, t, c, or g

<400> SEQUENCE: 110
acaaagctgt aattaaaaga taagacacga gtttcggttt ggttttgtgg ataaaaggat 60
aagaagagca ttttcccctt ttttatcgta atttttgttt tataaaagga taattatatt 120
aagtttattt tgtttataca acgatcaatg ktttttgtaa ttctcattta tataacgatt 180
ctcacacctt tattgtttta gatggatatg ttgggtgaca actcacaagt agatttttttc 240 annnnnnnnn nnnnnnnnnn nnnnnnnnnn ngctagttgg taaaaagaaa aagaaaagaa 300
g 301

<210> SEQ ID NO 111
<211> LENGTH: 1212
<212> TYPE: DNA

```
<213> ORGANISM: Brassica napus
<220> FEATURE:
<221> NAME/KEY: misc_feature
<222> LOCATION: (78)..(78)
<223> OTHER INFORMATION: where n is a, t, c, or g
<220> FEATURE:
<221> NAME/KEY: misc_feature
<222> LOCATION: (1113)..(1113)
<223> OTHER INFORMATION: where n is a, t, c, or g

<400> SEQUENCE: 111

cccgcgtccg ctgacggaca cggagatggc attgtgttac tggaaagctc tgttactact     60

actgctttca tgcctctntc agtgtttcgt atgctagtct cggcgatgcc gatccaaact    120

acagggcatg tgttggagaa tgcgagataa gcggctgcgt tggacaacta tgctttcctc    180

agtgcaactc ttcatccaac actggtccat ggtacacaca agagcctctg tacctacaat    240

ggcaaaagtg gggatgtcaa ggtgattgcc gttaccactg tatggttaac agagagaaag    300

aacgcgaaac tctcggtcaa cccccactca agtatcatgg taaatggcct ttcaagcgtc    360

tccttgggat tcaggagcct gcttctgttg ctttctctgt gctcaaccta gcgatgcatt    420

tccacggctg gatctccttc ttcattacgc tttactataa gctgcctctc agagaagata    480

agacggctta ctatgaatac gttggtctgt ggcatatcta cggtttcttg tcaatgaact    540

cttggttctg gagtgcggtt ttccacactc gggatgttga catcactgag aggttggact    600

actcgtctgc aatagcggtt atcggattct cactcattgt atccatcttg agaacgtttg    660

atgttcgggt agaggctgca agagtcatgg tatctgctcc agtgctagct tttgtcacca    720

ctcacatact gtatattaac ttctacaagc tcgactatgg ttggaacatg attgtgtgtg    780

tggccatggg agtcgctcag cttctcctat gggcaagatg ggctgctgtc tctagacatc    840

cttctaastg gaaactttgg atggtggtga tagcttcagg cttagctatg cttttggaga    900

tatatgactt tcctccatat gaaggctact tcgatgctca ctccatttgg catgctgcaa    960

ccattcctct aactgttctc tggtggagct ttattagaga cgatgctgag ttcagaactt   1020

ctagtcttct caagaaatct aagacaaagg ctaagtaagc ttatttgtct gacagatgca   1080

gaggtttctt gagtttttat ttccaatgtt ttntattcag agatttgtct tggccgtcct   1140

tacttttggt caattgagat ttgatattag tttctcattc atacacacgc ttatgctaat   1200

ctttttggac tc                                                        1212
```